US012709721B2

(12) United States Patent
Zeese et al.

(10) Patent No.: US 12,709,721 B2
(45) Date of Patent: Aug. 18, 2026

(54) UNIT DOSE ARTICLE FOR PACKAGING PERSONAL CARE PRODUCTS

(71) Applicant: MONOSOL, LLC, Merrillville, IN (US)

(72) Inventors: Nicholas Zeese, Merrillville, IN (US); Jonathon Knight, Merrillville, IN (US); Victoria Bridewell, Merrillville, IN (US)

(73) Assignee: MONOSOL, LLC, Merrillville, IN (US)

( * ) Notice: Subject to any disclaimer, the term of this patent is extended or adjusted under 35 U.S.C. 154(b) by 949 days.

(21) Appl. No.: 17/781,663

(22) PCT Filed: Dec. 2, 2020

(86) PCT No.: PCT/US2020/062798

§ 371 (c)(1),
(2) Date: Jun. 1, 2022

(87) PCT Pub. No.: WO2021/113294

PCT Pub. Date: Jun. 10, 2021

(65) Prior Publication Data

US 2022/0403303 A1 Dec. 22, 2022

Related U.S. Application Data

(60) Provisional application No. 62/942,369, filed on Dec. 2, 2019.

(51) Int. Cl.
*C11D 17/04* (2006.01)
*A61K 8/11* (2006.01)
(Continued)

(52) U.S. Cl.
CPC .............. *C11D 17/045* (2013.01); *A61K 8/11* (2013.01); *A61K 8/345* (2013.01); *A61K 8/37* (2013.01);
(Continued)

(58) Field of Classification Search
None
See application file for complete search history.

(56) References Cited

U.S. PATENT DOCUMENTS 5,780,047 A 7/1998 Kamiya et al.
6,166,117 A * 12/2000 Miyazaki ............ C11D 3/3955 525/61
(Continued)

FOREIGN PATENT DOCUMENTS

EP 0957158 B1 11/2003
JP H5-321105 A 12/1993
(Continued)

OTHER PUBLICATIONS

Translation of Official Action issued in Russian Patent Application No. 2022117628, dated Sep. 24, 2024.
(Continued)

*Primary Examiner* — Dominic Lazaro
(74) *Attorney, Agent, or Firm* — Benesch Friedlander Coplan & Aronoff LLP

(57) ABSTRACT

Disclosed herein are unit dose articles comprising one or more compartments, the one or more compartments comprising a nonwoven web and a water soluble film.

19 Claims, 3 Drawing Sheets

(51) Int. Cl.

| | |
|---|---|
| ***A61K 8/34*** | (2006.01) |
| ***A61K 8/37*** | (2006.01) |
| ***A61K 8/39*** | (2006.01) |
| ***A61K 8/41*** | (2006.01) |
| ***A61K 8/46*** | (2006.01) |
| ***A61Q 5/02*** | (2006.01) |
| ***A61Q 5/12*** | (2006.01) |
| ***A61Q 19/10*** | (2006.01) |
| ***C11D 1/83*** | (2006.01) |
| ***C11D 3/20*** | (2006.01) |
| ***C11D 3/30*** | (2006.01) |
| ***C11D 3/50*** | (2006.01) |
| ***C11D 11/00*** | (2006.01) |
| *C11D 1/22* | (2006.01) |
| *C11D 1/72* | (2006.01) |

(52) U.S. Cl.

CPC .................. *A61K 8/39* (2013.01); *A61K 8/41* (2013.01); *A61K 8/466* (2013.01); *A61Q 5/02* (2013.01); *A61Q 5/12* (2013.01); *A61Q 19/10* (2013.01); *C11D 1/83* (2013.01); *C11D 3/2044* (2013.01); *C11D 3/2065* (2013.01); *C11D 3/2068* (2013.01); *C11D 3/2079* (2013.01); *C11D 3/30* (2013.01); *C11D 3/505* (2013.01); *C11D 1/22* (2013.01); *C11D 1/72* (2013.01); *C11D 2111/12* (2024.01)

(56) References Cited

U.S. PATENT DOCUMENTS

| | | | | |
|---|---|---|---|---|
| 6,719,740 B2 | 4/2004 | Burnett et al. | | |
| 7,022,656 B2 * | 4/2006 | Verrall | C08F 8/44 510/438 | |
| 2012/0048769 A1 * | 3/2012 | Sivik | A61Q 5/00 206/524.1 | |
| 2015/0210969 A1 * | 7/2015 | Brandt-Sanz | B29C 51/10 510/439 | |
| 2018/0369859 A1 | 12/2018 | Boswell et al. | | |
| 2022/0403303 A1 | 12/2022 | Zeese et al. | | |

FOREIGN PATENT DOCUMENTS

| | | | | |
|---|---|---|---|---|
| JP | 10-008098 A | 1/1998 | | |
| JP | 2015-509147 A | 3/2015 | | |
| JP | 2016-540701 A | 12/2016 | | |
| WO | 2013/103630 A1 | 7/2013 | | |
| WO | 2015/034975 A1 | 3/2015 | | |
| WO | 2017180888 A1 | 10/2017 | | |
| WO | WO-2018111299 A1 * | 6/2018 | D01D 5/0985 | |
| WO | 2021113294 A1 | 6/2021 | | |

OTHER PUBLICATIONS

Translation of Second Examination Opinion issued in Chinese Patent Application No. 202080092230.9, dated Nov. 1, 2024.

Translation of Office Action issued in Japanese Patent Application No. 2024-000314, dated Sep. 10, 2024.

Office Action issued in Russian patent application No. 2022112801, dated Feb. 28, 2024.

Office Action issued in Canadian patent application No. 3,160,009, dated May 2, 2024.

Written Opinion of the International Searching Authority for International Application No. PCT/US2020/062798, issued Apr. 12, 2021.

International Search Report of the International Searching Authority for International Application No. PCT/US2020/062798, issued Apr. 12, 2021.

Communication pursuant to Article 94(3) EPC issued in European Patent Application No. 20842602.3, dated Feb. 6, 2025.

Search Report issued in Brazilian Patent Application No. BR112022010786-6, dated Feb. 25, 2025.

Official Action issued in Japanese Patent Application No. 2024-000314, dated Mar. 6, 2025.

Oct. 7, 2022 First Examination Report issued by the Indian Patent Office for Indian Patent Application No. 202217030424. [Includes English translation.].

Jul. 15, 2022 Communication pursuant to Rules 161(1) and 162 EPC issued by the European Patent Office for European Patent Application No. 20842602.3.

Examination Report issued in Australian Patent Application No. 2020395121, dated Apr. 26, 2024.

Office Action issued in Chinese Patent Application No. 202080092230.9, dated Apr. 3, 2024.

Office Action dated Jul. 3, 2023 for Japanese Application No. 2022-532084, 16 pages.

May 16, 2023 Office Action issued by the Canadian Patent Office for Canadian Patent Application No. 3, 160,009.

May 17, 2022 International Preliminary Report on Patentability issued by the International Bureau of WIPO for International Application No. PCT/US2020/062798.

Rejection Decision issued in Patent Application No. 202080092230.9, dated Apr. 25, 2025.

* cited by examiner

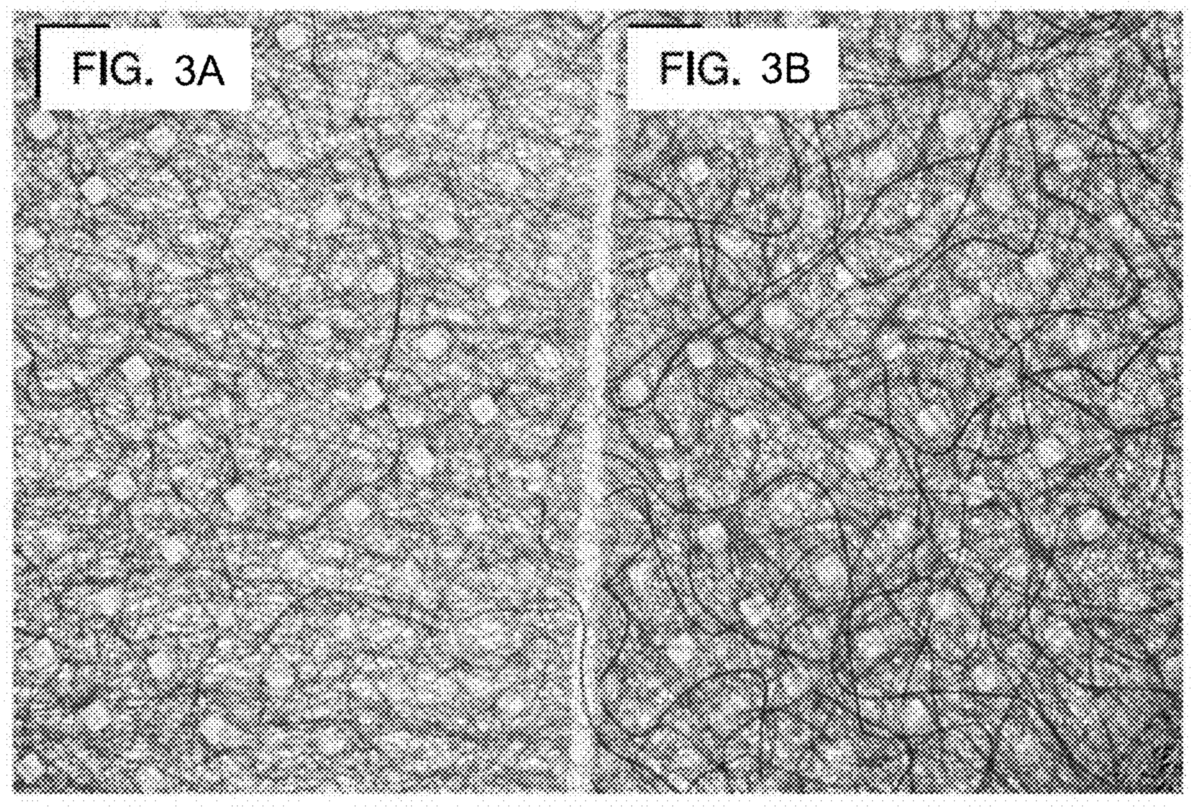
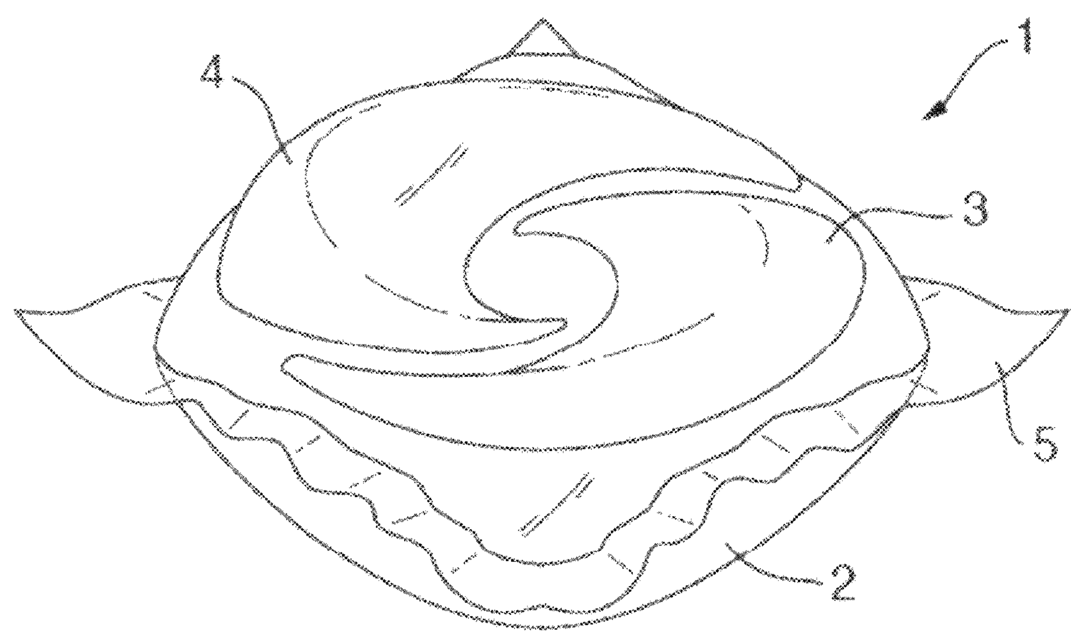
FIG. 4

UNIT DOSE ARTICLE FOR PACKAGING PERSONAL CARE PRODUCTS

CROSS-REFERENCE TO RELATED APPLICATIONS

This application is a U.S. national stage application under 35 U.S.C. § 371 of International Application No. PCT/US2020/062798, filed Dec. 2, 2020, which claims the benefit under 35 U.S.C. § 119(e) of U.S. Provisional Patent Application No. 62/942,369, filed Dec. 2, 2019, the entire disclosures of which are hereby incorporated by reference.

FIELD OF THE INVENTION

The present disclosure relates generally to unit dose articles having nonwoven webs and water soluble films, as well as related compositions. More particularly, the disclosure relates to unit dose articles for packaging personal care products for prolonged release.

BACKGROUND

Water soluble packaging materials are commonly used to simplify dispersing, pouring, dissolving and dosing of a material to be delivered. Traditional packaging materials include water soluble films and pouches made therefrom are commonly used to package compositions such as laundry detergents, dish detergents, or personal care compositions. A consumer can directly add the pouched composition to water. Advantageously, this provides for accurate dosing while eliminating the need for the consumer to measure the composition. Traditional water soluble films can be unstable in humid environments, such as in a bathroom, which can affect the properties of the film, for example, the mechanical properties of the film may deteriorate over time. Further, pouches made from water soluble films release the contents of the pouch immediately upon dissolution of the pouch. Thus, water soluble films cannot offer slow release of contained compositions while maintaining mechanical integrity of the film and/or pouch. In addition, some currently marketed pouches made of water soluble polymeric films have an unpleasant rubbery or plastic-like feel when handled by the consumer.

Thus, there exists a need in the art for unit dose packaging that is pleasant to handle, can have prolonged release of the contained composition, and can withstand humid environments, like a bathroom.

SUMMARY

One aspect of the disclosure provides a unit dose article including one or more compartments comprising a water soluble film in the form of a pouch defining a first interior pouch volume, the water soluble film comprising a water soluble resin; a nonwoven web in the form of a pouch defining a second interior pouch volume encompassing the water soluble film, the nonwoven web comprising a plurality of fibers; and a first composition contained by the first compartment; wherein when the first compartment is contacted with water, the first composition is released and the unit dose article prolongs the release of the first composition compared to an identical unit dose article comprising the water soluble film in the form of a pouch and not including the nonwoven web in the form of a pouch.

Another aspect of the disclosure provides unit dose article comprising a first compartment, comprising: a water soluble film in the form of a pouch defining a first interior pouch volume, the water soluble film comprising a water soluble resin; a nonwoven web in the form of a pouch defining a second interior pouch volume encompassing the water soluble film, the nonwoven web comprising a plurality of fibers; and a first composition contained by the first compartments, wherein the dissolution time of the nonwoven web is greater than the dissolution time of the water soluble film, according MSTM 205.

Another aspect of the disclosure provides unit dose article comprising a first compartment, comprising: a water soluble film in the form of a pouch defining a first interior pouch volume, the water soluble film comprising a water soluble resin; a nonwoven web in the form of a pouch defining a second interior pouch volume encompassing the water soluble film, the nonwoven web comprising a plurality of fibers; and a first composition contained by the first compartments, wherein the water-soluble film and the nonwoven web are in the form of a laminate and have a degree of lamination in a range of about 5% to about 100%.

Another aspect of the disclosure provides a unit dose article comprising a compartment comprising a water soluble film in the form of a pouch defining a first interior pouch volume, the water soluble film comprising a water soluble resin; a nonwoven web in the form of a pouch encompassing the water soluble film, the nonwoven web comprising a plurality of fibers comprising a fiber type comprising a blend of PVOH homopolymer fiber forming materials and a fiber type comprising a non-water soluble, biodegradable fiber forming material; wherein the water soluble film and the nonwoven web form a laminate and a personal care composition is contained by the unit dose article and comprises a surfactant.

Another aspect of the disclosure provides a unit dose article comprising two or more compartments comprising a water soluble film in the form of a pouch defining a first interior pouch volume, the water soluble film comprising a water soluble resin; a nonwoven web in the form of a pouch encompassing the water soluble film, the nonwoven web comprising a plurality of fibers comprising a fiber type comprising a non-water soluble, biodegradable fiber forming material; wherein the water soluble film and the nonwoven web form a laminate, and a personal care composition contained by the unit dose article comprising a surfactant.

Another aspect of the disclosure provides a method of preparing a unit dose article according to the disclosure, the method comprising forming the water soluble film into an open pouch defining an open pouch volume; adding the first composition into the open pouch volume; and sealing the film to form the first interior pouch volume.

For the articles, water soluble films, nonwoven webs, fibers, and compositions described herein, optional features, including but not limited to components and compositional ranges thereof, fiber forming materials, multiple layer constructions, fiber geometries, and/or mechanical properties are contemplated to be selected from the various aspects and embodiments provided herein.

Further aspects and advantages will be apparent to those of ordinary skill in the art from a review of the following detailed description. While the articles, water soluble films, nonwoven webs, fibers, and compositions of the disclosure are susceptible to embodiments in various forms, the description hereafter includes specific embodiments with the understanding that the disclosure is illustrative and is not intended to limit the disclosure to the specific embodiments described herein.

BRIEF DESCRIPTION OF THE DRAWINGS

FIG. 3A is a micrograph image of a nonwoven web of the disclosure having a softness rating of 1.

FIG. 3B is a micrograph image of a nonwoven web of the disclosure having a softness rating of 5.

FIG. 4 is an illustration of a multi-compartment unit dose article of the disclosure.

DETAILED DESCRIPTION

Figure 1:
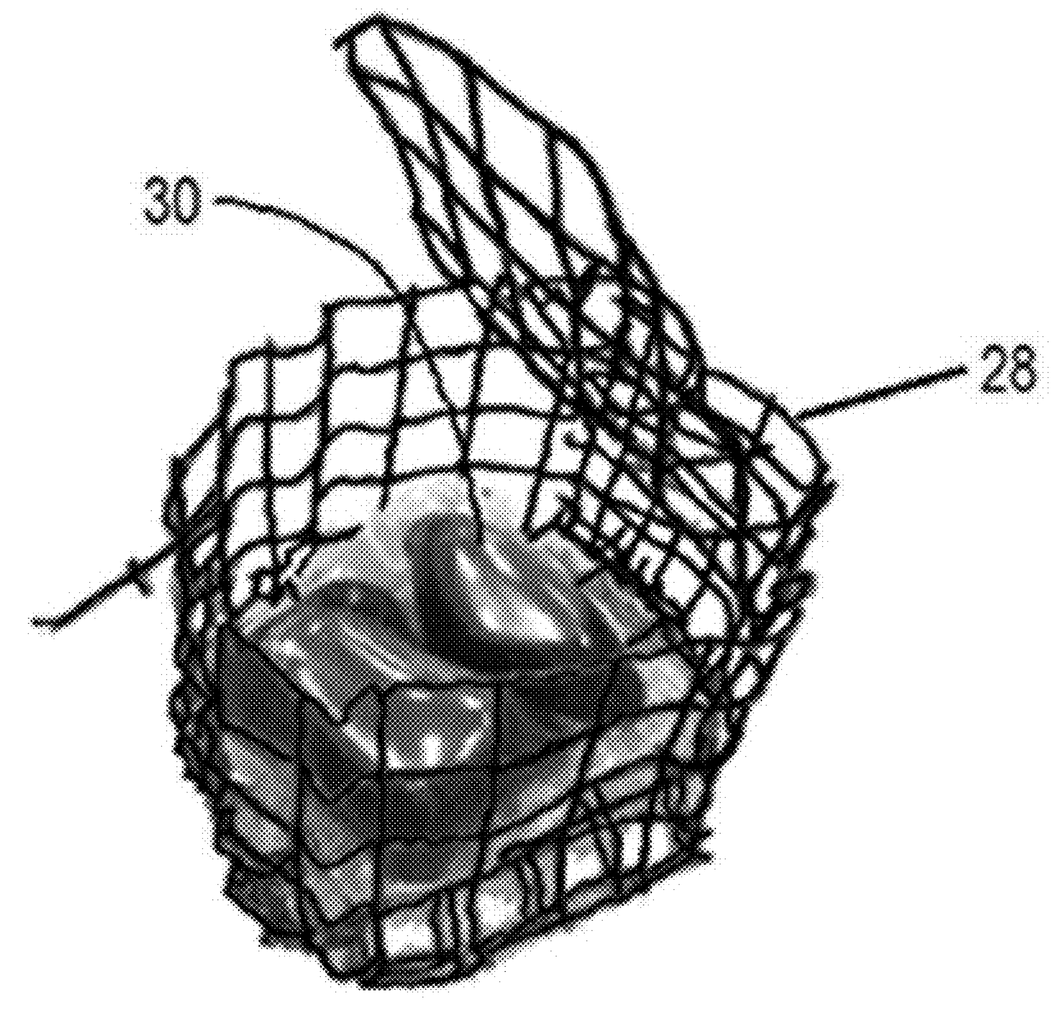
FIG. 1 is an illustration of a wire frame cage (shown with the top open, to better illustrate water-soluble pouches contained therein) for use in the Liquid Release Test described herein.

In the disclosure presented herein, one aspect provides a unit dose article comprising one or more compartments comprising a water soluble film and a nonwoven web. In embodiments, the water soluble film can be in the form of a pouch defining a first interior pouch volume, and the nonwoven web can be in the form of a pouch defining a second interior pouch volume encompassing the water soluble film. In embodiments, the water soluble film can comprise a water soluble resin, the nonwoven web can comprise a plurality of fibers, and a first composition can be contained by the unit dose article. In embodiments, the water soluble resin can comprise a polyvinyl alcohol homopolymer, a polyvinyl alcohol copolymer, or a combination thereof. In embodiments, the unit dose article comprises a first compartment, and when the first compartment is contacted with water, the first composition is released and the unit dose article prolongs the release of the first composition compared to an identical unit dose article comprising the water soluble film in the form of a pouch and not including the nonwoven web in the form of a pouch.

Another aspect of the disclosure provides unit dose article comprising a first compartment, comprising: a water soluble film in the form of a pouch defining a first interior pouch volume, the water soluble film comprising a water soluble resin; a nonwoven web in the form of a pouch defining a second interior pouch volume encompassing the water soluble film, the nonwoven web comprising a plurality of fibers; and a first composition contained by the first compartments, wherein the dissolution time of the nonwoven web is greater than the dissolution time of the water soluble film, according MSTM 205.

Another aspect of the disclosure provides unit dose article comprising a first compartment, comprising: a water soluble film in the form of a pouch defining a first interior pouch volume, the water soluble film comprising a water soluble resin; a nonwoven web in the form of a pouch defining a second interior pouch volume encompassing the water soluble film, the nonwoven web comprising a plurality of fibers; and a first composition contained by the first compartments, wherein the water-soluble film and the nonwoven web are in the form of a laminate and have a degree of lamination in a range of about 5% to about 100%, The unit dose article according to the disclosure can be designed to provide one or more advantages, for example, a more "natural" feel for consumer benefit, stability in humid environments, increased functionality, such as exfoliation and personal care composition delivery in aqueous environments, and/or prolonged release of a liquid composition while maintaining mechanical integrity of the article for a duration of use.

As used herein, a "plurality of fibers" can consist of a sole fiber type or can comprise two or more different fiber types. In embodiments wherein the plurality of fibers comprises two or more different fiber types, each fiber type can be included in generally any amount, for example, from about 0.5 wt. % to about 99.5 wt. % of the total weight of the plurality of fibers. In embodiments wherein the plurality of fibers consists of a sole fiber type, the plurality of fibers is substantially free of a second or more fiber types. A plurality of fibers is substantially free of a second or more fiber types when the plurality of fibers comprises less than about 0.5 wt. % of the second or more fiber types. In general, the difference between fiber types can be a difference in fiber length to diameter ratio (L/D), tenacity, shape, rigidness, elasticity, solubility, melting point, glass transition temperature ($T_g$), chemical composition, color, or a combination thereof.

Without intending to be bound by theory, it is believed that there is a positive correlation between the time it takes for a composition to be released from an article according to the Liquid Release Test described herein, and the residence time of the liquid composition in or on the article during conditions of use. The conditions of use generally include wetting of the article and a mechanical agitation, such as to form a lather from the composition contained in the article. As used herein and unless specified otherwise, the residence time of the liquid composition in or on the article during conditions of use refers to length of time the composition remains in or on the article, for example as a liquid and/or foam (e.g., soap bubbles). Accordingly, the "prolonged release" of a composition from an article can be characterized by the liquid release time of the article as determined according to the Liquid Release Test described herein, wherein the article provides a "prolonged release" when the article does not begin to release the composition for at least about 1 minute according to the Liquid Release Test. For example, a unit dose article may not begin to release the composition for at least about 1 minute, at least about 2 minutes, at least about 3 minutes, or at least about 5 minutes, for example in a range of about 1 to about 15 minutes, about 1 to about 10 minutes, about 1 to about 8 minutes, or about 1 to about 5 minutes according to the Liquid Release Test. Additionally or alternatively, the "prolonged release" of a composition from a unit dose article of the disclosure can be characterized by a liquid release time as determined according to the Liquid Release Test as described herein of at least about 1.3× (1.3 times) longer compared to an identical unit dose article comprising the water soluble film in the form of a pouch and not including the nonwoven web in the form of a pouch. For example, the "prolonged release" of a composition from a unit dose article of the disclosure can be characterized by a liquid release time of at least about 1.4×, about 1.5×, about 1.9×, about 2.7×, about 3.0×, about 3.3×, about 3.5×, about 3.6×, about 4.2×. about 4.3×, about 4.7×, about 5.6×, about 6.1×, about 7.1×, about 10.5×, about 11.6×, or about 22.3×, longer compared to an identical unit dose article comprising the water soluble film in the form of a pouch and not including the nonwoven web in the form of a pouch. Alternatively or additionally, the "prolonged release" can be characterized by the amount of composition that is retained in the unit dose article, wherein the article provides a "prolonged release" when at least 30% of the composition is retained in the unit dose for about 5 minutes after contacting the article with water having a temperature of about 45° C. or less. For example, a unit dose article can retain at least about 30%, about 40%, about 50%, about 60%, about 70%, about 80%, or about 90% of the composition after contact with water having a temperature of about 45° C. or less, for example, in a range of about 0° C. to about 43° C., about 0° C. to about 40° C., about 10° C. to about 40° C., about 20° C. to about 40° C., about 20° C. to about 30° C., or about 30° C. to about 40° C. As used herein, the composition is "retained" if the composition remains in or on the article, for example, as a liquid and/or foam (e.g., soap bubbles). As used herein, the term "contact with water" and variations thereof (e.g., "contacted with water") can refer to the unit dose article being submerged in water, showered with water, or generally wetted with water. In embodiments, the unit dose article is contacted with water when it is showered with water. In embodiments, the unit dose article is contacted with water when it is generally wetted with water, such as, for example, when water is applied to a composition surrounding the unit dose article and the water diffuses through the surrounding composition to contact the pouch (e.g., a pouch buried in dirt or soil that is wetted when the dirt or soil is watered). Further still, the "prolonged release" of an article can be characterized by the amount of surface area of the article that is retained after 300 seconds when tested in accordance with MSTM-205 at 40° C. In embodiments, a unit dose article is considered suitable for prolonged release of a composition if the article comprises a film, nonwoven web, or combination thereof that retains at least 50% of its original surface area after 300 seconds, tested in accordance with MSTM-205 at 40° C. For example, a unit dose article can retain at least about 50%, at least about 60%, at least about 70%, at least about 75%, at least about 80%, at least about 85%, at least about 90%, or at least about 95% of its pre-MSTM-205 surface are after 300 seconds when tested in accordance with MSTM-205 at 40° C.

In embodiments, the first compartment of the unit dose article prolongs the release of the first composition after contact with water at a temperature in the range of about 30° C. to 40° C. for a time period of at least about 30 seconds compared to an identical unit dose article comprising the water soluble film in the form of a pouch and not including the nonwoven web in the form of a pouch. In embodiments, the first compartment of the unit dose article prolongs the release of the first composition after contact with water at a temperature in the range of about 30° C. to 40° C. for a time period of at least about 1 minute compared to an identical unit dose article comprising the water soluble film in the form of a pouch and not including the nonwoven web in the form of a pouch. In embodiments, the first compartment of the unit dose article prolongs the release of the first composition after contact with water at a temperature in the range of about 30° C. to 40° C. for a time period of at least about 2 minutes compared to an identical unit dose article comprising the water soluble film in the form of a pouch and not including the nonwoven web in the form of a pouch. In embodiments, the first compartment of the unit dose article prolongs the release of the first composition after contact with water at a temperature in the range of about 30° C. to 40° C. for a time period of at least about 3 minutes compared to an identical unit dose article comprising the water soluble film in the form of a pouch and not including the nonwoven web in the form of a pouch. In embodiments, the first compartment of the unit dose article prolongs the release of the first composition after contact with water at a temperature in the range of about 30° C. to 40° C. for a time period of at least about 4 minutes compared to an identical unit dose article comprising the water soluble film in the form of a pouch and not including the nonwoven web in the form of a pouch. In embodiments, the first compartment of the unit dose article prolongs the release of the first composition after contact with water at a temperature in the range of about 30° C. to 40° C. for a time period of at least about 5 minutes compared to an identical unit dose article comprising the water soluble film in the form of a pouch and not including the nonwoven web in the form of a pouch. In embodiments, the first compartment of the unit dose article prolongs the release of the first composition after contact with water at a temperature in the range of about 30° C. to 40° C. for a time period of at least about 7.5 minutes compared to an identical unit dose article comprising the water soluble film in the form of a pouch and not including the nonwoven web in the form of a pouch. In embodiments, the first compartment of the unit dose article prolongs the release of the first composition after contact with water at a temperature in the range of about 30° C. to 40° C. for a time period of at least about 10 minutes compared to an identical unit dose article comprising the water soluble film in the form of a pouch and not including the nonwoven web in the form of a pouch. In embodiments, the first compartment of the unit dose article prolongs the release of the first composition after contact with water at a temperature in the range of about 30° C. to 40° C. for a time period of at least about 12 minutes or more compared to an identical unit dose article comprising the water soluble film in the form of a pouch and not including the nonwoven web in the form of a pouch.

A unit dose article of the disclosure wherein the nonwoven is laminated to a film, can be designed to provide one or more advantages. For example, without intending to be bound by theory, the unit dose article of the disclosure can provide prolonged release of a liquid composition relative to a water soluble film pouch alone by creating a tortuous path for the composition(s) exiting and/or water entering the unit dose article while maintaining mechanical integrity, the unit dose article can include an increased gas barrier (e.g, to allow for a vacuum to be applied during thermoforming process or to prevent a composition contained therein from becoming stale) relative to a nonwoven web pouch alone, and/or the capability of holding liquids relative to a nonwoven web pouch alone.

All percentages, parts and ratios referred to herein are based upon the total dry weight of the fiber composition, nonwoven web composition, film composition, or total weight of the packet content composition of the present disclosure, as the case may be, and all measurements made are at about 25° C., unless otherwise specified. All percentages, parts and ratios referred to herein for liquid compositions are based upon the total weight of the liquid composition. All such weights as they pertain to listed ingredients are based on the active level and therefore do not include carriers or by-products that may be included in commercially available materials, unless otherwise specified.

All ranges set forth herein include all possible subsets of ranges and any combinations of such subset ranges. By default, ranges are inclusive of the stated endpoints, unless stated otherwise. Where a range of values is provided, it is understood that each intervening value between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also contemplated to be part of the disclosure.

It is expressly contemplated that for any number value described herein, e.g. as a parameter of the subject matter described or part of a range associated with the subject matter described, an alternative which forms part of the description is a functionally equivalent range surrounding the specific numerical value (e.g. for a dimension disclosed as "40 mm" an alternative embodiment contemplated is "about 40 mm").

As used herein and unless specified otherwise, the term "nonwoven web" refers to a web or sheet comprising, consisting of, or consisting essentially of fibers arranged (e.g., by a carding process) and bonded to each other. Further, as used herein, "nonwoven web" includes a nonwoven web or sheet. Methods of preparing nonwoven webs from fibers are well known in the art, for example, as described in Nonwoven Fabrics Handbook, prepared by Ian Butler, edited by Subhash Batra et al., Printing by Design, 1999, herein incorporated by reference in its entirety. As used herein and unless specified otherwise, the term "film" refers to a continuous film or sheet, e.g., prepared by a casting or extrusion process.

As used herein and unless specified otherwise, the term "water soluble" refers to any nonwoven web, film, or laminate having a dissolution time of 300 seconds or less at a specified temperature as determined according to MSTM-205 as set forth herein, or any fiber having a complete dissolution at a temperature of 40° C. according to the Method for Determining Single Fiber Solubility. For example, the dissolution time of the film, nonwoven web, or laminate optionally can be 200 seconds or less, 100 seconds or less, 60 seconds or less, or 30 seconds or less at a temperature of about 80° C., about 70° C., about 60° C., about 50° C., about 40° C., about 20° C., or about 10° C. according to MSTM-205. In embodiments, wherein the dissolution temperature is not specified, the nonwoven web, water soluble film, or laminate has a dissolution time of 300 seconds or less at a temperature no greater than about 80° C. In embodiments, "water soluble film" means that at a thickness of 1.5 mil, the film dissolves in 300 seconds or less at a temperature no greater than 80° C. according to MSTM-205. For example, a 1.5 mil (about 38 μm) thick water soluble film can have a dissolution time of 300 seconds or less, 200 seconds or less, 100 seconds or less, 60 seconds or less, or 30 seconds or less at a temperature of about 70° C., about 60° C., about 50° C., about 40° C., about 30° C., about 20° C., or about 10° C. according to MSTM-205.

As used herein and unless specified otherwise, the term "cold water soluble" refers to any nonwoven web, water soluble film, or laminate having a dissolution time of 300 seconds or less at a temperature in a range of about 10° C. to about 20° C. as determined according to MSTM-205, or fiber having a complete dissolution at a temperature in a range of about 10° C. to about 20° C. as determined according to the Method for Determining Single Fiber solubility. For example, the dissolution time of the film, nonwoven web, or laminate optionally can be 200 seconds or less, 100 seconds or less, 60 seconds or less, or 30 seconds at a temperature in a range of about 10° C. to about 20° C. according to MSTM-205. In embodiments, "cold water soluble film" means that at a thickness of 1.5 mil, the film dissolves in 300 seconds or less at a temperature no greater than 20° C. according to MSTM-205. For example, a 1.5 mil (about 38 μm) thick water soluble film can have a dissolution time of 300 seconds or less, 200 seconds or less, 100 seconds or less, 60 seconds or less, or 30 seconds or less at a temperature of about 20° C. or about 10° C. according to MSTM-205.

As used herein and unless specified otherwise, the term "hot water soluble" refers to any nonwoven web, water soluble film, or laminate having a dissolution time of 300 seconds or less at a temperature greater than about 20° C., for example in a range of about 21° C. to about 80° C., as determined according to MSTM-205, or fiber having a complete dissolution at a temperature of greater than about 20° C., for example in a range of about 21° C. to about 80° C. as determined according to the Method for Determining Single Fiber solubility. For example, the dissolution time of the film, nonwoven web, or laminate optionally can be 200 seconds or less, 100 seconds or less, 60 seconds or less, or 30 seconds at a temperature greater than about 20° C. according to MSTM-205, for example, in a range of about 21° C. to about 80° C., about 25° C. to about 80° C., about 25° C. to about 60° C., about 30° C. to about 60° C., about 25° C. to about 45° C., about 30° C. to about 45° C., or about 25° C. to about 43° C., about 30° C. to about 43° C., about 25° C. to about 40° C., or about 30° C. to about 40° C. In embodiments, "hot water soluble film" means that at a thickness of 1.5 mil, the film dissolves in 300 seconds or less at a temperature no less than about 21° C. according to MSTM-205. For example, a 1.5 mil (about 38 μm) thick water soluble film can have a dissolution time of 300 seconds or less, 200 seconds or less, 100 seconds or less, 60 seconds or less, or 30 seconds or less at a temperature of about 80° C., 70° C., about 60° C., about 50° C., about 40° C., about 30° C., about 25° C., or about 21° C. according to MSTM-205.

As used herein, the terms packet(s) and pouch(es) should be considered interchangeable. In certain embodiments, the terms packet(s) and pouch(es), respectively, are used to refer to a container made using the nonwoven web or the water soluble film, or both, and to a fully-sealed container preferably having a material sealed therein, e.g., in the form of a measured dose delivery system. The sealed pouches can be made from any suitable method, including such processes and features such as heat sealing, solvent welding, and adhesive sealing (e.g., with use of a water soluble adhesive).

As used herein, the terms resin(s) and polymer(s) should be considered interchangeable. In certain embodiments, the terms resin(s) and polymer(s), respectively are used to refer to a polymer optionally combined with one or more additional polymers, and to a single type of polymer, e.g., a resin can comprise more than one polymer.

As used herein and unless specified otherwise, the terms "wt. %" and "wt %" are intended to refer to the composition of the identified element in "dry" (non-water) parts by weight of the entire nonwoven web or water soluble film, including residual moisture in the nonwoven web or water soluble film, or parts by weight of the entire unit dose article or composition, as the case may be depending on context.

As used herein and unless specified otherwise, the term "PHR" ("phr") is intended to refer to the composition of the identified element in parts per one hundred parts water soluble polymer resin(s) (whether PVOH or other polymer resins, unless specified otherwise) in the nonwoven web or water soluble film, or a solution used to make the nonwoven web or water soluble film.

"Comprising" as used herein means that various components, ingredients or steps that can be conjointly employed in practicing the present disclosure. Accordingly, the term "comprising" encompasses the more restrictive terms "consisting essentially of" and "consisting of." The present compositions can comprise, consist essentially of, or consist of any of the required and optional elements disclosed herein. For example, a thermoformed packet can "consist essentially of" a nonwoven web described herein for use of its thermoforming characteristics, while including a non-thermoformed nonwoven web (e.g., lid portion), and optional markings on the nonwoven web, e.g. by inkjet printing. The disclosure illustratively disclosed herein suitably may be practiced in the absence of any element or step which is not specifically disclosed herein.

The unit dose articles, nonwoven webs, water soluble films, and related methods of making and use are contemplated to include embodiments including any combination of one or more of the additional optional elements, features, and steps further described below, unless stated otherwise.

In general, the unit dose article can include a nonwoven web and a water soluble film, wherein the nonwoven web can include a plurality of fibers including one or more water soluble fiber types, one or more non-water soluble fiber types, a blend of a water soluble fiber type and a non-water soluble fiber type, one or more water-soluble fiber forming materials, one or more non-water soluble fiber forming materials, or a blend of water soluble fiber forming materials and non-water soluble fiber forming materials. The water soluble film can include a water soluble resin, optionally including one or more water soluble polymers.

Water Soluble Film and Fiber Forming Materials

Water soluble polymers for use in the water soluble fibers, nonwoven webs, and water soluble films include, but are not limited to, a polyvinyl alcohol, polyacrylate, water-soluble acrylate copolymer, polyvinyl pyrrolidone, polyethyleneimine, pullulan, water-soluble natural polymers including, but not limited to, guar gum, gum Acacia, xanthan gum, carrageenan, and starch, water-soluble polymer derivatives including, but not limited to, modified starches, ethoxylated starch, and hydroxypropylated starch, copolymers of the forgoing and combinations of any of the foregoing. Yet other water-soluble polymers can include polyalkylene oxides, polyacrylamides, polyacrylic acids and salts thereof, celluloses, cellulose ethers, cellulose esters, cellulose amides, polyvinyl acetates, polycarboxylic acids and salts thereof, polyaminoacids, polyamides, gelatines, methylcelluloses, carboxymethylcelluloses and salts thereof, dextrins, ethylcelluloses, hydroxyethyl celluloses, hydroxypropyl methylcelluloses, maltodextrins, polymethacrylates, and combinations of any of the foregoing. Such water soluble polymers, whether PVOH or otherwise are commercially available from a variety of sources.

In general, the fibers of the disclosure and film of the disclosure can include polyvinyl alcohol. Polyvinyl alcohol is a synthetic polymer generally prepared by the alcoholysis, usually termed hydrolysis or saponification, of polyvinyl acetate. Fully hydrolyzed PVOH, where virtually all the acetate groups have been converted to alcohol groups, is a strongly hydrogen-bonded, highly crystalline polymer which dissolves only in hot water—greater than about 140° F. (about 60° C.). If a sufficient number of acetate groups are allowed to remain after the hydrolysis of polyvinyl acetate, that is the PVOH polymer is partially hydrolyzed, then the polymer is more weakly hydrogen-bonded, less crystalline, and is generally soluble in cold water—less than about 50° F. (about 10° C.). As such, the partially hydrolyzed polymer is a vinyl alcohol-vinyl acetate copolymer that is a PVOH copolymer, but is commonly referred to as PVOH.

The fibers and/or films described herein can include one or more polyvinyl alcohol (PVOH) homopolymers, one or more polyvinyl alcohol copolymers, or a combination thereof. As used herein, the term "homopolymer" generally includes polymers having a single type of monomeric repeating unit (e.g., a polymeric chain consisting of or consisting essentially of a single monomeric repeating unit). For the particular case of PVOH, the term "homopolymer" (or "PVOH homopolymer") further includes copolymers consisting of a distribution of vinyl alcohol monomer units and vinyl acetate monomer units, depending on the degree of hydrolysis (e.g., a polymeric chain consisting of or consisting essentially of vinyl alcohol and vinyl acetate monomer units). In the limiting case of 100% hydrolysis, a PVOH homopolymer can include a true homopolymer having only vinyl alcohol units. In some embodiments, the fibers and/or films of the disclosure include polyvinyl alcohol homopolymers. In some embodiments, the fibers and/or films of the disclosure include hot water soluble polyvinyl alcohol homopolymers.

In some embodiments, the polyvinyl alcohol includes a modified polyvinyl alcohol, for example, a copolymer. The modified polyvinyl alcohol can include a co-polymer or higher polymer (e.g., ter-polymer) including one or more monomers in addition to the vinyl acetate/vinyl alcohol groups. Optionally, the modification is neutral, e.g., provided by an ethylene, propylene, N-vinylpyrrolidone or other non-charged monomer species. Optionally, the modification is a cationic modification, e.g., provided by a positively charged monomer species. Optionally, the modification is an anionic modification. Thus, in some embodiments, the polyvinyl alcohol includes an anionic modified polyvinyl alcohol. An anionic modified polyvinyl alcohol can include a partially or fully hydrolyzed PVOH copolymer that includes an anionic monomer unit, a vinyl alcohol monomer unit, and optionally a vinyl acetate monomer unit (i.e., when not completely hydrolyzed). In some embodiments, the PVOH copolymer can include two or more types of anionic monomer units. General classes of anionic monomer units which can be used for the PVOH copolymer include the vinyl polymerization units corresponding to sulfonic acid vinyl monomers and their esters, monocarboxylic acid vinyl monomers, their esters and anhydrides, dicarboxylic monomers having a polymerizable double bond, their esters and anhydrides, and alkali metal salts of any of the foregoing. Examples of suitable anionic monomer units include the vinyl polymerization units corresponding to vinyl anionic monomers including vinyl acetic acid, maleic acid, monoalkyl maleate, dialkyl maleate, maleic anhydride, fumaric acid, monoalkyl fumarate, dialkyl fumarate, itaconic acid, monoalkyl itaconate, dialkyl itaconate, citraconic acid, monoalkyl citraconate, dialkyl citraconate, citraconic anhydride, mesaconic acid, monoalkyl mesaconate, dialkyl mesaconate, glutaconic acid, monoalkyl glutaconate, dialkyl glutaconate, alkyl acrylates, alkyl alkacrylates, vinyl sulfonic acid, allyl sulfonic acid, ethylene sulfonic acid, 2-acrylamido-1-methyl propane sulfonic acid, 2-acrylamide-2-methyl propanesulfonic acid, 2-methylacrylamido-2-methylpropanesulfonic acid (AMPS), 2-sulfoethyl acrylate, alkali metal salts of the foregoing (e.g., sodium, potassium, or other alkali metal salts), esters of the foregoing (e.g., methyl, ethyl, or other $C_1$-$C_4$ or $C_6$ alkyl esters), and combinations of the foregoing (e.g., multiple types of anionic monomers or equivalent forms of the same anionic monomer). In some embodiments, the PVOH copolymer can include two or more types of monomer units selected from neutral, anionic, and cationic monomer units.

The level of incorporation of the one or more anionic monomer units in the PVOH copolymers is not particularly limited. In embodiments, the one or more anionic monomer units are present in the PVOH copolymer in an amount in a range of about 1 mol. % or 2 mol. % to about 6 mol. % or 10 mol. % (e.g., at least 1.0, 1.5, 2.0, 2.5, 3.0, 3.5, or 4.0 mol. % and/or up to about 3.0, 4.0, 4.5, 5.0, 6.0, 8.0, or 10 mol. % in various embodiments).

Polyvinyl alcohols can be subject to changes in solubility characteristics. The acetate group in the co-poly(vinyl acetate vinyl alcohol) polymer (PVOH homopolymer) is known by those skilled in the art to be hydrolysable by either acid or alkaline hydrolysis. As the degree of hydrolysis increases, a polymer composition made from the PVOH homopolymer will have increased mechanical strength but reduced solubility at lower temperatures (e.g., requiring hot water temperatures for complete dissolution). Accordingly, exposure of a PVOH homopolymer to an alkaline environment (e.g., resulting from a laundry bleaching additive) can transform the polymer from one which dissolves rapidly and entirely in a given aqueous environment (e.g., a cold water medium) to one which dissolves slowly and/or incompletely in the aqueous environment, potentially resulting in undissolved polymeric residue.

The degree of hydrolysis (DH) of the PVOH homopolymers and PVOH copolymers included in the water-soluble fibers and films of the present disclosure can be in a range of about 75% to about 99.9% (e.g., about 79% to about 92%, about 75% to about 89%, about 80% to about 90%, about 88% to 92%, about 86.5% to about 89%, or about 88%, 90% or 92% such as for cold-water soluble compositions; about 90% to about 99.9%, about 90% to about 99% about 92% to about 99%, about 95% to about 99%, about 98% to about 99%, about 98% to about 99.9%, about 96%, about 98%, about 99%, or greater than 99%). As the degree of hydrolysis is reduced, a fiber or film made from the polymer will have reduced mechanical strength but faster solubility at temperatures below about 20° C. As the degree of hydrolysis increases, a fiber or film made from the polymer will tend to be mechanically stronger and the thermoformability will tend to decrease. The degree of hydrolysis of the PVOH can be chosen such that the water-solubility of the polymer is temperature dependent, and thus the solubility of a film or fiber made from the polymer and additional ingredients is also influenced. In one option the film and/or fibers are cold water-soluble. For a co-poly(vinyl acetate vinyl alcohol) polymer that does not include any other monomers (e.g., a homopolymer not copolymerized with an anionic monomer) a cold water-soluble fiber or film, soluble in water at a temperature of less than 10° C., can include PVOH with a degree of hydrolysis in a range of about 75% to about 90%, about 75% to about 89%, or in a range of about 80% to about 90%, or in a range of about 85% to about 90%. In another option the fiber or film is hot water-soluble. For a co-poly (vinyl acetate vinyl alcohol) polymer that does not include any other monomers (e.g., a homopolymer not copolymerized with an anionic monomer) a hot water-soluble fiber or film that is soluble in water at a temperature of at least about 60° C., can include PVOH with a degree of hydrolysis of at least about 98%. In embodiments, one of more of the plurality of fibers comprises a polyvinyl alcohol polymer having a degree of hydrolysis in a range of about 75% to about 99.9%. In embodiments, one or more of the plurality of fibers comprises a polyvinyl alcohol polymer having a degree of hydrolysis in a range of about 75% to about 98%. In embodiments, one of more of the plurality of fibers comprises a polyvinyl alcohol polymer having a degree of hydrolysis in a range of about 75% to about 89%. In embodiments, one of more of the plurality of fibers comprises a polyvinyl alcohol polymer having a degree of hydrolysis in a range of about 90% to about 99.9%. In embodiments, the water soluble film comprises a polyvinyl alcohol homopolymer or a PVOH copolymer having a degree of hydrolysis in a range of about 75% to about 99.9%. In embodiments, the water soluble film comprises a polyvinyl alcohol homopolymer or a polyvinyl alcohol copolymer having a degree of hydrolysis in a range of about 75% to about 98%.

The degree of hydrolysis of a polymer blend can also be characterized by the arithmetic weighted, average degree of hydrolysis ($\overline{H^{\circ}}$). For example, $\overline{H^{\circ}}$ for a PVOH polymer that includes two or more PVOH polymers is calculated by the formula $\overline{H^{\circ}}=\Sigma(W_i \bullet H_i)$ where $W_i$ is the weight percentage of the respective PVOH polymer and $H_i$ is the respective degrees of hydrolysis. When a polymer is referred to as having (or not having) a specific degree of hydrolysis, the polymer can be a single polyvinyl alcohol polymer having the specified degree of hydrolysis or a blend of polyvinyl alcohol polymers having an average degree of hydrolysis as specified.

The viscosity of a PVOH polymer (μ) is determined by measuring a freshly made solution using a Brookfield LV type viscometer with UL adapter as described in British Standard EN ISO 15023-2:2006 Annex E Brookfield Test method. It is international practice to state the viscosity of 4% aqueous polyvinyl alcohol solutions at 20° C. All viscosities specified herein in Centipoise (cP) should be understood to refer to the viscosity of 4% aqueous polyvinyl alcohol solution at 20° C., unless specified otherwise. Similarly, when a polymer is described as having (or not having) a particular viscosity, unless specified otherwise, it is intended that the specified viscosity is the average viscosity for the polymer, which inherently has a corresponding molecular weight distribution, i.e. the weighted natural log average viscosity. It is well known in the art that the viscosity of PVOH polymers is correlated with the weight average molecular weight ($\overline{M}$w) of the PVOH polymer, and often the viscosity is used as a proxy for the $\overline{M}$w.

In embodiments, the PVOH resin may have a viscosity of about 1.0 to about 50.0 cP, about 1.0 to about 40.0 cP, or about 1.0 to about 30.0 cP, for example about 4 cP, 8 cP, 15 cP, 18 cP, 23 cP, or 26 cP. In embodiments, the PVOH homopolymers and/or copolymers may have a viscosity of about 1.0 to about 40.0 cP, or about 5 cPs to about 23 cP, for example, about 1 cP, 1.5 cP, 2 cP, 2.5 cP, 3 cP, 3.5 cP, 4 cP, 4.5 cP, 5 cP, 5.5 cP, 6 cP, 6.5 cP, 7 cP, 7.5 cP, 8 cP, 8.5 cP, 9 cP, 9.5 cP, 10 cP, 11 cP, 12 cP, 13 cP, 14 cP, 15 cP, 17.5 cP, 18 cP, 19 cP, 20 cP, 21 cP, 22 cP, 23 cP, 24 cP, 25 cP, 26 cP, 27 cP, 28 cP, 29 cP, 30 cP, 31 cP, 32 cP, 33 cP, 34 cP, 35 cP, or 40 cP. In embodiments, the PVOH homopolymers and/or copolymers may have a viscosity of about 21 cP to 26 cP. In embodiments, the PVOH homopolymers and/or copolymers can have a viscosity of about 5 cP to about 14 cP. In embodiments, the PVOH homopolymers and/or copolymers can have a viscosity of about 5 cP to about 23 cP.

The water-soluble polymers, whether polyvinyl alcohol polymers or otherwise, can be blended. When the polymer blend includes a blend of polyvinyl alcohol polymers, the PVOH polymer blend can include a first PVOH polymer ("first PVOH polymer") which can include a PVOH homopolymer or a PVOH copolymer including one or more types of anionic monomer units (e.g., a PVOH ter- (or higher co-) polymer) and a second PVOH polymer ("second PVOH polymer") which can include a PVOH homopolymer or a PVOH copolymer including one or more types of anionic monomer units (e.g., a PVOH ter- (or higher co-) polymer).

In some aspects, the PVOH polymer blend includes only the first PVOH polymer and the second PVOH polymer (e.g., a binary blend of the two polymers). Alternatively, or additionally, the PVOH polymer blend or a fiber or film made therefrom can be characterized as being free or substantially free from other polymers (e.g., other water-soluble polymers generally, other PVOH-based polymers specifically, or both). As used herein, "substantially free" means that the first and second PVOH polymers make up at least 95 wt. %, at least 97 wt. %, or at least 99 wt. % of the total amount of water-soluble polymers in the water-soluble fiber or film. In other aspects, the water-soluble fiber or film can include one or more additional water-soluble polymers. For example, the PVOH polymer blend can include a third PVOH polymer, a fourth PVOH polymer, a fifth PVOH polymer, etc. (e.g., one or more additional PVOH homopolymers or PVOH copolymers, with or without anionic monomer units). For example, the water-soluble film can include at least a third (or fourth, fifth, etc.) water-soluble polymer which is other than a PVOH polymer (e.g., other than PVOH homopolymers or PVOH copolymers, with or without anionic monomer units).

Biodegradability

Polyvinyl alcohol polymers are generally biodegradable as they decompose in the presence of water and enzymes under aerobic, anaerobic, soil, and compost conditions. In general, as the degree of hydrolysis of a polyvinyl alcohol polymer increases up to about 80%, the biodegradation activity of the polyvinyl alcohol polymer increases. Without intending to be bound by theory, it is believed that increasing the degree of hydrolysis above 80% does not appreciably affect biodegradability. Additionally, the stereoregularity of the hydroxyl groups of polyvinyl alcohol polymers has a large effect on the biodegradability activity level and the more isotactic the hydroxyl groups of the polymer sequence, the higher the degradation activity becomes. Without intending to be bound by theory, for soil and/or compost biodegradation it is believed that a nonwoven web prepared from a polyvinyl alcohol fiber will have higher biodegradation activity levels relative to a water soluble film prepared from a similar polyvinyl alcohol polymer, due to the increase in the polymer surface area provided by the nonwoven web, relative to a film. Further, without intending to be bound by theory, it is believed that while the degree of polymerization of the polyvinyl alcohol polymer has little to no effect on the biodegradability of a film or nonwoven web prepared with the polymer, the polymerization temperature may have an effect on the biodegradability of a film or nonwoven because the polymerization temperature can affect the crystallinity and aggregating status of a polymer. In particular as the crystallinity decreases, the polymer chain hydroxyl groups become less aligned in the polymer structure and the polymer chains become more disordered allowing for chains to accumulate as amorphous aggregates, thereby decreasing availability of ordered polymer structures such that the biodegradation activity is expected to decrease for soil and/or compost biodegradation mechanisms wherein the polymer is not dissolved. Without intending to be bound by theory, it is believed that because the stereoregularity of the hydroxyl groups of polyvinyl alcohol polymers has a large effect on biodegradability activity levels, the substitution of functionalities other than hydroxyl groups (e.g., anionic AMPS functional groups, carboxylate groups, or lactone groups) is expected to decrease the biodegradability activity level, relative to a polyvinyl alcohol homopolymer having the same degree of hydrolysis, unless the functional group itself is also biodegradable, in which case biodegradability of the polymer can be increased with substitution. Further, it is believed that while the biodegradability activity level of a substituted polyvinyl alcohol can be less than that of the corresponding homopolymer, the substituted polyvinyl alcohol will still exhibit biodegradability.

Methods of determining biodegradation activity are known in the art, for example, as described in Chiellini et al., Progress in Polymer Science, Volume 28, Issue 6, 2003, pp. 963-1014, which is incorporated herein by reference in its entirety. Further methods and standards can be found in ECHA's Annex XV Restriction Report—Microplastics, Version number 1, Jan. 11, 2019, which is incorporated herein by reference in its entirety. Suitable standards include OECD 301B (ready biodegradation), OECD 301B (enhanced biodegradation), OECD 302B (inherent biodegradation), OECD 311 (anaerobic), and ASTM D5988 (soil).

In embodiments, the fibers described herein can be of the standard ready biodegradation or enhanced degradation. As used herein, the term "ready biodegradation" refers to a standard that is met if the material (e.g., a fiber) reached 60% biodegradation (mineralization) within 28 days of the beginning of the test, according to the OECD 301B test as described in said ECHA's Annex XV. As used herein, the term "enhanced biodegradation" refers to a standard that is met if the material (e.g., a fiber) reaches 60% biodegradation within 60 days from the beginning of the test, according to the OECD 301B test as described in said ECHA's Annex XV. In embodiments, the fibers herein meet the standards of ready biodegradation. In embodiments, the films herein meet the standards of ready biodegradation or enhanced degradation. In embodiments, the laminate (nonwoven and film) as used herein meet the standards of ready biodegradation or enhanced biodegradation.

Auxiliary Agents

In general, along with the film and/or fiber forming material, the fibers, nonwoven webs, and/or water soluble films of the disclosure can include auxiliary agents such as, but not limited to, plasticizers, plasticizer compatibilizers, surfactants, lubricants, release agents, fillers, extenders, cross-linking agents, antiblocking agents, antioxidants, detackifying agents, antifoams, nanoparticles such as layered silicate-type nanoclays (e.g., sodium montmorillonite), bleaching agents (e.g., sodium metabisulfite, sodium bisulfite or others), aversive agents such as bitterants (e.g., denatonium salts such as denatonium benzoate, denatonium saccharide, and denatonium chloride; sucrose octaacetate; quinine; flavonoids such as quercetin and naringen; and quassinoids such as quassin and brucine) and pungents (e.g., capsaicin, piperine, allyl isothiocyanate, and resinferatoxin), and other functional ingredients, in amounts suitable for their intended purposes. As used herein and unless specified otherwise, "auxiliary agents" include secondary additives, processing agents, and active agents. Specific such auxiliary agents can be selected from those suitable for use in water-soluble fibers, non-water soluble fibers, nonwoven webs, or those suitable for use in water-soluble films.

In embodiments, the fibers and/or films can be free of auxiliary agents. As used herein and unless specified otherwise, "free of auxiliary agents" with respect to the fiber means that the fiber includes less than about 0.01 wt %, less than about 0.005 wt. %, or less than about 0.001 wt. % of auxiliary agents, based on the total weight of the fiber. As used herein and unless specified otherwise, "free of auxiliary agents" with respect to the film or nonwoven web means that the nonwoven web includes less than about 0.01 wt %, less than about 0.005 wt. %, or less than about 0.001 wt. % of auxiliary agents, based on the total weight of the film or nonwoven web. In embodiments, the water soluble fibers comprise a plasticizer. In embodiments, the water soluble fibers comprise a surfactant. In embodiments, the non-water soluble fibers comprise a plasticizer. In embodiments, the non-water soluble fibers comprise a surfactant. In embodiments, the nonwoven web includes a plasticizer. In embodiments, the nonwoven web includes a surfactant.

A plasticizer is a liquid, solid, or semi-solid that is added to a material (usually a resin or elastomer) making that material softer, more flexible (by decreasing the glass-transition temperature of the polymer), and easier to process. A polymer can alternatively be internally plasticized by chemically modifying the polymer or monomer. In addition or in the alternative, a polymer can be externally plasticized by the addition of a suitable plasticizing agent. Water is recognized as a very efficient plasticizer for PVOH and other polymers; including but not limited to water soluble polymers, however, the volatility of water makes its utility limited since polymer films need to have at least some resistance (robustness) to a variety of ambient conditions including low and high relative humidity.

The plasticizer can include, but is not limited to, glycerin, diglycerin, sorbitol, xylitol, maltitol, ethylene glycol, diethylene glycol, triethylene glycol, dipropylene glycol, tetraethylene glycol, propylene glycol, polyethylene glycols up to 1000 MW, neopentyl glycol, trimethylolpropane, polyether polyols, sorbitol, 2-methyl-1,3-propanediol (MP-Diol®), ethanolamines, and a mixture thereof.

Surfactants for use in films are well known in the art and can suitably be used in the fibers, films, and/or compositions of the disclosure. Optionally, surfactants are included to aid in the dispersion of the fibers during carding. Optionally, surfactants are included as cleaning aids for the personal care composition. Suitable surfactants can include the nonionic, cationic, anionic and zwitterionic classes. Suitable surfactants include, but are not limited to, propylene glycols, diethylene glycols, monoethanolamine, polyoxyethylenated polyoxypropylene glycols, alcohol ethoxylates, alkylphenol ethoxylates, tertiary acetylenic glycols and alkanolamides (nonionics), polyoxyethylenated amines, quaternary ammonium salts and quaternized polyoxyethylenated amines (cationics), alkali metal salts of higher fatty acids containing about 8 to 24 carbon atoms, alkyl sulfates, alkyl polyethoxylate sulfates and alkylbenzene sulfonates (anionics), and amine oxides, N-alkylbetaines and sulfobetaines (zwitterionics). Other suitable surfactants include dioctyl sodium sulfosuccinate, lactylated fatty acid esters of glycerin and propylene glycol, lactylic esters of fatty acids, sodium alkyl sulfates, polysorbate 20, polysorbate 60, polysorbate 65, polysorbate 80, lecithin, acetylated fatty acid esters of glycerin and propylene glycol, and odium lauryl sulfate, acetylated esters of fatty acids, myristyl dimethylamine oxide, trimethyl tallow alkyl ammonium chloride, quaternary ammonium compounds, alkali metal salts of higher fatty acids containing about 8 to 24 carbon atoms, alkyl sulfates, alkyl polyethoxylate sulfates, alkylbenzene sulfonates, monoethanolamine, lauryl alcohol ethoxylate, propylene glycol, diethylene glycol, sodium cocoyl isethionate, sodium lauryl sulfate, glucotain, phoenamids, cola lipid, cocamides, such as cocamide ethanolamines, ethylene oxide based surfactants, saponified oils of avocado and palm, salts thereof and combinations of any of the foregoing. In embodiments, the surfactant comprises a cocamide. Without intending to be bound by theory, it is believed that a cocamide can aid in foam formation, enhancing the foaming experience of an article comprising a personal care composition. In various embodiments, the amount of surfactant in the fiber is in a range of about 0.01 wt. % to about 10 wt. %, about 0.1 wt. % to about 5 wt. %, about 1.0 wt. % to about 2.5 wt. %, about 0.01 wt % to about 1.5 wt %, about 0.1 wt % to about 1 wt %, about 0.01 wt % to 0.25 wt %, or about 0.10 wt % to 0.20 wt %. In various embodiments, the amount of surfactant in a personal care composition contained within the pouch can be in a range of about 5 wt % to about 50 wt %, about 10 wt % to about 45 wt %, or about 10 wt % to about 40 wt %.

In embodiments, the nonwoven webs and/or films of the disclosure can further comprise auxiliary agents such as one or more auxiliary agents in the group of: an exfoliant (chemical exfoliants and mechanical exfoliants), a fragrance and/or perfume microcapsule, an aversive agent, a surfactant, a colorant, an enzyme, a skin conditioner, a de-oiling agent, and a cosmetic agent.

In embodiments, an auxiliary agent is provided in or on one or more of the group of the nonwoven web, the plurality of fibers, and the water soluble film. In embodiments, a personal care composition is provided on or in one or more of the group of the nonwoven web, the plurality of fibers, and the water soluble film. In embodiments, one or more auxiliary agents can be provided on the surface of the nonwoven web. In embodiments, one or more auxiliary agents can be dispersed among the fibers of the nonwoven web. In embodiments, one or more auxiliary agents can be dispersed on a face of the nonwoven web. In embodiments, one or more auxiliary agents can be dispersed in the fibers. In embodiments, one or more auxiliary agents can be dispersed on the fibers. In embodiments, one or more auxiliary agents can be provided on a face of the water soluble film. In embodiments, one or more auxiliary agents can be dispersed within the water soluble film. In embodiments, the nonwoven web in the form of a pouch has an exterior face facing away from the interior pouch volume, and a personal care composition is provided on the exterior face. In embodiments, the nonwoven web in the form of a pouch has an exterior face facing away from the interior pouch volume, and one or more auxiliary agentsis provided on the exterior face.

The chemical exfoliants, mechanical exfoliants, fragrances and/or perfume microcapsules, aversive agents, surfactants, colorants, proteins, peptides, enzymes, skin conditioners, de-oiling agents, cosmetic agents, or a combination thereof, when present, can be provided in an amount of at least about 1 wt %, or in a range of about 1 wt % to about 99 wt % based on the weight of the polymeric mixture (e.g., fiber forming material or film forming material). In embodiments, the chemical exfoliants, mechanical exfoliants, fragrances and/or perfume microcapsules, aversive agents, surfactants, colorants, enzymes, skin conditioners, de-oiling agents, and/or cosmetic agents can be provided in an amount sufficient to provide additional functionality to the fiber and/or film, such as exfoliation of human skin. The chemical exfoliants, mechanical exfoliants, fragrances and/or perfume microcapsules, aversive agents, surfactants, colorants, enzymes, skin conditioners, de-oiling agents, cosmetic agents, or a combination thereof, can take any desired form, including as a solid (e.g., powder, granulate, crystal, flake, or ribbon), a liquid, a mull, a paste, a gas, etc., and optionally can be encapsulated, such as microcapsules.

In certain embodiments, the nonwoven web and/or film can comprise an enzyme. Suitable enzymes include enzymes categorized in any one of the six conventional Enzyme Commission (EC) categories, i.e., the oxidoreductases of EC 1 (which catalyze oxidation/reduction reactions), the transferases of EC 2 (which transfer a functional group, e.g., a methyl or phosphate group), the hydrolases of EC 3 (which catalyze the hydrolysis of various bonds), the lyases of EC 4 (which cleave various bonds by means other than hydrolysis and oxidation), the isomerases of EC 5 (which catalyze isomerization changes within a molecule) and the ligases of EC 6 (which join two molecules with covalent bonds). Examples of such enzymes include dehydrogenases and oxidases in EC 1, transaminases and kinases in EC 2, lipases, cellulases, amylases, mannanases, and peptidases (a.k.a. proteases or proteolytic enzymes) in EC 3, decarboxylases in EC 4, isomerases and mutases in EC 5 and synthetases and synthases of EC 6. Suitable enzymes from each category are described in, for example, U.S. Pat. No. 9,394,092, the entire disclosure of which is herein incorporated by reference. In certain embodiments, enzymes can include bromeline (pineapple extract), papain (papaya), ficin (fig), actinidin (kiwi), hyaluronidase, lipase, peroxidase, superoxide dismutase, tyrosinase, alkaline phosphatase, or a combination thereof. In embodiments, the enzyme can be encapsulated in the form of, for example, nanoemulsions, nanocapsules, granules or a combination thereof.

Enzymes for use in laundry and dishwashing applications can include one or more of protease, amylase, lipase, dehydrogenase, transaminase, kinase, cellulase, mannanase, peptidase, decarboxylase, isomerase, mutase, synthetase, synthase, and oxido-reductase enzymes, including oxido-reductase enzymes that catalyze the formation of bleaching agents.

It is contemplated that an enzyme for use herein can come from any suitable source or combination of sources, for example bacterial, fungal, plant, or animal sources. In one type of embodiment, a mixture of two or more enzymes will come from at least two different types of sources. For example, a mixture of protease and lipase can come from a bacterial (protease) and fungal (lipase) sources.

Optionally, an enzyme for use herein, including but not limited to any enzyme class or member described herein, is one which works in alkaline pH conditions, e.g. a pH in a range of about 8 to about 11. Optionally, an enzyme for use herein, including but not limited to any enzyme class or member described herein, is one which works in a temperature in a range of about 5° C. to about 45° C.

In embodiments, the nonwoven web and/or film can comprise a protein and/or peptide. Suitable proteins and/or peptides can include, but are not limited to, collagen and/or collagen peptides, or amino acids, for example, aspartic acid, glutamic acid, serine, histidine, glycine, threonine, arginine, alanine, tyrosine, cysteine, valine, methionine, phenylalanine, isoleucine, leucine, lysine, hydroxyproline, or proline.

In embodiments, the nonwoven web and/or film can comprise a colorant. Suitable colorants can include an indicator dye, such as a pH indicator (e.g., thymol blue, bromothymol, thymolphthalein, and thymolphthalein), a moisture/water indicator (e.g., hydrochromic inks or leuco dyes), or a thermochromic ink, wherein the ink changes color when temperature increases and/or decreases. Suitable colorants include, but are not limited to a triphenylmethane dye, an azo dye, an anthraquinone dye, a perylene dye, an indigoid dye, a food, drug and cosmetic (FD&C) colorant, an organic pigment, an inorganic pigment, or a combination thereof. Examples of colorants include, but are not limited to, FD&C Red #40; Red #3; FD&C Black #3; Black #2; Mica-based pearlescent pigment; FD&C Yellow #6; Green #3; Blue #1; Blue #2; titanium dioxide (food grade); brilliant black; and a combination thereof. Other examples of suitable colorants can be found in U.S. Pat. No. 5,002,789, hereby incorporated by reference in its entirety.

Another class of embodiments can include one or more fragrances in the nonwoven webs and/or films of the disclosure. As used herein, the term fragrance refers to any applicable material that is sufficiently volatile to produce a scent. Embodiments including fragrances can include fragrances that are scents pleasurable to humans, or alternatively fragrances that are scents repellant to humans, animals, and/or insects. Suitable fragrances include, but are not limited to, fruits including, but not limited to, lemon, apple, cherry, grape, pear, pineapple, orange, strawberry, raspberry, musk and flower scents including, but not limited to, lavender-like, rose-like, iris-like and carnation-like. Optionally the fragrance is one which is not also a flavoring. Other fragrances include herbal scents including, but not limited to, rosemary, thyme, and sage; and woodland scents derived from pine, spruce and other forest smells. Fragrances may also be derived from various oils, including, but not limited to, essential oils, or from plant materials including, but not limited to, peppermint, spearmint and the like. Suitable fragrant oils can be found in U.S. Pat. No. 6,458,754, hereby incorporated by reference in its entirety. Suitable fragrant oils include, but are not limited to, 4-(2,2,6-trimethylcyclohex-1-enyl)-2-en-4-one, acetaldehyde phenyletheyl propyl acetal, 2,6,10-trimethyl-9-undecenal, hexanoic acid 2-propenyl ester, 1-octen-3-ol, trans-anethole, iso buthyl (z)-2-methyl-2-butenoate, anisaldehyde diethyl acetal, 3-methyl-5-propyl-cyclohezen-1-one, 2,4-dimethyl-3-cyclohexene-1-carbaldehyde, trans-4-decenal, decanal, 2-pentylcyclopentanone, ethyl anthranilate, eugenol, 3-(3-isopropylphenyl)butanoal, methyl 2-octynoate, isoeugenol, cis-3-hexenyl methyl carbonate, linalool, methyl-2-nonynonate, benzoic acid 2-hydroxymethyl ester, nonal, octanal, 2-nonennitrile, 4-nonanolide, 9-decen-1-ol, and 10-undecen-1-al. Applicable fragrances can also be found in U.S. Pat. Nos. 4,534,981, 5,112,688, 5,145,842, 6,844,302 and Perfumes Cosmetics and Soaps, Second Edition, edited by W. A. Poucher, 1959, all hereby incorporated by reference in their entireties. These fragrances include acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchids, reseda, sweet pea, trefle, tuberose, vanilla, violet, wallflower, and the like.

Fragrances can include perfumes. The perfume may comprise neat perfume, encapsulated perfume, or mixtures thereof. Preferably, the perfume includes neat perfume. A portion of the perfume may be encapsulated in a core-shell encapsulate. In another type of embodiment, the perfume will not be encapsulated in a core/shell encapsulate.

As used herein, the term "perfume" encompasses the perfume raw materials (PRMs) and perfume accords. The term "perfume raw material" as used herein refers to compounds having a molecular weight of at least about 100 g/mol and which are useful in imparting an odor, fragrance, essence or scent, either alone or with other perfume raw materials. As used herein, the terms "perfume ingredient" and "perfume raw material" are interchangeable. The term "accord" as used herein refers to a mixture of two or more PRMs. In embodiments, any of the perfume accords, perfume raw materials, or fragrances can be encompassed in a microcapsule, termed "perfume microcapsules" as used herein.

Typical PRM comprise inter alia alcohols, ketones, aldehydes, esters, ethers, nitrites and alkenes, such as terpene. A listing of common PRMs can be found in various reference sources, for example, "Perfume and Flavor Chemicals", Vols. I and II; Steffen Arctander Allured Pub. Co. (1994) and "Perfumes: Art, Science and Technology", Miller, P. M. and Lamparsky, D., Blackie Academic and Professional (1994). The PRMs are characterized by their boiling points (B.P.) measured at the normal pressure (760 mm Hg), and their octanol/water partitioning coefficient (P). Based on these characteristics, the PRMS may be categorized as Quadrant I, Quadrant II, Quadrant III, or Quadrant IV perfumes.

In embodiments, the nonwoven web and/or film can include an exfoliant. In embodiments, the exfoliant can comprise a chemical exfoliant or a mechanical exfoliant. Suitable mechanical exfoliants for use herein can include, but are not limited to, apricot shells, sugar, oatmeal, salt, silica, diatomaceous earth, clay, aluminum hydrates, PVOH microbeads, pumice or a combination thereof. Suitable chemical exfoliants for use herein can include, but are not limited to, alpha hydroxyl acid, beta hydroxyl acid, enzyme, salicylic acid, glycolic acid, citric acid, malic acid, or a combination thereof.

In certain embodiments, the aversive agents, surfactants, colorants, enzymes, skin conditioners, de-oiling agents, cosmetic agents, or a combination thereof, are encapsulated, allowing for controlled release. Suitable microcapsules can include or be made from one or more of melamine formaldehyde, polyurethane, urea formaldehyde, chitosan, polymethyl methacrylate, polystyrene, polysulfone, poly tetrahydrofuran, gelatin, gum arabic, starch, polyvinyl pyrrolidone, carboxymethylcellulose, hydroxyethylcellulose, methylcellulose, arabinogalactan, polyvinyl alcohol, polyacrylic acid, ethylcellulose, polyethylene, polymethacrylate, polyimide, poly (ethylenevinyl acetate), cellulose nitrate, silicones, poly(lactideco-glycolide), paraffin, carnauba, spermaceti, beeswax, stearic acid, stearyl alcohol, glyceryl stearates, shellac, cellulose acetate phthalate, zein, and combinations thereof. In one type of embodiment, the microcapsule is characterized by a mean particle size (e.g. Dv50) of at least about 0.1 micron, or in a range of about 0.1 micron to about 200 microns, for example. In alternate embodiments, the microcapsules can form agglomerates of individual particles, for example wherein the individual particles have a mean particle size of at least about 0.1 micron, or in a range of about 0.1 micron to about 200 microns.

Water Soluble Fibers

Water soluble fibers generally include fibers and/or fiber forming materials made of any material that, when provided as the sole resin in a film or sole fiber forming material in a nonwoven, the film or nonwoven dissolves in 300 seconds or less at temperatures of 80° C. or less, as determined by MSTM-205. The water soluble fibers can include a single water soluble polymer or a blend of water soluble polymers. Suitable water soluble polymers include, but are not limited to, polyvinyl alcohol homopolymer, polyvinyl alcohol copolymer, polyacrylate, water-soluble acrylate copolymer, polyvinyl pyrrolidone, polyethyleneimine, pullulan, water-soluble natural polymer including, but not limited to, guar gum, gum Acacia, xanthan gum, carrageenan, and starch, water-soluble polymer derivatives including, but not limited to, modified starches, ethoxylated starch, and hydroxypropylated starch, copolymers of the forgoing and combinations of any of the foregoing. Yet other water soluble fibers can include polyalkylene oxides, polyacrylamides, polyacrylic acids and salts thereof, celluloses, cellulose ethers, cellulose esters, cellulose amides, polyvinyl acetates, polycarboxylic acids and salts thereof, polyaminoacids, polyamides, gelatines, methylcelluloses, carboxymethylcelluloses and salts thereof, dextrins, ethylcelluloses, hydroxyethyl celluloses, hydroxypropyl methylcelluloses, maltodextrins, polymethacrylates, and combinations of any of the foregoing. In embodiments, the water soluble fibers can include a PVOH homopolymer fiber forming material, PVOH copolymer fiber forming material, or a combination thereof. In embodiments, the water soluble fibers can comprise a sole PVOH homopolymer fiber forming material or a blend of PVOH homopolymer fiber forming materials. In embodiments, the water soluble fibers can comprise a hot water soluble PVOH homopolymer fiber forming material. In further embodiments, the water soluble fibers can comprise a PVOH homopolymer fiber forming material with a viscosity in a range of 5 cP to 23 cP and a degree of hydrolysis in a range of 86% to 92%.

In embodiments, the water soluble fibers can include an auxiliary agent as described above. In embodiments, the water soluble fibers can be substantially free of auxiliary agents as described above. In embodiments, the water soluble fibers can include a plasticizer as described above. The total amount of the non-water plasticizer provided in the water soluble fiber can be in a range of about 1 wt. % to about 45 wt. %, or about 5 wt. % to about 45 wt. %, or about 10 wt. % to about 40 wt. %, or about 20 wt. % to about 30 wt. %, about 1 wt. % to about 4 wt. %, or about 1.5 wt. % to about 3.5 wt. %, or about 2.0 wt. % to about 3.0 wt. %, for example about 1 wt. %, about 2.5 wt. %, about 5 wt. %, about 10 wt. %, about 15 wt. %, about 20 wt. %, about 25 wt. %, about 30 wt. %, about 35 wt. %, or about 40 wt. %, based on total fiber weight. In embodiments, the water soluble fibers comprise glycerin, sorbitol, or a combination thereof. In embodiments, the water soluble fibers comprise glycerin. In embodiments, the water soluble fibers comprise sorbitol. In certain embodiments, the water soluble fibers can include glycerin, for example in about 10 wt % based on total fiber weight, and sorbitol, for example in about 5 wt % based on the total fiber weight.

In embodiments, the water soluble fibers can include a surfactant as described above. In various embodiments, the amount of surfactant in the water soluble fiber is in a range of about 0.01 wt. %, to about 2.5 wt. %, about 0.1 wt. % to about 2.5 wt. %, about 1.0 wt. % to about 2.0 wt. %, about 0.01 wt % to 0.25 wt %, or about 0.10 wt % to 0.20 wt %. The water soluble fibers can include a surfactant such as one or more cocamide, for example a cocamide ethanolamine. In embodiments, the cocamide can comprise cocamide diethanolamine, cocamide monoethanolamine, or a combination thereof. The cocaminde can be used in cosmetic personal care unit dose articles, and can provide various advantages such as a prolonged dissolution profile due to the fatty acid chain on the molecule.

In embodiments, any of the auxiliary agents disclosed herein can be added to the fibers of the disclosure. In refinements of the forgoing embodiment, the auxiliary agents can be added to the fiber forming material prior to formation of the fiber such that the auxiliary agents are dispersed in the fiber. In addition and/or in the alternative, auxiliary agents can be added to the surface of a fiber after fiber formation (e.g., dispersed on the fibers).

When included in the water soluble fiber, a colorant can be provided in an amount of 0.01% to 25% by weight of the polymer mixture, such as, 0.02%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, and 24% by weight of the polymer mixture.

Non-Water Soluble Fibers

Non-water soluble fibers generally include fibers and/or fiber forming materials made of any material that, when provided in a film as the sole film forming material or provided in a nonwoven web as the sole fiber forming material, the film and/or nonwoven web does not dissolve in 300 seconds or less at temperatures of 80° C. or less, as determined by MSTM-205. The non-water soluble fibers can include a sole non-water soluble polymer fiber forming material or a blend of non-water soluble polymer fiber forming materials. Suitable non-water soluble fibers and/or non-water soluble fiber forming materials include, but are not limited to, cotton, polyester, polyethylene (e.g., high density polyethylene and low density polyethylene), polypropylene, wood pulp, fluff pulp, abaca, viscose, polylactic acid, polyester, nylon 6, insoluble cellulose, insoluble starch, hemp, jute, flax, ramie, sisal, bagasse, banana fiber, lacebark, silk, sinew, catgut, wool, sea silk, mohair, angora, cashmere, collagen, actin, nylon, dacron, rayon, bamboo fiber, modal, diacetate fiber, triacetate fiber, and combinations thereof. In embodiments, the non-water soluble fiber forming material and/or non-water soluble fibers comprise one or more of the group of: cotton, hemp, jute, flax, ramie, sisal, bagasse, banana, lacebark, silk, sinew, catgut, wool, sea silk, mohair, angora, cashmere, collagen, actin, nylon, dacron, rayon, bamboo, modal, diacetate fiber, triacetate fiber, polyvinyl alcohol homopolymer, a polyvinyl alcohol copolymer, or a combination thereof.

In embodiments, the non-water soluble fibers can include an auxiliary agent as described above. In embodiments, the non-water soluble fibers can be substantially free of auxiliary agents as described above. In embodiments, the non-water soluble fibers can include a plasticizer as described above. The total amount of the non-water plasticizer provided in the non-water soluble fiber can be in a range of about 1 wt. % to about 45 wt. %, or about 5 wt. % to about 45 wt. %, or about 10 wt. % to about 40 wt. %, or about 20 wt. % to about 30 wt. %, about 1 wt. % to about 4 wt. %, or about 1.5 wt. % to about 3.5 wt. %, or about 2.0 wt. % to about 3.0 wt. %, for example about 1 wt. %, about 2.5 wt. %, about 5 wt. %, about 10 wt. %, about 15 wt. %, about 20 wt. %, about 25 wt. %, about 30 wt. %, about 35 wt. %, or about 40 wt. %, based on total fiber weight. In embodiments, the non-water soluble fibers comprise glycerin, sorbitol, or a combination thereof. In embodiments, the non-water soluble fibers comprise glycerin. In embodiments, the non-water soluble fibers comprise sorbitol. In certain embodiments, the non-water soluble fibers can include a plasticizer such as glycerin, for example in about 10 wt % based on total fiber weight, and sorbitol, for example in about 5 wt % based on the total fiber weight.

In embodiments, the non-water soluble fibers can include a surfactant as described above. In various embodiments, the amount of surfactant in the water soluble fiber is in a range of about 0.01 wt. %, to about 2.5 wt. %, about 0.1 wt. % to about 2.5 wt. %, about 1.0 wt. % to about 2.0 wt. %, about 0.01 wt % to 0.25 wt %, or about 0.10 wt % to 0.20 wt %. The non-water soluble fibers can include a surfactant such as one or more cocamide, for example a cocamide ethanolamine. In embodiments, the cocamide can comprise cocamide diethanolamine, cocamide monoethanolamine, or a combination thereof. The cocaminde can be used in cosmetic personal care unit dose articles, and can provide various advantages such as prolonged dissolution profile due to the fatty acid chain on the molecule.

In embodiments, any of the auxiliary agents disclosed herein can be added to the fibers of the disclosure. In refinements of the forgoing embodiment can be added to the fiber forming material prior to formation of the fiber such that the auxiliary agents can be added to the surface of a fiber after fiber formation. In refinements of the foregoing embodiments, the auxiliary agents can be added to a surface of the fiber after fiber formation.

When included in the non-water soluble fiber, the colorant can be provided in an amount of 0.01% to 25% by weight of the polymer mixture, such as, 0.02%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, and 24% by weight of the polymer mixture.

Nonwoven Web

The nonwoven web of the disclosure can be water soluble, non-water soluble, or at least partially non-water soluble. The unit dose article of the disclosure can include a nonwoven web, wherein at least a portion of the nonwoven web is soluble in water at a temperature in a range of about 0° C. to about 20° C. according to MSTM 205, or at least a portion of the nonwoven web is not soluble in water at a temperature of 20° C. or less according to MSTM 205, or the nonwoven web is not soluble in water at a temperature of 20° C. or less according to MSTM 205, or the nonwoven web is soluble in water at a temperature in a range of about 0° C. to about 20° C. according to MSTM 205. It will be understand that “at least a portion” of a nonwoven web is soluble (or not soluble) at a given temperature if the nonwoven web includes in the plurality of the fibers, a fiber type which when provided in a nonwoven as the sole fiber type, the nonwoven web consisting of that fiber type is soluble (or not soluble) at the given temperature, according to MSTM-205.

The nonwoven web of the disclosure generally includes a plurality of fibers. A nonwoven web generally refers to an arrangement of fibers bonded to one another, wherein the fibers are neither woven nor knitted. In general, the plurality of fibers can be arranged in any orientation. In embodiments, the plurality of fibers are arranged randomly (i.e., do not have an orientation). In embodiments, the plurality of fibers are arranged in a unidirectional orientation. In embodiments, the plurality of fibers are arranged in a bidirectional orientation. In some embodiments, the plurality of fibers are multi-directional, having different arrangements in different areas of the nonwoven web.

In general, the plurality of fibers in any given nonwoven web can include any fiber forming materials disclosed herein. The nonwoven web can include (1) a single fiber type including a single fiber forming material, (2) a single fiber type including a blend of fiber forming materials, (3) a blend of fiber types, each fiber type including a single fiber forming material, (4) a blend of fiber types, each fiber type including a blend of fiber forming materials, or (5) a blend of fiber types, each fiber type including a single fiber forming material or a blend of fiber forming materials. In embodiments including a blend of fiber types, the different fiber types can have a difference in one or more of the group of length to diameter ratio (L/D), tenacity, shape, rigidness, elasticity, solubility, melting point, glass transition temperature ($T_g$), fiber forming material chemistries, and color. In certain embodiments, the plurality of fibers can comprise two or more types of water soluble fibers. In embodiments, the plurality of fibers can comprise at least one fiber type comprising at least one type of water soluble fiber forming materials and at least one fiber type comprising at least type of one non-water soluble fiber. In embodiments, the plurality of fibers can comprise two or more fiber types comprising at least one type of non-water soluble fiber forming material.

In embodiments, the nonwoven web can further comprise any auxiliary agents as disclosed herein for fibers and/or films. In embodiments, the auxiliary agents can be added to the fiber itself, to the nonwoven web during carding of the nonwoven web, to the nonwoven web prior to bonding (e.g., after carding), to the nonwoven web subsequent to bonding, or a combination thereof. The auxiliary agents added to the fibers during carding can be distributed throughout the nonwoven web. The auxiliary agents added to the nonwoven web after carding but prior to bonding can be selectively added to one or both faces of the nonwoven web.

The auxiliary agents can be applied to one or more faces of a nonwoven web or to an article containing same, e.g., a packet, by any suitable means. In embodiments, the auxiliary agents are in powder form. In refinements of the foregoing embodiment, one or more stationary powder spray guns are used to direct the powder stream towards the web or a packet, from one or more than one direction, while the web or packet is transported through the coating zone by means of a belt conveyor. In embodiments, a web or packet is conveyed through a suspension of the powder in air. In embodiments, the webs or packets are tumble-mixed with the powder in a trough-like apparatus. In embodiments, which can be combined with any other embodiment, electrostatic forces are employed to enhance the attraction between the powder and the packet or web. This type of process is typically based on negatively charging the powder particles and directing these charged particles to the grounded packets or webs. In other alternative embodiments, the powder is applied to the web or packet by a secondary transferring tool including, but not limited to rotating brushes which are in contact with the powder or by powdered gloves which can transfer the powder from a container to the web or packet. In yet another embodiment the powder is applied by dissolving or suspending the powder in a non-aqueous solvent or carrier which is then atomized and sprayed onto the web or packet. In one type of embodiment, the solvent or carrier subsequently evaporates, leaving the active agent powder behind. In one class of embodiments, the powder is applied to the web or packet in an accurate dose. This class of embodiments utilizes closed-system dry lubricant application machinery, such as PekuTECH's powder applicator PM 700 D. In this process the powder, optionally batch-wise or continuously, is fed to a feed trough of application machinery. The webs or packets are transferred from the output belt of a standard rotary drum pouch machine onto a conveyor belt of the powder application machine, wherein a controlled dosage of the powder is applied to the web or packet. The web or packet can thereafter be conveyed to a suitable secondary packaging process.

In embodiments wherein the auxiliary agents are in liquid form or in a solution, the foregoing can be dispersed among the fibers, dispersed on a face of the nonwoven web, or a combination thereof, for example, by spin casting, spraying a solution such as an aerosolized solution, roll coating, flow coating, curtain coating, extrusion, knife coating, and combinations thereof.

The auxiliary agents, such as chemical exfoliants, mechanical exfoliants, fragrances and/or perfume microcapsules, aversive agents, surfactants, colorants, enzymes, skin conditioners, de-oiling agents, cosmetic agents, or a combination thereof, when present in the nonwoven web, are in an amount of at least about 1 wt %, or in a range of about 1 wt % to about 99 wt %, provides additional functionality to the nonwoven web. The chemical exfoliants, mechanical exfoliants, fragrances and/or perfume microcapsules, aversive agents, surfactants, colorants, enzymes, skin conditioners, de-oiling agents, cosmetic agents, or a combination thereof, can take any desired form, including as a solid (e.g., powder, granulate, crystal, flake, or ribbon), a liquid, a mull, a paste, a gas, etc., and optionally can be encapsulated.

In embodiments, the nonwoven web can be colored, pigmented, and/or dyed to provide an improved aesthetic effect relative to water-soluble films. Suitable colorants for use in the nonwoven web can include an indicator dye, such as a pH indicator (e.g., thymol blue, bromothymol, thymolphthalein, and thymolphthalein), a moisture/water indicator (e.g., hydrochromic inks or leuco dyes), or a thermochromic ink, wherein the ink changes color when temperature increases and/or decreases. Suitable colorants include, but are not limited to a triphenylmethane dye, an azo dye, an anthraquinone dye, a perylene dye, an indigoid dye, a food, drug and cosmetic (FD&C) colorant, an organic pigment, an inorganic pigment, or a combination thereof. Examples of colorants include, but are not limited to, FD&C Red #40; Red #3; FD&C Black #3; Black #2; Mica-based pearlescent pigment; FD&C Yellow #6; Green #3; Blue #1; Blue #2; titanium dioxide (food grade); brilliant black; and a combination thereof.

In embodiments, the nonwoven web can include any of the surfactants disclosed herein. In embodiments, the nonwoven web can comprise one or more of the group of: sodium cocoyl isethionate, glucotain, phoenamids, cola lipid, cocamides, such as cocamide ethanolamines, ethylene oxide based surfactants, and saponified oils of avocado and palm.

The nonwoven webs of the disclosure can generally have any thickness. Suitable thicknesses can include, but are not limited to, about 5 to about 10,000 μm (1 cm), about 5 to about 5,000 μm, about 5 to about 1,000 μm, about 5 to about 500 μm, about 200 to about 500 μm, about 5 to about 200 μm, about 20 to about 100 μm, or about 40 to about 90 μm, or about 50 to 80 μm, or about or about 60 to 65 μm for example 50 μm, 65 μm, 76 μm, or 88 μm. The nonwoven webs of the disclosure can be characterized as high loft or low loft. In general, loft refers to the ratio of thickness to mass per unit area (i.e., basis weight). High loft nonwoven webs can be characterized by a high ratio of thickness to mass per unit area. As used herein, "high loft" refers to a nonwoven web of the disclosure having a basis weight as defined herein and a thickness exceeding 200 μm. The thickness of the nonwoven web can be determined by according to ASTM D5729-97, ASTM D5736, and/or ISO 9073-2:1995 and can include, for example, subjecting the nonwoven web to a load of 2 N and measuring the thickness. High loft materials can be used according to known methods in the art, for example, cross-lapping, which uses a cross-lapper to fold the unbonded web over onto itself to build loft and basis weight. Without intending to be bound by theory, in contrast to water-soluble films wherein the solubility of the film can be dependent on the thickness of the film; the solubility of a nonwoven web is not believed to be dependent on the thickness of the web. In this regard, it is believed that because the individual fibers provide a higher surface area than a water soluble film, regardless of the thickness of the nonwoven web, the parameter that limits approach of water to the fibers and, thereby, dissolution of the fibers is the basis weight (i.e., fiber density in the nonwoven).

In general, the coefficient of dynamic friction and the ratio of the coefficient of static friction to the coefficient of dynamic friction for a nonwoven web of the disclosure will be lower than the coefficient of dynamic friction and the ratio of the coefficient of static friction to the coefficient of dynamic friction for a water soluble film due to the increased surface roughness of the nonwoven web relative to a water soluble film, which provides decreased surface contact to the nonwoven web. Advantageously, this surface roughness can provide an improved feel to the consumer (i.e., a cloth-like hand-feel instead of a rubbery hand-feel), improved aesthetics (i.e., less glossy than a water soluble film), and/or facilitate processability in preparing thermoformed, and/or vertical formed, filled, and sealed, and/or multichamber packets which require drawing the web along a surface of the processing equipment/mold. Accordingly, the water soluble fibers and/or non-water soluble fibers should be sufficiently coarse to provide a surface roughness to the resulting nonwoven web without being so coarse as to produce drag.

The solubility in water of the nonwoven webs of the disclosure is generally a function of the type of fiber(s) used to prepare the web as well as the basis weight of the web. Without intending to be bound by theory, it is believed that the solubility profile of a nonwoven web follows the same solubility profile of the fiber(s) used to prepare the nonwoven web, and the solubility profile of the fiber generally follows the same solubility profile of the polymer(s) from which the fiber is prepared. For example, for nonwoven webs comprising PVOH fibers, the degree of hydrolysis of the PVOH polymer can be chosen such that the water-solubility of the nonwoven web is also influenced. In general, at a given temperature, as the degree of hydrolysis of the PVOH polymer increases from partially hydrolyzed (88% DH) to fully hydrolyzed (≥98% DH), water solubility of the polymer generally decreases. Thus, in one option, the nonwoven web can be cold water soluble. For a co-poly (vinyl acetate vinyl alcohol) polymer that does not include any other monomers (e.g., not copolymerized with an anionic monomer) a cold water-soluble web, soluble in water at a temperature of less than 10° C., can include fibers of PVOH with a degree of hydrolysis in a range of about 75% to about 90%, or in a range of about 75% to about 89%, or in a range of about 80% to about 90%, or in a range of about 85% to about 90%, or in a range of about 90% to about 99.5%. In another option the nonwoven web can be hot water-soluble. For example, a co-poly(vinyl acetate vinyl alcohol) polymer that does not include any other monomers (e.g., not copolymerized with an anionic monomer), a hot water-soluble web can be soluble in water at a temperature of at least about 60° C., by including fibers of PVOH with a degree of hydrolysis of at least about 98%.

Modification of PVOH generally increases the solubility of the PVOH polymer. Thus, it is expected that at a given temperature the solubility of a nonwoven web or film prepared from a PVOH copolymer, would be higher than that of a nonwoven web or film prepared from a PVOH homopolymer having the same degree of hydrolysis as the PVOH copolymer. Following these trends, a nonwoven web having specific solubility characteristics can be designed by blending polymers within the fibers and/or blending fibers within the nonwoven web. Further, as described herein, the nonwoven web includes a plurality of fibers that may, in some cases, include two or more fiber types that differ in solubility.

Inclusion of non-water soluble fiber and/or non-water soluble fiber forming material in the plurality of fibers of a nonwoven web can also be used to design a nonwoven web having specific solubility and/or prolonged release properties. Without intending to be bound by theory, it is believed that as the weight percent of non-water soluble fiber included in a nonwoven web is increased (based on the total weight of the nonwoven web), the solubility of the nonwoven web generally decreases and the prolonged release properties of a pouch comprising a nonwoven web generally increases. Upon contact with water at a temperature at or above the solubility temperature of the water-soluble fiber, a nonwoven web comprising water-soluble fiber and non-water soluble fiber will begin to disperse as the water-soluble fiber dissolves, thereby breaking down the web structure and/or increasing the pore size of the pores of the nonwoven web. In general, the larger the break-down of the web structure or increase in the pore size, the faster the water can access the contents of the pouch and the faster the contents of the pouch will be released. Similarly, prolonged release of the contents of a pouch comprising the nonwoven web of the disclosure can be achieved by using a blend of water-soluble fibers having different solubility properties and/or different solubility temperatures. Once the faster dissolving fiber has dissolved, thereby breaking up the web, the less soluble fibers will have a larger surface area exposed, facilitating dissolution of the less soluble fibers and release of the pouch contents. In embodiments wherein the nonwoven web includes water-soluble fiber and non-water soluble fiber, the ratio of soluble fiber to non-water soluble fiber is not particularly limited. The water-soluble fiber can comprise about 1% to about 99%, about 20% to about 80%, about 40% to about 90%, about 50% to about 90%, or about 60% to about 90% by weight, of the total weight of the plurality of fibers, and the non-water soluble fiber can comprise about 1% to about 99%, about 20% to about 80%, about 10% to about 60%, about 10% to about 50%, or about 10% to about 40% by weight, of the total weight of the fibers. In embodiments, the plurality of fibers comprises about 10% to about 80% water soluble fibers by weight, based on the total weight of the fibers and the balance being non-water soluble fibers.

In embodiments, the nonwoven web, the plurality of fibers, the water soluble film, or a combination thereof, disclosed herein can comprises a biodegradable polymer. In certain embodiments, the plurality of fibers can comprise non-water soluble fiber forming materials that are biodegradable. In embodiments, the plurality of fibers can comprise first fiber that is non-water soluble biodegradable fiber, and second fiber that is soluble in water at a temperature of about 10° C. to about 20° C. according to MSTM 205 or not soluble in water at a temperature of about 30° C. or less according to MSTM 205, according to MSTM 205. In embodiments, the nonwoven web is non-water soluble and biodegradable.

In embodiments, the nonwoven web is biodegradable. As used herein, when the nonwoven web is said to be biodegradable, at least 50% of the nonwoven web is biodegradable, for example, at least 60%, at least 70%, at least 80%, at least 90%, or 100%, of the nonwoven web is biodegradable.

The nonwoven web as disclosed herein can comprise the plurality of fibers comprising a first fiber type and a second fiber type, wherein the first and second fiber types have a difference in diameter, length, tenacity, shape, rigidness, elasticity, solubility, melting point, glass transition temperature ($T_g$), chemical composition, color, or a combination thereof. In embodiments, the first fiber type can comprise a PVOH homopolymer fiber forming material, a PVOH copolymer fiber forming material, or a combination thereof. In embodiments, the first fiber type can comprise two or more PVOH homopolymer fiber forming materials, two or more PVOH copolymer fiber forming materials, or a combination thereof. In embodiments, the second fiber type can comprise a PVOH homopolymer fiber forming material, a PVOH copolymer fiber forming material, or a combination thereof. In embodiments, the second fiber type can comprise two or more PVOH homopolymer fiber forming materials, two or more PVOH copolymer fiber forming materials, or a combination thereof. In embodiments, the first fiber type and/or the second fiber typer are non-water soluble fiber forming material. In embodiments, the first fiber type can comprise a non-water soluble polymer fiber forming material and the second fiber type can comprise a polyvinyl alcohol fiber forming material that, when provided as the sole fiber forming material of a nonwoven web or as a film, the resulting web or film is soluble in water at a temperature in a range of about 0° C. to about 20° C. according to MSTM 205. In embodiments, the first fiber type can comprise a non-water soluble polymer fiber forming material and the second fiber type can comprise a PVOH homopolymer or copolymer fiber forming material that, when provided as the sole fiber forming material of a nonwoven web or as a film, the resulting web or film is not soluble in water at a temperature of 20° C. or less according to MSTM 205, according to MSTM 205. In embodiments, the first fiber type comprises two or more polyvinyl alcohol homopolymer fiber forming materials, two or more polyvinyl alcohol copolymer fiber forming materials, or a combination of polyvinyl alcohol homopolymer fiber forming materials and polyvinyl alcohol copolymer fiber forming materials. In embodiments, the second fiber type comprises two or more polyvinyl alcohol homopolymer fiber forming materials, two or more polyvinyl alcohol copolymer fiber forming materials, or a combination of polyvinyl alcohol homopolymer fiber forming materials and polyvinyl alcohol copolymer fiber forming materials.

The plurality of fibers comprised in the nonwoven webs of the disclosure can generally have any tenacity. The tenacity of the fiber correlates to the coarseness of the fiber. As the tenacity of the fiber decreases the coarseness of the fiber increases. Fibers used to prepare the nonwoven webs of the disclosure can have a tenacity in a range of about 1 to about 100 cN/dtex, or about 1 to about 75 cN/dtex, or about 1 to about 50 cN/dtex, or about 1 to about 45 cN/dtex, or about 1 to about 40 cN/dtex, or about 1 to about 35 cN/dtex, or about 1 to about 30 cN/dtex, or about 1 to about 25 cN/dtex, or about 1 to about 20 cN/dtex, or about 1 to about 15 cN/dtex, or about 1 to about 10 cN/dtex, or about 3 to about 8 cN/dtex, or about 4 to about 8 cN/dtex, or about 6 to about 8 cN/dtex, or about 4 to about 7 cN/dtex, or about 10 to about 20, or about 10 to about 18, or about 10 to about 16, or about 1 cN/dtex, about 2 cN/dtex, about 3 cN/dtex, about 4 cN/dtex, about 5 cN/dtex, about 6 cN/dtex, about 7 cN/dtex, about 8 cN/dtex, about 9 cN/dtex, about 10 cN/dtex, about 11 cN/dtex, about 12 cN/dtex, about 13 cN/dtex, about 14 cN/dtex, or about 15 cN/dtex. In embodiments, the plurality of fibers can have a tenacity in a range of about 3 cN/dtex to about 15 cN/dtex, or about 5 cN/dtex to about 12 cN/dtex, or about 5 cN/dtex to about 10 cN/dtex.

The tenacity of the nonwoven web can be the same or different from the tenacity of the plurality of fibers used to prepare the web. Without intending to be bound by theory, it is believed that the tenacity of the nonwoven web is related to the strength of the nonwoven web, wherein a higher tenacity provides a higher strength to the nonwoven web. In general, the tenacity of the nonwoven web can be modified by using fibers having different tenacities. The tenacity of the nonwoven web may also be affected by processing. In general, the nonwoven webs of the disclosure have relatively high tenacities, i.e., the nonwoven web is a self-supporting web that can be used as the sole material for preparing an article and/or pouch. In contrast, nonwoven webs prepared according to melt blown, electro-spinning, and/or rotary spinning processes typically have low tenacities, and may not be self-supporting or capable of being used as a sole web for forming an article or pouch.

The fibers used to prepare the nonwoven webs of the disclosure can generally have any fineness. The fineness of the fiber correlates to how many fibers are present in a cross-section of a yarn of a given thickness. The fineness of a fiber can be measured by the linear mass density, a measure of the ratio of fiber mass per unit length. The main physical unit of linear mass density is 1 tex, which is equal to 1000 m of fiber weighing 1 g. Typically, the unit dtex is used, representing 1 g/10,000 m of fiber. The linear mass density can be selected to provide a nonwoven web having suitable stiffness/hand-feel of the nonwoven web, torsional rigidity, reflection and interaction with light, absorption of dye and/or other actives/additives, ease of fiber spinning in the manufacturing process, and uniformity of the finished article. In general, as the linear mass density of the fibers increases the nonwovens resulting therefrom demonstrate higher uniformity, improved tensile strengths, extensibility and luster. Additionally, without intending to be bound by theory it is believed that finer fibers will lead to slower dissolution times as compared to larger fibers based on density. Further, without intending to be bound by theory, when a blend of fiber types is used, the average linear mass density can be determined using a weighted average of the individual fiber types. Fibers can be characterized as very fine (dtex≤1.22), fine (1.22≤dtex≤1.54), medium (1.54≤dtex≤1.93), slightly coarse (1.93≤dtex≤2.32), and coarse (dtex≥2.32). The nonwoven web of the disclosure can include fibers that are very fine, fine, medium, slightly coarse, or a combination thereof. In embodiments, the nonwoven web has an average linear mass density in a range of about 1 dtex to about 5 dtex, or about 1 dtex to about 3 dtex, or about 1.5 dtex to about 2.5 dtex. In embodiments, the nonwoven web comprises a blend of fibers wherein first fiber comprises 1.7 dtex average linear mass density and second fiber comprises 2.2 dtex average linear mass density.

The plurality of fibers used to prepare the nonwoven webs of the disclosure typically have a diameter in a range of about 10 micron to 300 micron, for example, at least 10 micron, at least 25 micron, at least 50 micron, at least 100 micron, or at least 125 micron and up to about 300 micron, up to about 275 micron, up to about 250 micron, up to about 225 micron, or up to about 200 micron. In embodiments, the plurality of fibers used to prepare the nonwoven webs of the disclosure can have a diameter greater than 100 micron to about 300 micron. In embodiments, the diameters of the plurality of fibers used to prepare the nonwoven webs of the disclosure have diameters that are substantially uniform. In embodiments, the one or more fiber types can have a mean diameter in a range of about 10 micron to about 300 micron, or about 50 micron to 200 micron, or about 50 micron to about 100 micron.

The plurality of fibers used to prepare the nonwoven webs of the disclosure can generally be of any length. In embodiments, the length of the plurality of fibers can be in a range of about 30 mm to about 100 mm, about 10 mm to about 60 mm, or about 30 mm to about 60 mm, for example, at least about 30 mm, at least about 35 mm, at least about 40 mm, at least about 45 mm, or at least about 50 mm, and up to about 100 mm, up to about 95 mm, up to about 90 mm, up to about 80 mm, up to about 70 mm, or up to about 60 mm. In embodiments, the length of the plurality of fibers can be less than about 30 mm or in a range of about 0.25 mm to less than about 30 mm, for example, at least about 0.25 mm, at least about 0.5 mm, at least about 0.75 mm, at least about 1 mm, at least about 2.5 mm, at least about 5 mm, at least about 7.5 mm, or at least about 10 mm and up to about 29 mm, up to about 28 mm, up to about 27 mm, up to about 26 mm, up to about 25 mm, up to about 20 mm, or up to about 15 mm. In embodiments, the plurality of fibers have an average length of about 30 mm to about 100 mm, or about 30 mm to about 60 mm. In embodiments, the nonwoven web comprises a blend of fiber types wherein first fiber type comprises a length of about 38 mm and second fiber type comprises a length of about 54 mm.

The plurality of fibers used to prepare the nonwoven webs of the disclosure can generally have any length to diameter (L/D) ratio. Advantageously, the tactility of a nonwoven web of the disclosure can be controlled using the L/D ratio of the fibers and the respective amounts of fibers having various L/D ratios in the nonwoven composition. In general, as the L/D of the fiber decreases, the stiffness and resistance to bending increases, providing a rougher hand feel. The fibers of the disclosure generally impart a rough feel to a nonwoven web including same, when the fibers have a low L/D ratio in a range of about 0.5 to about 15, or about 0.5 to about 25, or about 1 to about 5. Such low L/D fibers can be provided in a nonwoven web in an amount in a range of about 0 to about 50% by weight, based on the total weight of the fibers in the nonwoven web, for example, in a range of about 0.5 wt. % to about 25 wt. %, or about 1 wt. % to about 15 wt. %. If the amount of low L/D fibers in a nonwoven web is not known, the amount can be estimated by visual inspection of a micrograph of a nonwoven web. FIG. 3A is a micrograph of a nonwoven web having 0% of low L/D fibers and a softness rating of 1, whereas FIG. 3B is a micrograph of a nonwoven web having 25% of low L/D fibers and a softness rating of 5. In embodiments wherein a first fiber includes a blend of fiber forming materials including a first polyvinyl alcohol fiber forming material, at least a portion of the first fibers can have a L/D ratio of about 0.5 to about 25, or about 0.5 to about 15, or about 1 to about 5.

Pore sizes can be determined using high magnification and ordered surface analysis techniques including, but not limited to Brunauer-Emmett-Teller theory (BET), small angle X-ray scattering (SAXS), and molecular adsorption.

Nonwoven webs can be characterized by basis weight. The basis weight of a nonwoven web is the mass per unit area of the nonwoven web. Basis weight can be modified by varying manufacturing conditions, as is known in the art. A nonwoven web can have the same basis weight prior to and subsequent to bonding. Alternatively, the bonding method can change the basis weight of the nonwoven web. For example, wherein bonding occurs through the application of heat and pressure, the thickness of the nonwoven (and, thus, the area of the nonwoven) can be decreased, thereby increasing the basis weight. Accordingly, as used herein and unless specified otherwise, the basis weight of a nonwoven refers to the basis weight of the nonwoven subsequent to bonding.

The nonwoven webs of the disclosure can generally have any basis weight in a range of about 0.1 g/m$^2$ to about 700 g/m$^2$, about 0.5 g/m$^2$ to about 600 g/m$^2$, about 1 g/m$^2$ to about 500 g/m$^2$, about 1 g/m$^2$ to about 400 g/m$^2$, about 1 g/m$^2$ to about 300 g/m$^2$, about 1 g/m$^2$ to about 200 g/m$^2$, about 1 g/m$^2$ to about 100 g/m$^2$, about 30 g/m$^2$ to about 100 g/m$^2$, about 20 g/m$^2$ to about 100 g/m$^2$, about 20 g/m$^2$ to about 80 g/m$^2$, or about 25 g/m$^2$ to about 70 g/m$^2$.

Further, as the basis weight of the web increases the rate of dissolution of the web decreases, provided the fiber composition and web thickness remain constant, as there is more material to be dissolved. For example, at a given temperature, a water soluble web prepared from fibers comprising PVOH polymer(s) and having a basis weight of, e.g., 40 g/m$^2$, is expected to dissolve slower than an otherwise-identical water soluble web having a basis weight of, e.g., 30 g/m$^2$. Accordingly, basis weight can also be used to modify the solubility characteristics of the nonwoven web. The nonwoven web can generally have any basis weight in a range of about 1 g/m$^2$ to about 700 g/m$^2$, about 1 g/m$^2$ to about 600 g/m$^2$, about 1 g/m$^2$ to about 500 g/m$^2$, about 1 g/m$^2$ to about 400 g/m$^2$, about 1 g/m$^2$ to about 300 g/m$^2$, about 1 g/m$^2$ to about 200 g/m$^2$, about 10 g/m$^2$ to about 100 g/m$^2$, about 30 g/m$^2$ to about 100 g/m$^2$, about 20 g/m$^2$ to about 100 g/m$^2$, about 20 g/m$^2$ to about 80 g/m$^2$, about 25 g/m$^2$ to about 70 g/m$^2$, or about 40 g/m$^2$ to about 60 g/m$^2$.

The nonwoven web of the disclosure can be used as a single layer or can be layered with other nonwoven webs, or can be in the form of a laminate with a water soluble film. In some embodiments, the nonwoven web includes a single layer of nonwoven web. In some embodiments, the nonwoven web is a multilayer nonwoven web comprising two or more layers of nonwoven webs. The two or more layers can be laminated to each other. In refinements of the foregoing embodiment, the two or more layers can be the same (e.g., be prepared from the same fibers and basis weight). In refinements of the foregoing embodiment, the two or more layers can be different (e.g., be prepared from different types of fibers, fiber chemistries, and/or have different basis weights).

In general, a multilayer nonwoven web can have a basis weight that is the sum of the basis weights of the individual layers. Accordingly, a multilayer nonwoven web will take longer to dissolve than any of the individual layers provided as a single layer Water Soluble Film The water-soluble film described herein generally comprises any of the water soluble polymers disclosed herein. In embodiments, the water soluble film of the disclosure comprises a polyvinyl alcohol (PVOH) resin, a modified polyvinyl alcohol resin, or combinations thereof. In embodiments, the water soluble film includes a PVOH resin selected from the group consisting of a PVOH homopolymer, a PVOH copolymer having an anionic modification, and combinations of the foregoing. In embodiments, the water soluble film can comprise a single PVOH polymer or a blend of PVOH polymer. In embodiments, the water soluble film comprises a PVOH homopolymer. In embodiments, the water soluble film comprises a hot water soluble PVOH homopolymer. In embodiments wherein the nonwoven web includes a surfactant and/or an exfoliant, the water soluble film can comprise a PVOH copolymer having an anionic modification. In embodiments, the water soluble film can comprise a water soluble polyvinyl alcohol homopolymer or copolymer that, when provided in a film as the sole film forming material, said film is soluble in water at a temperature in a range of about 0° C. to about 20° C. according to MSTM 205. In embodiments, the water soluble film can comprise a water soluble polyvinyl alcohol homopolymer or copolymer that, when provided in a film as the sole film forming material, said film is not water soluble at a water temperature of 20° C. or less according to MSTM 205, according to MSTM 205.

The water-soluble film can include other film forming polymers including, but not limited to, polyvinyl alcohols, water-soluble acrylate copolymers, polyethyleneimine, pullulan, water-soluble natural polymers including, but not limited to, guar gum, gum Acacia, xanthan gum, carrageenan, and starch, water-soluble polymer modified starches, copolymers of the foregoing, or a combination of any of the foregoing. Yet other water-soluble polymers can include polyalkylene oxides, polyacrylamides, celluloses, cellulose ethers, cellulose esters, cellulose amides, polyvinyl acetates, polycarboxylic acids and salts thereof, polyaminoacids, polyamides, gelatines, methylcelluloses, carboxymethylcelluloses and salts thereof, dextrins, ethylcelluloses, hydroxyethyl celluloses, hydroxypropyl methylcelluloses, maltodextrins, polymethacrylates, or a combination of any of the foregoing. Such water-soluble polymers are commercially available from a variety of sources. In embodiments, the water soluble film can include a PVOH homopolymer, PVOH copolymer, or a combination thereof. In embodiments, the water soluble film comprises a single PVOH homopolymer or a blend of PVOH homopolymers. In further embodiments, the water soluble film comprises a PVOH homopolymer with a viscosity in a range of 5 cP to 23 cP and a degree of hydrolysis in a range of 86% to 92%.

The film can have any suitable thickness, and a film thickness of about 76 microns (μm) is typical and particularly contemplated. Other values and ranges contemplated include values in a range of about 5 to about 200 μm, or in a range of about 20 to about 100 μm, or about 40 to about 90 μm, or about 50 to 80 μm, or about or about 60 to 65 μm for example 65 μm, 76 μm, or 88 μm.

In embodiments, the water soluble films can include an auxiliary agent as described above. In embodiments, the water soluble films can be substantially free of auxiliary agents as described above. In embodiments, the water soluble films can include a plasticizer as described above. The total amount of the non-water plasticizer provided in the water soluble film can be in a range of about 1 wt. % to about 45 wt. %, or about 5 wt. % to about 45 wt. %, or about 10 wt. % to about 40 wt. %, or about 20 wt. % to about 30 wt. %, about 1 wt. % to about 4 wt. %, or about 1.5 wt. % to about 3.5 wt. %, or about 2.0 wt. % to about 3.0 wt. %, for example about 1 wt. %, about 2.5 wt. %, about 5 wt. %, about 10 wt. %, about 15 wt. %, about 20 wt. %, about 25 wt. %, about 30 wt. %, about 35 wt. %, or about 40 wt. %, based on total film weight. In embodiments, the water soluble film comprises one or more of propylene glycol, glycerol, diglycerol, sorbitol, xylitol, maltitol, trimethylol propane (TMP), and polyethylene glycol (100-1000 molecular weight).

In embodiments, the water soluble films can include a surfactant as described above. In various embodiments, the amount of surfactant in the water soluble film is in a range of about 0.01 wt. %, to about 2.5 wt. %, about 0.1 wt. % to about 2.5 wt. %, about 1.0 wt. % to about 2.0 wt. %, about 0.01 wt % to 0.25 wt %, or about 0.10 wt % to 0.20 wt %. In embodiments, the water soluble film comprises one or more of polysorbate 80, lecithin from various plant sources, and sodium lauryl sulfate (SLS) and the like.

In embodiments, the auxiliary agents of the water soluble film can include fillers/extenders/antiblocking agents/detackifying agents. Suitable fillers/extenders/antiblocking agents/detackifying agents include, but are not limited to, crosslinked polyvinylpyrrolidone, crosslinked cellulose, microcrystalline cellulose, silica, metallic oxides, calcium carbonate, talc, mica, stearic acid and metal salts thereof, for example, magnesium stearate. Optionally an additional unmodified starch or modified starch can be included the water-soluble in addition to one of the specific starch components described above, for example, hydroxypropylated starch present in an amount in a range of about 5 phr to about 30 phr, or modified starch having a degree of modification of greater than about 2% and is present in an amount in a range of about 2.5 phr to about 30 phr, or an unmodified starch having an amylose content in a range of about 20% to about 80%, or a hydroxypropyl modified starch having an amylose content in a range of about 23% to about 95% when the polyvinyl alcohol comprises an unmodified polyvinyl alcohol or an anionic modified polyvinyl alcohol copolymer with the proviso that the anionic modifier is not an acrylate. Preferred materials are starches, modified starches and silica. In one type of embodiment, the amount of filler/extender/antiblocking agent/detackifying agent in the water-soluble film can be in a range of about 1 wt. % to about 6 wt. %, or about 1 wt. % to about 4 wt. %, or about 2 wt. % to about 4 wt. %, or about 1 phr to about 6 phr, or about 1 phr to about 4 phr, or about 2 phr to about 4 phr, for example. In embodiments, when a starch or modified starch is included in the water-soluble film in addition to one of the specific starch components described above, the additional starch component will be provided in an amount of less than about 50 wt. %, based on the total weight of all starches included in the film. Without intending to be bound by theory, it is believed that any benefit provided to the water-soluble films of the disclosure from the inclusion of the starch component described above is not affected by including an additional starch component that provides a lesser benefit to the water-soluble film or no benefit to the water-soluble film.

The water-soluble film can further have a residual moisture content of at least 4 wt. %, for example in a range of about 4 to about 10 wt. %, as measured by Karl Fischer titration.

Methods of Preparing Fibers

Wet Cooled Gel Spinning

In embodiments, the plurality of water soluble fibers can include water soluble fibers prepared according to a wet cooled gel spinning process, the wet cooled gel spinning process including the steps of:

(a) dissolving the water soluble polymer (or polymers) in solution to form a polymer mixture, the polymer mixture optionally including auxiliary agents;
(b) extruding the polymer mixture through a spinneret nozzle to a solidification bath to form an extruded polymer mixture;
(c) passing the extruded polymer mixture through a solvent exchange bath;
(d) optionally wet drawing the extruded polymer mixture; and
(e) finishing the extruded polymer mixture to provide the water soluble fibers.

The solvent in which the water soluble polymer is dissolved can suitably be any solvent in which the water soluble polymer is soluble. In embodiments, the solvent in which the water soluble polymer is dissolved includes a polar aprotic solvent. In embodiments, the solvent in which the water soluble polymer is dissolved includes dimethyl sulfoxide (DMSO).

In general, the solidification bath includes a cooled solvent for gelling the extruded polymer mixture. The solidification bath can generally be at any temperature that facilitates solidification of the extruded polymer mixture. The solidification bath can be a mixture including a solvent in which the polymer is soluble and a solvent in which the polymer is not soluble. The solvent in which the polymer is not soluble is generally the primary solvent, wherein the solvent in which the polymer is not soluble makes up greater than 50% of the mixture by volume.

After passing through the solidification bath, the extruded polymer mixture gel can be passed through one or more solvent replacement baths. The solvent replacement baths are provided to replace the solvent in which the water soluble polymer is soluble with the solvent in which the water soluble polymer is not soluble to further solidify the extruded polymer mixture and, further, to replace the solvent in which the water soluble polymer is soluble with a solvent that will more readily evaporate, thereby reducing the drying time. Solvent replacement baths can include a series of solvent replacement baths having a gradient of solvent in which the water soluble polymer is soluble with the solvent in which the water soluble polymer is not soluble, a series of solvent replacement baths having only the solvent in which the water soluble polymer is not soluble, or a single solvent replacement bath having only the solvent in which the water soluble polymer is not soluble. In embodiments, at least one solvent replacement bath can consist essentially of a solvent in which the water soluble polymer is not soluble.

Finished fibers are sometimes referred to as staple fibers, shortcut fibers, or pulp. In embodiments, finishing includes drying the extruded polymer mixture. In embodiments, finishing includes cutting or crimping the extruded polymer mixture to form individual fibers. Wet drawing of the extruded polymer mixture can provide a substantially uniform diameter to the extruded polymer mixture and, thus, the fibers cut therefrom. Drawing is distinct from extruding, as is well known in the art. In particular, extruding refers to the act of making fibers by forcing the resin mixture through the spinneret head whereas drawing refers to mechanically pulling the fibers in the machine direction to promote polymer chain orientation and crystallinity for increased fiber strength and tenacity.

In embodiments wherein the water soluble fibers are prepared from a wet cooled gel spinning process, the water soluble polymer can be generally any water soluble polymer or blend thereof, e.g., two or more different polymers, as generally described herein. In refinements of the foregoing embodiment, the polymer(s) can have any degree of polymerization (DP), for example, in a range of 10 to 10,000,000, for example, at least 10, at least 20, at least 50, at least 100, at least 200, at least 300, at least 400, at least 500, at least 750, or at least 1000 and up to 10,000,000, up to 5,000,000, up to 2,500,00, up to 1,000,000, up to 900,000, up to 750,000, up to 500,000, up to 250,000, up to 100,000, up to 90,000, up to 75,000, up to 50,000, up to 25,000, up to 12,000, up to 10,000, up to 5,000, or up to 2,500, for example in a range of 1000 to about 50,000, 1000 to about 25,000, 1000 to about 12,000, 1000 to about 5,000, 1000 to about 2,500, about 50 to about 12,000, about 50 to about 10,000, about 50 to about 5,000, about 50 to about 2,500, about 50 to about 1000, about 50 to about 900, about 100 to about 800, about 150 to about 700, about 200 to about 600, or about 250 to about 500. In embodiments, the DP is at least 1,000. Auxiliary agents, as described above, can be added to the fibers themselves or to the nonwoven web during the carding and/or bonding process.

Thermoplastic Fiber Spinning

Thermoplastic fiber spinning is well known in the art. Briefly, thermoplastic fiber spinning includes the steps of:

(a) preparing a polymer mixture including the fiber forming polymer optionally including auxiliary agents;
(b) extruding the polymer mixture through a spinneret nozzle to form an extruded polymer mixture;
(c) optionally drawing the extruded polymer mixture; and
(d) finishing the extruded polymer mixture to provide the fibers.

The finished staple fibers of the thermoplastic fiber spinning process can be finished by drying, cutting, and/or crimping to form individual fibers. Drawing of the extruded polymer mixture mechanically pulls the fibers in the machine direction, promoting polymer chain orientation and crystallinity for increased fiber strength and tenacity. Preparing the polymer mixture for thermoplastic fiber spinning can typically include (a) preparing a solution of a fiber-forming material and a readily volatile solvent such that after extruding the solution through the spinneret when the solution is contacted with a stream of hot air, the solvent readily evaporates leaving solid fibers behind or (b) melting the polymer such that after extruding the hot polymer through the spinneret, the polymer solidifies by quenching with cool air. The thermoplastic fiber spinning method is distinct from the wet cooled gel spun method at least in that (a) in the thermoplastic fiber spinning method the extruded fibers are solidified by evaporation of the solvent or by quenching hot solid fibers with cool air, rather than by use of a solidification bath; and (b) in the wet-cool gel spun method, the optional drawing is performed while the fibers are in a gel state rather than a solid state.

Fiber forming materials for preparing fibers from a thermoplastic fiber spinning process can be generally be any fiber forming polymer or blend thereof, e.g., two or more different polymers, provided that the polymer or blend thereof has suitable solubility in a readily volatile solvent and/or have a melting point lower than and distinct from their degradation temperature. Further, when a blend of fiber forming polymers are used to make a fiber, the fiber forming materials must have similar solubility in a readily volatile solvent and/or have similar heat profiles such that the two or more fiber forming materials will melt at similar temperatures. In contrast, the fiber forming materials for preparing fibers from the wet cooled gel spinning process are not as limited and fibers can be prepared from a blend of any two or more polymers that are soluble in the same solvent system, and the solvent system need not be a single solvent or even a volatile solvent.

The fiber forming polymer(s) for preparing thermoplastic fiber spun fibers can have a degree of polymerization (DP), for example, in a range of 10 to 10,000 for example, at least 10, at least 20, at least 50, at least 100, at least 200, at least 300, at least 400, at least 500, at least 750, or at least 1000 and up to 10,000, up to 5,000, up to 2,500, up to 1,000, up to 900, up to 750, up to 500, or up to 250. In embodiments, the DP is less than 1,000.

Melt Spinning

Melt spinning is well known in the art and is understood to refer to both spun bond processes and melt blown processes. Melt spinning is a continuous process which directly prepares a nonwoven web in-line with fiber formation. As such, the melt-spun formed fibers are not finished and cut to any consistent length (e.g., staple fibers are not prepared by these processes). Additionally, melt spinning does not include a drawing step and, therefore, the only control over the diameter of the resulting melt-spun fibers is the size of the holes through which the fiber forming materials are extruded, and the polymer chains are typically not oriented in any specific direction.

Briefly, melt spinning includes the steps of:

(a) preparing a polymer mixture including the fiber forming polymer optionally including auxiliary agents;
(b) extruding the polymer mixture into a die assembly to form an extruded polymer mixture;
(c) quenching the extruded polymer mixture;
(d) depositing the quenched, extruded polymer mixture on a belt to form a nonwoven web; and
(e) bonding the nonwoven web.

In the spun bond process, the extruded polymer mixture is pumped into the die assembly as molten polymer and quenched with cold air once passed through the die assembly. In the melt blown process, the extruded polymer mixture is pumped into a die assembly having hot air blown through it and is quenched upon exiting the die assembly and coming into contact with ambient temperature air. In both processes, the fibers are continuously dropped onto a belt or drum, usually facilitated by pulling a vacuum under the belt or drum.

The diameter of melt-spun fibers are generally in a range of about 0.1 to about 50 micron, for example, at least about 0.1 micron, at least about 1 micron, at least about 2 micron, at least about 5 micron, at least about 10 micron, at least about 15 micron, or at least about 20 micron and up to about 50 micron, up to about 40 micron, up to about 30 micron, up to about 25 micron, up to about 20 micron, up to about 15 micron, up to about 10 micron, about 0.1 micron to about 50 micron, about 0.1 micron to about 40 micron, about 0.1 micron to about 30 micron, about 0.1 micron to about 25 micron, about 0.1 micron to about 20 micron, about 0.1 micron to about 15 micron, about 0.1 micron to about 10 micron, about 0.1 micron to about 9 micron, about 0.1 micron to about 8 micron, about 0.1 micron to about 7 micron, about 0.1 micron to about 6 micron, about 0.1 micron to about 6 micron, about 5 micron to about 35 micron, about 5 micron to about 30 micron, about 7.5 micron to about 25 micron, about 10 micron to about 25 micron, or about 15 micron to about 25 micron. It is well known in the art that melt blown processes can provide micro-fine fibers having an average diameter in a range of about 1-10 micron, however, the melt blown process has very high variation in fiber-to-fiber diameter, e.g., 100-300% variation. Further, it is well known in the art that spun bond fibers can have larger average fiber diameters, e.g., typically about 15 to about 25 micron, but improved uniformity between fibers, e.g., about 10% variation.

The fiber forming material for heat extruded processes (e.g., melt-spun, thermoplastic fiber spinning) is more limited than for the wet-cooled gel spun process. In general, the degree of polymerization for heat extruding processes is limited to a range of about 200 to about 500. As the degree of polymerization decreases below 200, the viscosity of the fiber forming material is too low and the individual fibers prepared by pumping the material through the die assembly do not maintain adequate separation after exiting the die assembly. Similarly, as the degree of polymerization increases above 500, the viscosity is too high to efficiently pump the material through sufficiently small holes in the die assembly to run the process at high speeds, thus losing process efficiency and fiber and/or nonwoven uniformity. Further, processes requiring heating of the fiber forming material, are unsuitable for polyvinyl alcohol homopolymers as the homopolymers generally do not have the thermal stability required.

The wet cooled gel spinning process advantageously provides one or more benefits such as providing a fiber that includes a blend of water soluble polymers, providing control over the diameter of the fibers, providing relatively large diameter fibers, providing control over the length of the fibers, providing control over the tenacity of the fibers, providing high tenacity fibers, providing fibers from polymers having a large degree of polymerization, and/or providing fibers which can be used to provide a self-supporting nonwoven web. Continuous processes such as spun bond, melt blown, electro-spinning and rotary spinning generally do not allow for blending of water soluble polymers (e.g., due to difficulties matching the melt index of various polymers), forming large diameter (e.g., greater than 50 micron) fibers, controlling the length of the fibers, providing high tenacity fibers, and the use of polymers having a high degree of polymerization. Further, the wet cooled gel spinning process advantageously is not limited to polymers that are only melt processable and, therefore, can access fibers made from fiber forming materials having very high molecular weights, high melting points, low melt flow index, or a combination thereof, providing fibers having stronger physical properties and different chemical functionalities compared to fibers prepared by a heat extrusion process. Further still, advantageously, the wet cooled gel spinning process is not limited by the viscosity of the polymer. In contrast, it is known in the art that processes that require melting of the fiber forming material are limited to fiber forming materials having viscosities of 5 cP or less. Thus, fibers including polymers, including polyvinyl alcohol homopolymers and copolymers, having a viscosity of greater than 5 cP are only accessible by wet cooled gel spinning.

Methods of Preparing Nonwoven Webs

The nonwoven webs of the disclosure are generally sheet-like structures having two exterior surfaces, the nonwoven webs including a plurality of fibers. The nonwoven webs of the disclosures can be prepared from fibers using any known methods in the art. As is known in the art, when fibers are spun bond or melt blown, the fibers are continuously laid down to form the nonwoven web, followed by bonding of the fibers.

Staple fibers can be carded or airlaid and bonded to provide a nonwoven web. Methods of carding and airlaying are well known in the art.

Methods of bonding nonwoven webs are well known in the art. In general, bonding can include thermal, mechanical, and/or chemical bonding. Thermal bonding can include, but is not limited to calendaring, embossing, air-through, and ultra-sound. Mechanical bonding can include, but is not limited to, hydro-entangling (spunlace), needle-punching, and stitch-bonding. Chemical bonding can include, but is not limited to, solvent bonding and resin bonding.

Thermal bonding is achieved by applying heat and pressure, and typically maintains the pore size, shape, and alignment produced by the carding process. The conditions for thermal bonding can be readily determined by one of ordinary skill in the art. In general, if the heat and/or pressure applied is too low, the fibers will not sufficiently bind to form a free-standing web and if the heat and/or pressure is too high, the fibers will begin to meld together. The fiber chemistry dictates the upper and lower limits of heat and/or pressure for thermal bonding. Without intending to be bound by theory, it is believed that at temperatures above 235° C., polyvinyl alcohol based fibers degrade. Methods of embossment for thermal bonding of fibers are known. The embossing can be a one-sided embossing or a double-sided embossing. Typically, embossing of water soluble fibers includes one-sided embossing using a single embossing roll consisting of an ordered circular array and a steel roll with a plain surface. As embossing is increased (e.g., as surface features are imparted to the web), the surface area of the web is increased. Without intending to be bound by theory it is expected that as the surface are of the web is increased, the solubility of the web is increased. Accordingly, the solubility properties of the nonwoven web can be advantageously tuned by changing the surface area through embossing.

Air-through bonding generally requires a high thermoplastic content in the nonwoven web and two different melting point materials. In air-through bonding, the non-bonded nonwoven web is circulated around a drum while hot air flows from the outside of the drum toward the center of the drum. Air-through bonding can provide nonwovens having low density and higher basis weight (e.g., greater than 20 to about 2000 g/m$^2$). Nonwovens bonded by air-bonding a typically very soft.

Chemical bonding generally includes solvent bonding and resin bonding. In particular, chemical bonding typically uses a binder solution of a solvent and a resin (e.g., latex or the waste polymer left over from preparing the fibers). The nonwoven can be coated with the binder solution and heat and pressure applied to cure the binder and bond the nonwoven. The binder solution can be applied by immersing the nonwoven in a bath of binder solution, spraying the binder solution onto the nonwoven, extruding the binder solution onto the web (foam bonding), and/or applying the binder solution as a print or gravure.

Chemical bonding can result in smaller, less ordered pores relative to the pores as carded/melt-spun. Without intending to be bound by theory, it is believed that if the resin solution used for chemical bonding is sufficiently concentrated and/or sufficient pressure is applied, a nonporous nonwoven web can be formed. The solvent used in chemical bonding induces partial solubilization of the existing fibers in the web to weld and bond the fibers together. Thus, in general, the solvent for chemical bonding can be any solvent that can at least partially solubilize one or more fiber forming materials of the fibers of the nonwoven. In embodiments, the solvent is selected from the group consisting of water, ethanol, methanol, DMSO, glycerin, and a combination thereof. In embodiments, the solvent is selected from the group consisting of water, glycerin, and a combination thereof. In embodiments, the binder solution comprises a solvent selected from the group consisting of water, ethanol, methanol, DMSO, glycerin, and a combination thereof and further comprises a resin selected from the group consisting of polyvinyl alcohol, latex, and polyvinylpyrrolidone. The binder provided in the solution assists in the welding process to provide a more mechanically robust web. The temperature of the polymer solution is not particularly limited and can be provided at room temperature (about 23° C.).

In some embodiments, a second layer of fibers can be used to bond the nonwoven web. In embodiments, the nonwoven layer can be bonded using thermal, mechanical, or chemical bonding, alone or in addition to bonding using an additional layer of nonwoven web/fibers.

Methods of Laminating Films to Nonwoven Webs

Methods of preparing a laminate (e.g., water soluble film and a nonwoven) can include, but is not limited to, calendar lamination (thermal with pressure) or melt adhesion.

Calendar lamination is achieved by applying heat and pressure. The conditions for calendar lamination can be readily determined by one of ordinary skill in the art. In general, if the heat and/or pressure applied is too low, the fibers will not sufficiently bind to the water soluble film to form a laminate and if the heat and/or pressure is too high, the fibers will begin to meld together with each other and the film. The fiber chemistry and film chemistry dictates the upper and lower limits of heat and/or pressure for calendar lamination. Without intending to be bound by theory, it is believed that at temperatures above 235° C., polyvinyl alcohol based fibers degrade. In embodiments, the heat added to the overlaid nonwoven and water soluble film is about 50° C. to about 200° C., for example, about 100° C. to about 200° C., about 110° C. to about 190° C., about 120° C. to about 180° C., or about 130° C. to about 160° C. In embodiments, the pressure applied to the overlaid nonwoven and water soluble film is about 5 psi to about 50 psi, such as, about 10 psi to about 40 psi, about 15 psi to about 30 psi, or about 20 psi to about 30 psi. In embodiments, the heat added to the overlaid nonwoven and water soluble film is about 150° C. and the pressure applied is about 25 psi. In embodiments, the heat and pressure are applied for about 2-4 seconds. Methods of embossment for calendar lamination of fibers and/or the film are contemplated. The embossing can be a one-sided embossing or a double-sided embossing. Typically, embossing of water-soluble fibers and/or water soluble films includes one-sided embossing using a single embossing roll consisting of an ordered circular array and a steel roll with a plain surface. As embossing is increased (e.g., increased amounts of surface features are imparted to the web and/or the film), the surface area of the laminate is increased. Without intending to be bound by theory it is believed that as the surface of the article is decreased, the solubility of the web and/or film is decreased. Accordingly, the solubility properties of the nonwoven web and/or water soluble film can be advantageously tuned by changing the surface area through embossing. Without intending to be bound by theory, it is believed that as the degree of lamination of the unit dose article is increased, the surface area of the laminate decreases and the bonding between the water soluble film and nonwoven increases, resulting in the solubility decreasing and the liquid release time increasing.

Melt adhesion lamination is achieved by applying an adhesive directly to the the water soluble film and the nonwoven web is then laid on top of the water soluble film with the applied adhesive, and is subjected to cold lamination for adhesion of the nonwoven web and the water soluble film. As used herein, the term "cold lamination" refers to a lamination process that involves pressure but does not involve added heat. The adhesive can be any suitable adhesive to one of ordinary skill in the art. In embodiments, the adhesive is a Henkel National Adhesive. The application of the adhesive directly to the water soluble film can be applied by any suitable method to one of ordinary skill in the art, such as, a hot melt-spray process. In embodiments, the melt adhesion lamination process can include a hot melt spray process at 160° C., followed by cold lamination at a pressure of 94 N/mm$^2$.

The laminate of the disclosure generally includes a water soluble film and a nonwoven web. In embodiments, the laminates can have a degree of lamination of about 1% to about 100%, for example, the degree of lamination can be in a range of about 1% to about 90%, or about 25% to about 75%, or about 1% to about 50%, or about 5% to about 25%, or about 25% to about 100%, or about 50% to about 100%. As used herein, the term "degree of lamination" refers to the amount of total area of the water soluble film that is bonded to the nonwoven web. For example, a laminate having a degree of lamination of about 25% or less means that about 25% or less of the water soluble film's area is bonded to the nonwoven web, e.g., lamination at the seals only. For example, a laminate having a degree of lamination of about 100% means that about 100% of the area of the water soluble film is bonded to the nonwoven web. In embodiments wherein the degree of lamination is about 25% or less, the laminate can be achieved during the heat seal process wherein the lamination occurs at each seal of the unit dose article. In embodiments wherein the laminate has a degree of lamination of about 25% or less, this low degree of lamination can be advantageous as there is an interior void volume where the water soluble film and the nonwoven web are not laminated providing physical separation for components having non-compatible chemistries, as well as providing an opportunity for a 2-step delivery system of compositions in a unit dose article. In embodiments, the degree of lamination is in a range of about 5% to about 25%. In embodiments, the degree of lamination is in a range of about 50% to about 100%.

Uses of Unit Dose Articles

The unit dose articles of the disclosure are generally suitable for a variety of commercial applications. Suitable commercial applications for the unit dose articles of the disclosure can include, pouches and packets for delivering personal care products such as exfoliating materials, shampoo, conditioner, body wash, face wash, skin lotion, skin treatment, hair treatment, bath salts, essential oil, or a combination thereof, where a prolonged release of the personal care product would be desired to extend the use time of the personal care product and hinder immediate washing away of the product. The unit dose articles of the disclosure can be suitable for exfoliating human skin.

Additional applications for the unit dose articles of the disclosure can include, but are not limited to, packets and pouches of agricultural compositions for the prolonged delivery of, e.g., fertilizer to a plant. In embodiments, the unit dose article of the disclosure can include a water soluble film comprising a water soluble and biodegradable polyvinyl alcohol homopolymer in the form of a pouch defining an interior volume having an agricultural composition contained therein and a non-water soluble or less water soluble, biodegradable and/or compostable nonwoven web encompassing the water soluble film, the nonwoven web in the form of a pouch defining a second interior pouch volume and, optionally, containing a second agricultural composition, wherein the nonwoven web comprises a plurality of fibers comprising a non-water soluble, biodegradable and/or compostable fiber forming material, such as cotton as a non-limiting example. Advantageously such a unit dose can allow home gardeners, for example, to provide a pre-packaged amount of an agricultural composition such as a fertilizer to the garden thus allowing for continued and prolonged fertilization of the garden by simply watering the garden (and thereby bringing the unit dose in contact with water and dissolving the water soluble film containing the agricultural composition). The agricultural composition can then diffuse out of the nonwoven web which can maintain sufficient structure until the composition has diffused, and then degrade or compost away. In embodiments, the nonwoven web in the form of a pouch has an exterior face facing away from the interior pouch volume, and the exterior face comprises a personal care composition.

Additional contemplated applications include those that can involve a constant flow of water, for example, automotive cleaning applications and/or dish cleaning applications. Advantageously, in such applications, once at least a portion of the composition is released form the unit dose, the nonwoven web can be used to facilitate foaming and/or scrubbing hard to remove grime without damaging the surface being cleaned, for example, the paint on a car or a non-stick cooking surface.

Additional contemplated applications include those that require keeping active agents separated until the point of use. Advantageously, unit dose articles of the disclosure can contain a first active agent within the first interior pouch volume formed by the water soluble film and a second active agent can be contained within the second interior pouch volume formed by the nonwoven web. The unit dose can be designed to (a) release the second active agent upon exposure to colder water and the first active agent upon exposure to warmer water such that the second active agent does not come in contact with the first active agent prior to the second active agent being released into the water or (b) release the first active agent from the first interior pouch volume prior to substantial dissolution of the nonwoven web such that the first active agent and the second active agent will come into contact/mix in the second interior pouch prior to either composition being substantially released from the unit dose.

Additional contemplated applications can include those wherein the composition contained in the unit dose can become stale or otherwise unsuitable over time when exposed to, e.g., oxygen, and otherwise require release of the extract of the composition upon use. Such applications can include, but are not limited to, tea leaves and pouched tobacco products. Advantageously, the unit dose of the disclosure can provide a gas barrier in the water soluble film to maintain freshness, which can dissolve at the point of use (e.g., hot water or placement in the mouth of consumer and contacted with saliva), allowing the release of the extract (e.g., caffeine, flavor, and/or tobacco extracts) while keeping the solid portions of the composition (e.g., leaves) contained within the non-water soluble, biodegradable or compostable, nonwoven web. The nonwoven web can then be disposed of as appropriate and allowed to biodegrade or compost.

An aspect of the disclosure herein provides a method of exfoliating human skin using the unit dose article of the disclosure. In embodiments, the method can comprise contacting the unit dose article with human skin and then exfoliating the human skin.

Sealed Pouches

The disclosure further provides a unit dose article comprising a water soluble film of the disclosure in the form of a pouch defining a first interior pouch volume, and a nonwoven web according to the disclosure in the form of a pouch and encompassing the water soluble film. In some embodiments, the pouch can include a laminate comprising the water-soluble film and the nonwoven web. The disclosure further provides a method of preparing a unit dose article of the disclosure, the method comprising forming the water soluble film into an open pouch defining an open pouch volume; adding the first composition into the open pouch volume; and sealing the film to form the first interior pouch volume. In some embodiments, sealing includes heat sealing, solvent sealing, adhesive sealing, or a combination thereof. In embodiments, the nonwoven web is laminated to the water soluble film prior to forming the water soluble film into a pouch. In embodiments, the water soluble film is formed into a pouch, followed by laminating the nonwoven web and the water soluble film.

The nonwoven webs and laminates disclosed herein are useful for creating a sealed article in the form of a pouch defining an interior pouch volume to contain a first composition therein for release into an aqueous environment. A "sealed article" optionally encompasses sealed compartments having a vent hole, for example, in embodiments wherein the compartment encloses a solid that off-gasses, but more commonly will be a completely sealed compartment.

Additionally, the auxiliary agents can be added to the surface of pouches.

The unit dose article comprises one or more compartments. A unit dose article disclosed herein can be formed from two layers of nonwoven web and two layers of water soluble film or two layers of laminate sealed at an interface, or by a single nonwoven web and a single water soluble film or a single laminate that is folded upon itself and sealed. The nonwoven web and water soluble film or laminate forms at least one side wall of the pouch, optionally the entire pouch, and preferably an outer surface of the at least one sidewall. In another type of embodiment, the nonwoven web and the water soluble film or laminate forms an inner wall of the packet, e.g. as a dividing wall between compartments. The nonwoven web and the water soluble film or laminate can also be used in combination with a water-soluble film, e.g., as an exterior wall, inner wall, and/or compartment lid.

In embodiments, the unit dose article of the disclosure can comprise two compartments. In embodiments, the unit dose article of the disclosure can comprise three compartments. In embodiments wherein the unit dose article comprises at least two compartments, at least one nonwoven web pouch is not water soluble. In embodiments wherein the unit dose article comprises at least two compartments, at least a portion of one nonwoven web pouch is soluble in water at a temperature in a range of about 10° C. to about 20° C. according to MSTM 205. In embodiments wherein the unit dose article comprises at least two compartments, at least a portion of one nonwoven web pouch is not soluble in water at a temperature of about 30° C. or less according to MSTM 205, according to MSTM 205. In embodiments wherein the unit dose article comprises at least two compartments, at least a portion of one nonwoven web pouch is soluble in water at a temperature in a range of about 10° C. to about 20° C. according to MSTM 205 and at least a portion of one nonwoven web pouch is not soluble in water at a temperature of about 30° C. or less according to MSTM 205, according to MSTM 205.

The composition contained in the pouch is not particularly limited, for example including any of the variety of compositions described herein. In embodiments comprising multiple compartments, each compartment may contain identical and/or different compositions. In turn, the compositions may take any suitable form including, but not limited to liquid, solid, gel, paste, mull, pressed solids (tablets) and combinations thereof (e.g. a solid suspended in a liquid). In embodiments, each compartment may contain identical and/or different personal care compositions, for example, a unit dose article comprising one compartment comprising a surfactant and a different compartment comprising enzymes. In embodiments wherein the composition is a liquid, the liquid is contained by the film and/or laminate.

In some embodiments, the unit dose articles comprise multiple compartments. The multiple compartments outlay is not particularly limited, the multiple compartments can be, but not limited to, superposed such that the compartments share a partitioning wall interior to the pouch or the compartments can be side by side. The compartments of multi-compartment pouches may be of the same or different size(s) and/or volume(s). The compartments of the present multi-compartment pouches can be separate or conjoined in any suitable manner. In embodiments, the second and/or third and/or subsequent compartments are superimposed on the first compartment. In one embodiment, the third compartment may be superimposed on the second compartment, which is in turn superimposed on the first compartment in a sandwich configuration. Alternatively, the second and third compartments may be superimposed on the first compartment. However, it is also equally envisaged that the first, the second and/or third and/or subsequent compartments are orientated side-by-side or in concentric orientations. The compartments may be packed in a string, each compartment being individually separable by a perforation line. Hence each compartment may be individually torn-off from the remainder of the string by the end-user. In some embodiments, the first compartment may be surrounded by at least the second compartment, for example in a tire-and-rim configuration, or in a pouch-in-a-pouch configuration. In embodiments, the unit dose article comprises a second compartment comprising one or more of a water soluble film and a nonwoven web in the form of a pouch defining an interior pouch volume. In embodiments, the unit dose article comprises a third compartment comprising one or more of a water soluble film in the form of a pouch defining an interior pouch volume. In embodiments, at least one compartment is formed by a nonwoven web that is not water soluble. In embodiments, at least one compartment is formed by a nonwoven web that is soluble in water at a temperature in a range of about 0° C. to about 20° C. according to MSTM 205. In embodiments, at least one compartment is formed by a nonwoven web wherein at least a portion of the nonwoven web is not soluble in water at a temperature of 20° C. or less according to MSTM 205. In embodiments, at least one compartment is formed by a nonwoven web and a water soluble film in the form of a laminate. In embodiments, the unit dose article comprises two compartments that are provided in a side by side configuration. In embodiments, the unit dose article comprises two compartments that are superposed. In embodiment the unit dose article comprises three compartments that are superposed, such as seen in FIG. 4. FIG. 4 shows a superposed unit dose article 1, wherein compartments 3 and 4 are provided in a side by side configuration and are superposed on compartment 2.

The geometry of the compartments may be the same or different. In embodiments the optionally third and subsequent compartments each have a different geometry and shape as compared to the first and second compartment. In these embodiments, the optionally third and subsequent compartments are arranged in a design on the first or second compartment. The design may be decorative, educative, or illustrative, for example to illustrate a concept or instruction, and/or used to indicate origin of the product.

Methods of Making Unit Dose Articles

The unit dose articles comprising pouches and packets may be made using any suitable equipment and method. For example, single compartment pouches may be made using vertical form filling, horizontal form filling, or rotary drum filling techniques commonly known in the art. Such processes may be either continuous or intermittent. The layered nonwoven web, film, or laminate structure may be dampened, and/or heated to increase the malleability thereof. The method may also involve the use of a vacuum to draw the layered nonwoven web, film, or laminate structure into a suitable mold. The vacuum drawing the nonwoven web, film, or laminate into the mold can be applied for about 0.2 to about 5 seconds, or about 0.3 to about 3, or about 0.5 to about 1.5 seconds, once the layered nonwoven web, film, or laminate structure is on the horizontal portion of the surface. This vacuum can be such that it provides an under-pressure in a range of 10 mbar to 1000 mbar, or in a range of 100 mbar to 600 mbar, for example.

The disclosure further provides a method of preparing a unit dose article of the disclosure, the method comprising forming the water soluble film into an open pouch defining an open pouch volume; adding the first composition into the open pouch volume; and sealing the film to form the first interior pouch volume. In some embodiments, sealing includes heat sealing, solvent sealing, adhesive sealing, or a combination thereof. In embodiments, the forming of the water soluble film into the open pouch defining the open pouch volume comprises co-thermoforming the water soluble film and the nonwoven web such that the water soluble film and the nonwoven web form a laminate during pouch formation. In embodiments, laminating the water soluble film and nonwoven web prior to forming the water soluble film into the open pouch defining the open pouch volume. In embodiments, the sealing the film to form the first interior pouch volume comprises positioning a second water soluble film and second nonwoven web over the portion of the pouch that is open and sealing the second water soluble film and nonwoven web to the water soluble film in the form of the open pouch, wherein the second water soluble film and second nonwoven web are configured such that the second water soluble film is adjacent to the open pouch volume and the second water soluble film forms an exterior surface of the pouch.

The molds, in which packets may be made, can have any shape, length, width and depth, depending on the required dimensions of the pouches. The molds may also vary in size and shape from one to another, if desirable. For example, the volume of the final pouches may be about 5 ml to about 300 ml, or about 10 ml to 150 ml, or about 20 ml to about 100 ml, and that the mold sizes are adjusted accordingly.

Thermoforming

A thermoformable nonwoven web, film, or laminate is one that can be shaped through the application of heat and a force. Thermoforming a nonwoven web, film, or laminate structure is the process of heating the nonwoven web, film, or laminate structure, shaping it (e.g. in a mold), and then allowing the resulting nonwoven web, film, or laminate to cool, whereupon the nonwoven web, film, or laminate will hold its shape, e.g. the shape of the mold. The heat may be applied using any suitable means. For example, the nonwoven web, film, or laminate may be heated directly by passing it under a heating element or through hot air, prior to feeding it onto a surface or once on a surface. Alternatively, it may be heated indirectly, for example by heating the surface or applying a hot item onto the nonwoven web, film, or laminate. In embodiments, the nonwoven web, film, or laminate is heated using an infrared light. The nonwoven web, film, or laminate may be heated to a temperature in a range of about 50 to about 150° C., about 50 to about 120° C., about 60 to about 130° C., about 70 to about 120° C., or about 60 to about 90° C. Thermoforming can be performed by any one or more of the following processes: the manual draping of a thermally softened nonwoven web, film, or laminate over a mold, or the pressure induced shaping of a softened nonwoven web, film, or laminate to a mold (e.g., vacuum forming), or the automatic high-speed indexing of a freshly extruded sheet having an accurately known temperature into a forming and trimming station, or the automatic placement, plug and/or pneumatic stretching and pressuring forming of a nonwoven web, film, or laminate.

Alternatively, the nonwoven web, film, or laminate can be wetted by any suitable means, for example directly by spraying a wetting agent (including water, a polymer composition, a plasticizer for the nonwoven web, film, or laminate composition, or any combination of the foregoing) onto the nonwoven web, film, or laminate, prior to feeding it onto the surface or once on the surface, or indirectly by wetting the surface or by applying a wet item onto the nonwoven web, film, or laminate.

Once a nonwoven web, film, or laminate has been heated and/or wetted, it may be drawn into an appropriate mold, preferably using a vacuum. The filling of the molded nonwoven web, film, or laminate can be accomplished by utilizing any suitable means. In embodiments, the most preferred method will depend on the product form and required speed of filling. In embodiments, the molded nonwoven web, film, or laminate is filled by in-line filling techniques. The filled, open packets are then closed forming the pouches, using a second nonwoven web, film, or laminate, by any suitable method. This may be accomplished while in horizontal position and in continuous, constant motion. The closing may be accomplished by continuously feeding a second nonwoven web, film, or laminate, over and onto the open packets and then sealing the first and second nonwoven web, film, or laminate together, typically in the area between the molds and thus between the packets.

Sealing

Any suitable method of sealing the packet and/or the individual compartments thereof may be utilized. Non-limiting examples of such means include heat sealing, solvent welding, solvent or wet sealing, and combinations thereof. Typically, only the area which is to form the seal is treated with heat or solvent. The heat or solvent can be applied by any method, typically on the closing material, and typically only on the areas which are to form the seal. If solvent or wet sealing or welding is used, it may be preferred that heat is also applied. Preferred wet or solvent sealing/welding methods include selectively applying solvent onto the area between the molds, or on the closing material, by for example, spraying or printing this onto these areas, and then applying pressure onto these areas, to form the seal. Sealing rolls and belts (optionally also providing heat) can be used, for example.

In embodiments, an inner nonwoven web, film, or laminate is sealed to outer nonwoven web(s), film(s), or laminate(s) by solvent sealing. The sealing solution is generally an aqueous solution. In embodiments, the sealing solution includes water. In embodiments, the sealing solution includes water and further includes one or more diols and/or glycols such as 1,2-ethanediol (ethylene glycol), 1,3-propanediol, 1,2-propanediol, 1,4-butanediol (tetramethylene glycol), 1,5-pantanediol (pentamethylene glycol), 1,6-hexanediol (hexamethylene glycol), 2,3-butanediol, 1,3-butanediol, 2-methyl-1,3-propanediol, various polyethylene glycols (e.g., diethylene glycol, triethylene glycol), and combinations thereof. In embodiments, the sealing solution includes erythritol, threitol, arabitol, xylitol, ribitol, mannitol, sorbitol, galactitol, fucitol, iditol, inositol, volemitol, isomal, maltitol, lactitol. In embodiments, the sealing solution includes a water-soluble polymer.

The sealing solution can be applied to the interfacial areas of the inner nonwoven web, film, or laminate in any amount suitable to adhere the inner and outer nonwoven webs or laminates. As used herein, the term "coat weight" refers to the amount of sealing solution applied to the nonwoven web, film, or laminate in grams of solution per square meter of nonwoven web, film, or laminate. In general, when the coat weight of the sealing solvent is too low, the nonwoven webs, films, or laminates do not adequately adhere and the risk of pouch failure at the seams increases. Further, when the coat weight of the sealing solvent is too high, the risk of the solvent migrating from the interfacial areas increases, increasing the likelihood that etch holes may form any films comprising the sides of the pouches. The coat weight window refers to the range of coat weights that can be applied to a given film or laminate while maintaining both good adhesion and avoiding the formation of etch holes. A broad coat weight window is desirable as a broader window provides robust sealing under a broad range of operations. Suitable coat weight windows are at least about 3 g/m$^2$, or at least about 4 g/m$^2$, or at least about 5 g/m$^2$, or at least about 6 g/m$^2$.

In embodiments, the sealing the pouch to form a sealed article comprises positioning a second water soluble film and second nonwoven web over the portion of the pouch that is open and sealing the second water soluble film and nonwoven web to the water soluble film in the form of a pouch. In embodiments, the second water soluble film and second nonwoven web are configured such that the second water soluble film is adjacent to the interior pouch volume and the second water soluble film forms an exterior surface of the pouch.

Cutting the Unit Dose Articles

Formed pouches may be cut by a cutting device. Cutting can be accomplished using any known method. It may be preferred that the cutting is also done in continuous manner, and preferably with constant speed and preferably while in horizontal position. The cutting device can, for example, be a sharp item, or a hot item, or a laser, whereby in the latter cases, the hot item or laser 'burns' through the film/sealing area.

Forming and Filling Multi-Compartment Unit Dose Articles

The different compartments of a multi-compartment unit dose articles comprising pouches may be made together in a side-by-side style or concentric style wherein the resulting, conjoined pouches may or may not be separated by cutting. Alternatively, the compartments can be made separately.

In embodiments, pouches may be made according to a process comprising the steps of: a) forming a first compartment (as described above); b) forming a recess within or all of the closed compartment formed in step (a), to generate a second molded compartment superposed above the first compartment; c) filling and closing the second compartments by means of a third nonwoven web, laminate, or film; d) sealing the first, second and third nonwoven web, laminate, or film; and e) cutting the nonwoven webs, films or laminates to produce a multi-compartment pouch. The recess formed in step (b) may be achieved by applying a vacuum to the compartment prepared in step (a).

In embodiments, second, and/or third compartment(s) can be made in a separate step and then combined with the first compartment as described in European Patent Application Number 08101442.5 or U.S. Patent Application Publication No. 2013/240388 A1 or WO 2009/152031.

In embodiments, pouches may be made according to a process comprising the steps of: a) forming a first compartment, optionally using heat and/or vacuum, using a first nonwoven web, film, or laminate on a first forming machine; b) filling the first compartment with a first composition; c) optionally filling the second compartment with a second composition; d) sealing the first and optional second compartment with a second nonwoven web, film, or laminate to the first nonwoven web or laminate; and e) cutting the nonwoven webs or laminates to produce a multi-compartment pouch.

In embodiments, pouches may be made according to a process comprising the steps of: a) forming a first compartment, optionally using heat and/or vacuum, using a first nonwoven web, film, or laminate on a first forming machine; b) filling the first compartment with a first composition; c) on a second forming machine, deforming a second nonwoven web, film, or laminate, optionally using heat and vacuum, to make a second and optionally third molded compartment; d) filling the second and optionally third compartments; e) sealing the second and optionally third compartment using a third nonwoven web, film, or laminate; f) placing the sealed second and optionally third compartments onto the first compartment; g) sealing the first, second and optionally third compartments; and h) cutting the nonwoven web, film, or laminate to produce a multi-compartment pouch.

The first and second forming machines may be selected based on their suitability to perform the above process. In embodiments, the first forming machine is preferably a horizontal forming machine, and the second forming machine is preferably a rotary drum forming machine, preferably located above the first forming machine.

It should be understood that by the use of appropriate feed stations, it may be possible to manufacture multi-compartment pouches incorporating a number of different or distinctive compositions and/or different or distinctive liquid, gel or paste compositions.

In embodiments, the nonwoven web, film, or laminate and/or pouch is sprayed or dusted with a suitable material, such as an active agent, a lubricant, an aversive agent, or mixtures thereof. In embodiments, the nonwoven web, film, or laminate and/or pouch is printed upon, for example, with an ink and/or an active agent.

Vertical Form, Fill and Seal

In embodiments, the nonwoven web, film, or laminate of the disclosure can be formed into a sealed article. In embodiments, the sealed article is a vertical form, filled, and sealed article. The vertical form, fill, and seal (VFFS) process is a conventional automated process. VFFS includes an apparatus such as an assembly machine that wraps a single piece of the nonwoven web, film, or laminate around a vertically oriented feed tube. The machine heat seals or otherwise secures the opposing edges of the nonwoven web, film, or laminate together to create the side seal and form a hollow tube of nonwoven web, film, or laminate. Subsequently, the machine heat seals or otherwise creates the bottom seal, thereby defining a container portion with an open top where the top seal will later be formed. The machine introduces a specified amount of flowable product into the container portion through the open top end. Once the container includes the desired amount of product, the machine advances the nonwoven web, film, or laminate to another heat sealing device, for example, to create the top seal. Finally, the machine advances the nonwoven web, film, or laminate to a cutter that cuts the film immediately above the top seal to provide a filled package.

During operation, the assembly machine advances the nonwoven web, film, or laminate from a roll to form the package. Accordingly, the nonwoven web, film, or laminate must be able to readily advance through the machine and not adhere to the machine assembly or be so brittle as to break during processing.

Pouch Contents

In any embodiment, the pouch can contain (enclose) a first composition in the defined first interior volume of the pouch. The first composition can be selected from a liquid, solid or combination thereof. In embodiments wherein the first composition includes a liquid, solid, or combination thereof, the water soluble film is in the form of a pouch defining a first interior pouch volume, the nonwoven web is in the form of a pouch defining a second interior pouch volume encompassing the water soluble film, and the first composition is contained by the water soluble film. In embodiments, the first composition is contained by the water soluble film and a second composition is disposed within the second interior pouch volume between the water soluble film pouch and the nonwoven web pouch. In embodiments wherein the second composition is a liquid and the second composition is disposed within the second interior pouch volume between the water soluble film pouch and the nonwoven web pouch, the nonwoven web can be a nonporous nonwoven web or a laminate. In embodiments wherein the second composition is a solid and the second composition is disposed between the water soluble film pouch and the nonwoven web pouch, the nonwoven web can be a porous nonwoven web. In embodiments wherein the nonwoven web pouch is porous, the porous nonwoven web can have a porosity of about 20% to about 95%, or about 30% to about 90%, or about 40% to about 80%, according to the Porosity Test Method.

In embodiments, the sealed unit dose articles of the disclosure can enclose in the first interior pouch volume, the second interior pouch volume, or both, a first composition and/or a second composition. The first and/or second compositions of the disclosure are not particularly limited, for example, personal care compositions, dish washing compositions, automotive compositions, agricultural compositions, edible compositions, and/or surface cleaning compositions. In general, the first and/or second compositions of the disclosure can comprise chemical exfoliants, mechanical exfoliants, perfume microcapsules, aversive agents, surfactants, colorants, enzymes, skin conditioners, de-oiling agents, cosmetic agents, fertilizers, ingestible compositions, or a combination thereof. In embodiments, the first and/or second composition comprises a personal care composition. The personal care composition can comprise a shampoo, a conditioner, a body wash, a face wash, a skin lotion, a skin treatment, a body oil, a fragrance, a hair treatment, a chemical exfoliant, a mechanical exfoliant, a bath salt, an essential oil, a bath bomb, an enzyme, or a combination thereof.

In further embodiments, the personal care composition can be provided as part of the plurality of fibers, dispersed within the nonwoven pouch, provided on a face of the nonwoven pouch or a combination thereof.

As used herein, "liquid" includes free-flowing liquids, as well as pastes, gels, foams and mousses.

The unit dose article and/or the nonwoven of the disclosure can advantageously prolong the release of a composition contained in the unit dose article and/or nonwoven after contact with water. The prolonged release of the composition contained within the unit dose article and/or nonwoven can be advantageous as the user of the unit dose article and/or nonwoven may desire slow release of the composition, for example, in a shower using a unit dose article and/or nonwoven with a body wash composition contained by the unit dose article and/or nonwoven. The prolonged release of the compositions can allow the user an improved experience, for example in the shower, as the unit dose article and/or nonwoven provides for the persistence of foaming, detergency, and soap to remove dirt, oil, and other foreign unwanted materials on the skin or hair, unlike traditional bulk liquid body wash, shampoo, or conditioner that rinse off quickly without residing long enough to foam and clean the skin/hair properly. The unit dose article and/or nonwoven of the disclosure provides the composition to the user for prolonged periods of time, unlike traditional personal care product delivery systems, such as bulk liquids. Such improved user experience cannot be provided by simply providing bulk soap into a conventional water soluble unit dose pod as the soap is free to rinse away as soon as the pod ruptures. In contrast, in the unit dose articles and/or the nonwovens of the disclosure, the foaming action, detergency, and soap can persist as long as the article has not dissolved, enabling the consumer to more thoroughly clean skin or hair with a single dose of cleansing agent.

In embodiments, the first and/or second composition within the unit dose article and/or the nonwoven can have prolonged release from the unit dose article and/or the nonwoven after contact with water when the unit dose article and/or the nonwoven comprises a water soluble film and nonwoven web, wherein the water soluble film is soluble in water at a temperature in a range of about 0° C. to about 20° C. according to MSTM 205 and at least a portion of the nonwoven web is not soluble in water at a temperature of less than 20° C. according to MSTM 205. In embodiments, the first and/or second composition within the unit dose article and/or the nonwoven can have prolonged release from the unit dose article and/or the nonwoven after contact with water when the unit dose article and/or the nonwoven comprises a water soluble film and nonwoven web, wherein the water soluble film is not soluble in water at a temperature of less than 20° C. according to MSTM 205 and at least a portion of the nonwoven web is not soluble in water at a temperature of less than 20° C. according to MSTM 205. In embodiments, the first and/or second composition within the unit dose article and/or the nonwoven can have prolonged release from the unit dose article and/or the nonwoven after contact with water when the unit dose article and/or the nonwoven comprises a water soluble film and nonwoven web, wherein the water soluble film is soluble in water at a temperature in a range of about 0° C. to about 20° C. according to MSTM 205 and at least a portion of the nonwoven web is soluble in water at a temperature in a range of about 0° C. to about 20° C. according to MSTM 205. In embodiments, the first and/or second composition within the unit dose article and/or the nonwoven can have prolonged release from the unit dose article and/or the nonwoven after contact with water when the unit dose article and/or the nonwoven comprises a water soluble film and nonwoven web, wherein the water soluble film is soluble in water at a temperature in a range of about 0° C. to about 20° C. according to MSTM 205 and at least a portion of the nonwoven web is not water soluble and/or biodegradable. In embodiments, the first and/or second composition within the unit dose article and/or the nonwoven can have prolonged release from the unit dose article after contact with water when the unit dose article and/or the nonwoven comprises a water soluble film and nonwoven web, wherein the water soluble film is not soluble in water at a temperature of 20° C. or less according to MSTM 205, and at least a portion of the nonwoven web is not water soluble and/or biodegradable. In refinements of the foregoing embodiments, the water soluble film and the nonwoven web are laminated.

In embodiments, the unit dose article and/or the nonwoven prolongs the release of the first composition after contact with water at a temperature in the range of greater than 20° C. to about 45° C. over a time period of about 30 seconds according to Prolonged Release Test Method A, Prolonged Release Test Method B, or Prolonged Release Test Method C. In refinements of the foregoing embodiments, the unit does article and/or the nonwoven prolongs the release of the first composition over a time period of about 30 seconds according to Prolonged Release Test Method A. In embodiments, the unit dose article and/or the nonwoven prolongs the release of the first composition after contact with water at a temperature in the range of greater than 20° C. to about 45° C. over a time period of about 1 minute according to Prolonged Release Test Method A, Prolonged Release Test Method B, or Prolonged Release Test Method C. In refinements of the foregoing embodiments, the unit does article and/or the nonwoven prolongs the release of the first composition over a time period of about 1 minute according to Prolonged Release Test Method A. In embodiments, the unit dose article and/or nonwoven prolongs release of the first composition when the unit dose article and/or nonwoven does not begin to release the first composition for at least about 1 minute according to the Liquid Release Test. In embodiments, the unit dose article and/or the nonwoven prolongs the release of the first composition after contact with water at a temperature in the range of greater than 20° C. to about 45° C. over a time period of about 2 minutes according to Prolonged Release Test Method A, Prolonged Release Test Method B, or Prolonged Release Test Method C. In refinements of the foregoing embodiments, the unit does article and/or the nonwoven prolongs the release of the first composition over a time period of about 2 minutes according to Prolonged Release Test Method A. In embodiments, the unit dose article and/or nonwoven prolongs release of the first composition when the unit dose article and/or nonwoven does not begin to release the first composition for at least about 2 minutes according to the Liquid Release Test. In embodiments, the unit dose article and/or the nonwoven prolongs the release of the first composition after contact with water at a temperature in the range of greater than 20° C. to about 45° C. over a time period of about 3 minutes according to Prolonged Release Test Method A, Prolonged Release Test Method B, or Prolonged Release Test Method C. In refinements of the foregoing embodiments, the unit does article and/or the nonwoven prolongs the release of the first composition over a time period of about 3 minutes according to Prolonged Release Test Method A. In embodiments, the unit dose article and/or nonwoven prolongs release of the first composition when the unit dose article and/or nonwoven does not begin to release the first composition for at least about 3 minutes according to the Liquid Release Test. In embodiments, the unit dose article and/or the nonwoven prolongs the release of the first composition after contact with water at a temperature in the range of greater than 20° C. to about 45° C. over a time period of about 4 minutes according to Prolonged Release Test Method A, Prolonged Release Test Method B, or Prolonged Release Test Method C. In refinements of the foregoing embodiments, the unit does article and/or the nonwoven prolongs the release of the first composition over a time period of about 4 minutes according to Prolonged Release Test Method A. In embodiments, the unit dose article and/or nonwoven prolongs release of the first composition when the unit dose article and/or nonwoven does not begin to release the first composition for at least about 4 minutes according to the Liquid Release Test. In embodiments, the unit dose article and/or the nonwoven prolongs the release of the first composition after contact with water at a temperature in the range of greater than 20° C. to about 45° C. over a time period of about 5 minutes according to Prolonged Release Test Method A, Prolonged Release Test Method B, or Prolonged Release Test Method C. In refinements of the foregoing embodiments, the unit does article and/or the nonwoven prolongs the release of the first composition over a time period of about 5 minutes according to Prolonged Release Test Method A. In embodiments, the unit dose article and/or nonwoven prolongs release of the first composition when the unit dose article and/or nonwoven does not begin to release the first composition for at least about 5 minutes according to the Liquid Release Test. In embodiments, the unit dose article and/or the nonwoven prolongs the release of the first composition after contact with water at a temperature in the range of greater than 20° C. to about 45° C. over a time period of about 10 minutes according to Prolonged Release Test Method A, Prolonged Release Test Method B, or Prolonged Release Test Method C. In refinements of the foregoing embodiments, the unit does article and/or the nonwoven prolongs the release of the first composition over a time period of about 10 minutes according to Prolonged Release Test Method A. In embodiments, the unit dose article and/or nonwoven prolongs release of the first composition when the unit dose article and/or nonwoven does not begin to release the first composition for at least about 10 minutes according to the Liquid Release Test. In embodiments, the first compartment of the unit dose article and/or nonwoven prolongs release of the first composition when the unit dose article has a liquid release time as determined according to the Liquid Release Test of least about 1.3× (1.3 times) longer compared to an identical unit dose article comprising the water soluble film in the form of a pouch and not including the nonwoven web in the form of a pouch. In embodiments, the first compartment of the unit dose article and/or nonwoven prolongs release of the first composition when the unit dose article has a liquid release time as determined according to the Liquid Release Test of least about 1.4× (1.4 times) longer compared to an identical unit dose article comprising the water soluble film in the form of a pouch and not including the nonwoven web in the form of a pouch. In embodiments, the first compartment of the unit dose article and/or nonwoven prolongs release of the first composition when the unit dose article has a liquid release time as determined according to the Liquid Release Test of least about 2× (2 times) longer compared to an identical unit dose article comprising the water soluble film in the form of a pouch and not including the nonwoven web in the form of a pouch.

Further provided herein is a unit dose article including a compartment comprising a water soluble film of the disclosure in the form of a pouch defining a first interior pouch volume, the water soluble resin comprising a polyvinyl alcohol homopolymer, a polyvinyl alcohol copolymer, or a mixture of a polyvinyl alcohol homopolymer and a polyvinyl alcohol copolymer; a nonwoven web in the form of a pouch defining a second interior pouch volume encompassing the water soluble film in the form of a pouch, the nonwoven web comprising a plurality of fibers comprising a first fiber type comprising a polyvinyl alcohol homopolymer fiber forming material having a degree of hydrolysis of about 75% to about 91%, and a second fiber type comprising one or both of a non-water soluble polyester and a polylactic acid fiber forming material, wherein the water soluble film and the nonwoven web are in the form of a laminate; and a personal care composition disposed within the first interior pouch volume.

Further provided herein is a unit dose article comprising two or more compartments comprising a water soluble film of the disclosure in the form of a pouch defining a first interior pouch volume, the water soluble film comprising a water soluble resin, the water soluble resin comprising a polyvinyl alcohol homopolymer, a polyvinyl alcohol copolymer, or a mixture of a polyvinyl alcohol homopolymer and a polyvinyl alcohol copolymer; a nonwoven web in the form of a pouch defining a second interior pouch volume encompassing the water soluble film in the form of a pouch, the nonwoven web comprising a plurality of fibers comprising a first fiber type comprising a polyvinyl alcohol homopolymer having a degree of hydrolysis of about 92% to about 99.9%, and a second fiber type comprising one or both of a non-water soluble polyester and a polylactic acid fiber forming material, wherein the water soluble film and the nonwoven web are in the form of a laminate; and a personal care composition disposed within the first interior pouch volume, and the personal care composition comprises a surfactant.

Specifically contemplated non-limiting embodiments are provided in the table below, wherein "MA PVOH" refers to a methyl acrylate polyvinyl alcohol copolymer, "MMM PVOH" refers to a monomethylmaleate polyvinyl alcohol copolymer, "PET" refers to polyethylene terephthalate, "PLA" refers to polylactic acid, "DL" refers to degree of lamination, and the remaining compositions, which are identified by viscosity and degree of hydrolysis (DH), are polyvinyl alcohol homopolymers.

| Embodiments | Water soluble film Composition | Nonwoven web Composition | Type and Degree of Lamination (%) |
|---|---|---|---|
| 1 | 2 mol % MA PVOH | — | — |
| 2 | — | 23 cPs, 88% DH PVOH | — |
| 3 | 2 mol % MA PVOH | 23 cPs, 88% DH PVOH | Calendar lamination; 25% DL |
| 4 | 2 mol % MA PVOH | 23 cPs, 88% DH PVOH | Calendar Lamination; 100% DL |
| 5 | 2 mol % MA PVOH | 23 cPs, 96% DH PVOH | N/A |
| 6 | 2 mol % MA PVOH | 23 cPs, 96% DH PVOH | Calendar lamination; 25% DL |
| 7 | 2 mol % MA PVOH | 23 cPs, 96% DH PVOH | Calendar lamination; 100% DL |
| 8 | 1.7 mol % MMM PVOH | — | — |
| 9 | 1.7 mol % MMM PVOH | 23 cPs, 88% DH PVOH | Calendar lamination; 25% DL |
| 10 | 1.7 mol % MMM PVOH | 23 cPs, 88% DH PVOH | Calendar Lamination; 100% DL |
| 11 | 1.7 mol % MMM PVOH | 23 cPs, 96% DH PVOH | Calendar lamination; 25% DL |
| 12 | 1.7 mol % MMM PVOH | 23 cPs, 96% DH PVOH | Calendar lamination; 100% DL |
| 13 | 23 cPs, 88% DH PVOH | — | — |
| 14 | 23 cPs, 88% DH PVOH | 23 cPs, 88% DH PVOH | Calendar lamination; 25% DL |
| 15 | 23 cPs, 88% DH PVOH | 23 cPs, 88% DH PVOH | Calendar Lamination; 100% DL |
| 16 | — | 23 cPs, 96% DH PVOH | — |
| 17 | 23 cPs, 88% DH PVOH | 23 cPs, 96% DH PVOH | Calendar lamination; 25% DL |
| 18 | 23 cPs, 88% DH PVOH | 23 cPs, 96% DH PVOH | Calendar lamination; 100% DL |
| 19 | 23 cPs, 88% DH PVOH | 23 cPs, 96% DH PVOH | Melt adhesion lamination; 100% DL |
| 20 | 8 cPs, 88% DH PVOH | — | — |
| 21 | 8 cPs, 88% DH PVOH | 23 cPs, 88% DH PVOH | Calendar lamination; 25% DL |
| 22 | 8 cPs, 88% DH PVOH | 23 cPs, 88% DH PVOH | Calendar lamination; 100% DL |
| 23 | 8 cPs, 88% DH PVOH | 23 cPs, 96% DH PVOH | Calendar lamination; 25% DL |
| 24 | 8 cPs, 88% DH PVOH | 23 cPs, 96% DH PVOH | Calendar lamination; 100% DL |
| 25 | 8 cPs, 88% DH PVOH | 23 cPs, 96% DH PVOH | Melt adhesion lamination; 100% DL |
| 26 | — | 75%: 23 cPs, 96% DH PVOH fibers; 25%: PET Fibers | — |
| 27 | 8 cPs, 88% DH PVOH | 75%: 23 cPs, 96% DH PVOH fibers; 25%: PET Fibers | Calendar lamination; 25% DL |
| 28 | 8 cPs, 88% DH PVOH | 75%: 23 cPs, 96% DH PVOH fibers; 25%: PET Fibers | Calendar lamination; 100% DL |
| 29 | — | 75%: 23 cPs, 96% DH PVOH fibers; 25%: PLA Fibers | |
| 30 | 8 cPs, 88% DH PVOH | 75%: 23 cPs, 96% DH PVOH fibers; 25%: PLA Fibers | Calendar lamination; 25% DL |
| 31 | 8 cPs, 88% DH PVOH | 75%: 23 cPs, 96% DH PVOH fibers; 25%: PLA Fibers | Calendar lamination; 100% DL |

Dissolution Time and Disintegration Time—MSTM-205

A nonwoven web, water-soluble film, or laminate structure can be characterized by or tested for Dissolution Time and Disintegration Time according to the MonoSol Test Method 205 (MSTM 205), a method known in the art. See, for example, U.S. Pat. No. 7,022,656. The description provided below refers to a nonwoven web, while it is equally applicable to a water-soluble film or laminate structure.

Apparatus and Materials:

600 mL Beaker

Magnetic Stirrer (Labline Model No. 1250 or equivalent)

Magnetic Stirring Rod (5 cm)

Thermometer (0 to 100° C.±1° C.)

Template, Stainless Steel (3.8 cm×3.2 cm)

Timer (0-300 seconds, accurate to the nearest second)

Polaroid 35 mm slide Mount (or equivalent)

MonoSol 35 mm Slide Mount Holder (or equivalent)

Distilled Water

For each nonwoven web, water soluble film, or laminate structure to be tested, three test specimens are cut from a nonwoven web, water soluble film, or laminate structure sample that is a 3.8 cm×3.2 cm specimen. Specimens should be cut from areas of web evenly spaced along the traverse direction of the web. Each test specimen is then analyzed using the following procedure.

Lock each specimen in a separate 35 mm slide mount.

Fill beaker with 500 mL of distilled water. Measure water temperature with thermometer and, if necessary, heat or cool water to maintain the temperature at the temperature for which dissolution is being determined, e.g., 20° C. (about 68° F.).

Mark height of column of water. Place magnetic stirrer on base of holder. Place beaker on magnetic stirrer, add magnetic stirring rod to beaker, turn on stirrer, and adjust stir speed until a vortex develops which is approximately one-fifth the height of the water column. Mark depth of vortex.

Secure the 35 mm slide mount in the alligator clamp of the 35 mm slide mount holder such that the long end of the slide mount is parallel to the water surface. The depth adjuster of the holder should be set so that when dropped, the end of the clamp will be 0.6 cm below the surface of the water. One of the short sides of the slide mount should be next to the side of the beaker with the other positioned directly over the center of the stirring rod such that the nonwoven web surface is perpendicular to the flow of the water.

In one motion, drop the secured slide and clamp into the water and start the timer. Disintegration occurs when the nonwoven web breaks apart. When all visible nonwoven web is released from the slide mount, raise the slide out of the water while continuing to monitor the solution for undissolved nonwoven web fragments. Dissolution occurs when all nonwoven web fragments are no longer visible and the solution becomes clear.

The results should include the following: complete sample identification; individual and average disintegration and dissolution times; and water temperature at which the samples were tested.

Method for Determining Single Fiber Solubility

The solubility of a single fiber can be characterized by the water breaking temperature. The fiber breaking temperature can be determined as follows. A load of 2 mg/dtex is put on a fiber having a fixed length of 100 mm. Water temperature starts at 1.5° C. and is then raised by 1.5° C. increments every 2 minutes until the fiber breaks. The temperature at which the fiber breaks is denoted as the water breaking temperature.

The solubility of a single fiber can also be characterized by the temperature of complete dissolution. The temperature of complete dissolution can be determined as follows. 0.2 g of fibers having a fixed length of 2 mm are added to 100 mL of water. Water temperature starts at 1.5° C. and is then raised by 1.5° C. increments every 2 minutes until the fiber completely dissolves. The sample is agitated at each temperature. The temperature at which the fiber completely dissolves is denoted as the complete dissolution temperature.

Diameter Test Method

The diameter of a discrete fiber or a fiber within a nonwoven web is determined by using a scanning electron microscope (SEM) or an optical microscope and an image analysis software. A magnification of 200 to 10,000 times is chosen such that the fibers are suitably enlarged for measurement. When using the SEM, the samples are sputtered with gold or a palladium compound to avoid electric charging and vibrations of the fiber in the electron beam. A manual procedure for determining the fiber diameters is used from the image (on monitor screen) taken with the SEM or the optical microscope. Using a mouse and a cursor tool, the edge of a randomly selected fiber is sought and then measured across its width (i.e., perpendicular to the fiber direction at that point) to the other edge of the fiber. A scaled and calibrated image analysis tool provides the scaling to get an actual reading in microns. For fibers within a nonwoven web, several fibers are randomly selected across the sample of nonwoven web using the SEM or the optical microscope. At least two portions of the nonwoven web material are cut and tested in this manner. Altogether at least 100 such measurements are made and then all data are recorded for statistical analysis. The recorded data are used to calculate average (mean) of the fibers, standard deviation of the fibers, and median fiber diameters.

Tensile Strength, Modulus, and Elongation Test

A nonwoven web, water-soluble film, or laminate structure characterized by or to be tested for tensile strength according to the Tensile Strength (TS) Test, modulus (or tensile stress) according to the Modulus (MOD) Test, and elongation according to the Elongation Test is analyzed as follows. The description provided below refers to a nonwoven web, while it is equally applicable to a water-soluble film or laminate structure. The procedure includes the determination of tensile strength and the determination of modulus at 10% elongation according to ASTM D 882 ("Standard Test Method for Tensile Properties of Thin Plastic Sheeting") or equivalent. An INSTRON tensile testing apparatus (Model 5544 Tensile Tester or equivalent) is used for the collection of nonwoven web data. A minimum of three test specimens, each cut with reliable cutting tools to ensure dimensional stability and reproducibility, are tested in the machine direction (MD) (where applicable) for each measurement. Tests are conducted in the standard laboratory atmosphere of 23±2.0° C. and 35±5% relative humidity. For tensile strength or modulus determination, 1"-wide (2.54 cm) samples of a nonwoven web are prepared. The sample is then transferred to the INSTRON tensile testing machine to proceed with testing while minimizing exposure in the 35% relative humidity environment. The tensile testing machine is prepared according to manufacturer instructions, equipped with a 500 N load cell, and calibrated. The correct grips and faces are fitted (INSTRON grips having model number 2702-032 faces, which are rubber coated and 25 mm wide, or equivalent). The samples are mounted into the tensile testing machine and analyzed to determine the 100% modulus (i.e., stress required to achieve 100% film elongation), tensile strength (i.e., stress required to break film), and elongation % (sample length at break relative to the initial sample length). In general, the higher the elongation % for a sample, the better the processability characteristics for the nonwoven web (e.g., increased formability into packets or pouches).

Determination of Basis Weight

Basis weight is determined according to ASTM D3776/D3776M-09a (2017). Briefly, a specimen having an area of at least 130 $cm^2$ or a number of smaller die cut specimens taken from different locations in the sample and having a total area of at least 130 $cm^2$ are cut. The specimen(s) are weighed to determine mass on a top loading analytical balance with a resolution of ±0.001 g. The balance is protected from air drafts and other disturbances using a draft shield. Specimens of fabric may be weighed together. The mass is calculated in ounces per square yard, ounces per linear yard, linear yards per pound, or grams per square meter to three significant figures.

The foregoing description is given for clearness of understanding only, and no unnecessary limitations should be understood therefrom, as modifications within the scope of the invention may be apparent to those having ordinary skill in the art.

All patents, publications and references cited herein are hereby fully incorporated by reference. In case of conflict between the present disclosure and incorporated patents, publications and references, the present disclosure should control.

Prolonged Release Test Method A

Measurement of Conductivity: A unit dose article is placed in a wire cage, and submerged in water (agitated or non-agitated) of a specified time and a specified temperature in a beaker. The time is recorded when the unit dose article is submerged in water. The conductivity of the water is constantly being monitored while the unit dose article is submerged. As the composition is released from the unit dose article, the conductivity of water will be constantly changing. When the conductivity of the water hits a plateau, the time is recorded. The time taken from the initial unit dose article submersion to the start of the conductivity plateauing correlates, respectively, to the time it takes for the unit dose article and composition to begin dissolution and reach an end point where dissolution stops because all possible dissolution has occurred. A longer time to reach this plateau of conductivity change would indicate a unit dose article with prolonged release compared to a unit dose article with a shorter time to reach such a plateau. The individual level of conductivity in this method is not necessarily indicative of any significant factor of prolonged release, as conductivity will be affected by the ingredients contained in the unit dose article and composition therein.

Prolonged Release Test Method B

Weight Loss after Unit Dose Rupture: A unit dose article is placed in a wire cage, and submerged in water (agitated or non-agitated) of a specified volume and specified temperature in a beaker. The time is recorded when the unit dose article is submerged in water. The time it takes for leakage of the contained composition from the article to first be observed is again recorded. At this point, a timer is started, and the cage containing the article is removed from the water, and suspended above the beaker, allowing the composition to release and fall into the water below. The cage would be suspended by a force meter, and the weight of the cage and article is measured to determine weight loss of the article due to the composition loss over time. This measurement is carried out such that the time taken for the article to lose a specific amount of weight is recorded (e.g. a percentage, such as 50%, of the known amount of composition contained in the article), or alternatively recording how much weight the article loses in a specific amount of time, such as 2 minutes.

Prolonged Release Test Method C

Modified Liquid Release Time Visual Observation: A unit dose article is placed in a wire cage, and submerged in water (agitated or non-agitated) of a specified volume and specified temperature in a beaker. The time is recorded when the unit dose article is submerged in water. The time it takes for leakage of the contained composition from the article to first be observed is recorded. The time it takes for the entirety of the composition to be released is also recorded.

Porosity Test Method

The method to determine porosity of a specific nonwoven utilizes a liquid saturation method and is performed as follows: A 1-inch by 1-inch test specimen is cut from a nonwoven web. The mass of the test specimen is determined using an analytical balance and recorded. The test specimen is submerged in a liquid that neither swells nor dissolves the fibers in the nonwoven specimen. The liquid sample with the submerged nonwoven specimen is then sonicated for 5 minutes to ensure complete permeation of the liquid throughout all available void space of the nonwoven specimen. After 5 minutes, the liquid sample is removed from the sonicator, and the nonwoven sample is removed with tweezers from the liquid and allowed to drip dry (time here needs to be confirmed). After drip drying is complete, the nonwoven surface is lightly dabbed with a chemwipe in order to remove excess surface liquid. Care must be taken to not absorb liquid from the bulk of the nonwoven specimen, hence a very light dab on each side should suffice. Once complete, the mass of the specimen is once again determined and recorded and the difference between the initial and final mass, that is, the mass of absorbed liquid, is calculated. From this mass, and using the liquid's known density, the volume of absorbed liquid is calculated ($L_V$). Using the initial mass of the nonwoven and its known density, the non-void space volume of the nonwoven is calculated ($N_V$). Using the two calculated volume values, the percent porosity of the nonwoven is determined via the following equation:

$$\text{Porosity (\%)}=[L_V/(L_V+N_V)]*100.$$

Softness Rating

The hand feel of a nonwoven web, laminate, or pouch of the disclosure is related to the softness of the sample and can be evaluated using relative testing methods. A tester carrying out the softness evaluation used clean hands to feel the samples in whatever manner or method the individual chose, to determine a softness rating for the nonwoven webs and articles of the disclosure as compared to a control material comprising a nonwoven web consisting of fibers consisting of polyvinyl alcohol homopolymers having a degree of hydrolysis of 88%, the fibers having a 2.2 dtex/51 mm cut, having a softness rating of 1 (softest) and a control material comprising a nonwoven web consisting of fibers consisting of 75% polyvinyl alcohol homopolymers having a degree of hydrolysis of 88%, the fibers having a 2.2/51 mm cut, and 25% of 22 dtex/38 mm PET fiber, having a softness rating of 5 (roughest/coarsest). The hand panel was conducted in a blind study so that the raters could not be swayed by their perception of sample names. Samples were rated from 1 to 5.

Liquid Release Test

FIG. 1 is an illustration of a wire frame cage (shown with the top open, to better illustrate water-soluble pouches contained therein) for use in the Liquid Release Test described herein.

Figure 2:
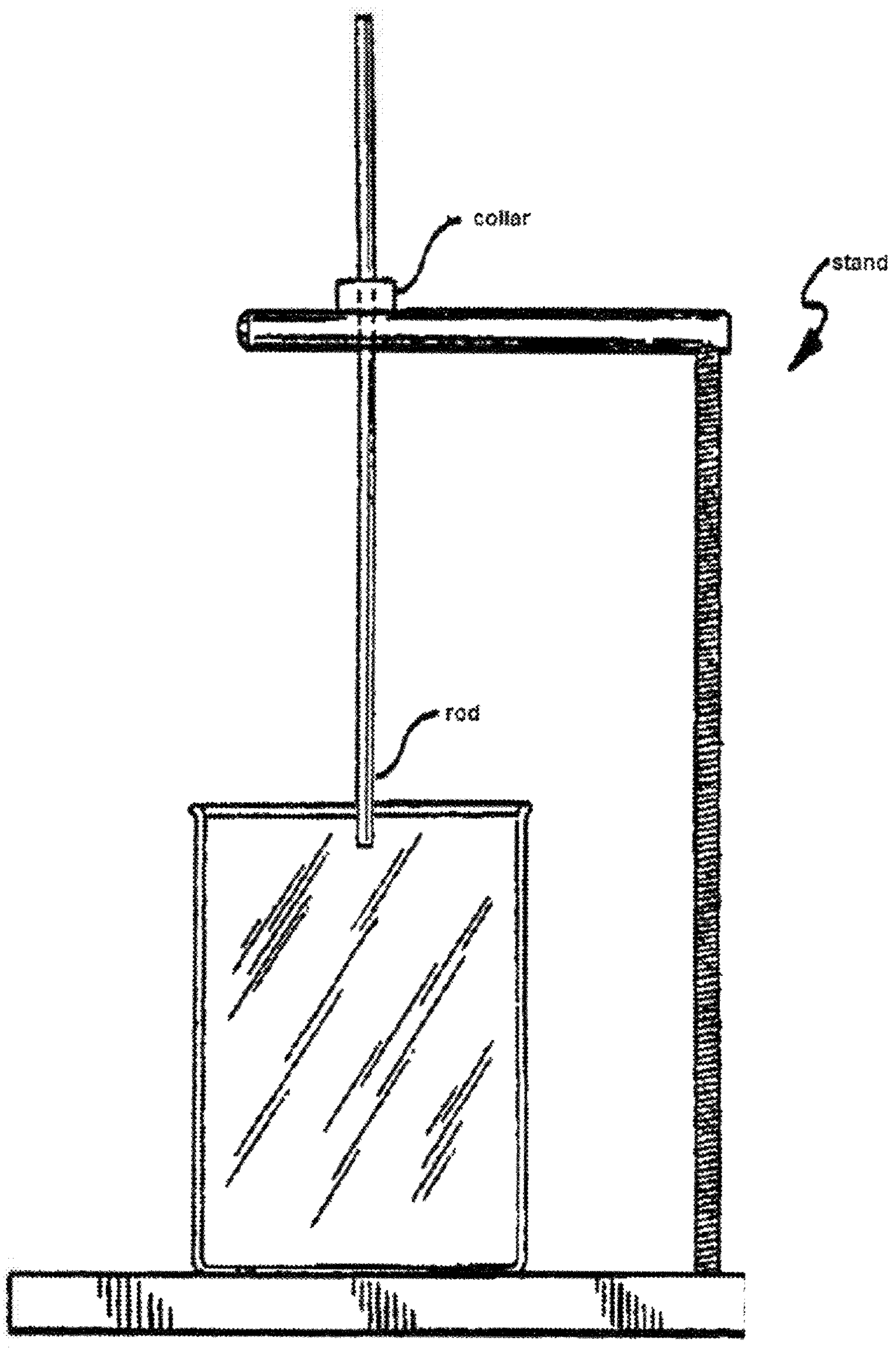
FIG. 2 shows an apparatus for performing the Liquid Release Test, including a beaker resting on a stand, the stand holding a rod for lowering a cage into the beaker, the rod being fixable by a collar with a set screw (not shown).

FIG. 2 shows an apparatus for performing the Liquid Release Test, including a beaker resting on a stand, the stand holding a rod for lowering a cage into the beaker, the rod being fixable by a collar with a set screw (not shown).

The method is generally in line with ASTM D4332-13 on Standard Practice for Conditioning Containers, Packages or Packaging Components for Testing; however, the control of 50±2% Relative Humidity is not maintained in the Liquid Release Test.

A water-soluble film, nonwoven web, and/or pouch characterized by or to be tested for delayed solubility according to the Liquid Release Test is analyzed as follows using the following materials:

- 2 L beaker and 6 liters of deionized (DI) water (enough to repeat the test 5 times)
- Water-soluble pouch to be tested; the pouch is preconditioned for two weeks at 23±1° C. and 50±4% Relative Humidity for at least 24 hours; for results to be comparative, all films tested should have the same thickness, for example, 88 μm or 76 μm; and all nonwovens should have the same basis weight, for example, 50 gsm.

Thermometer

- Wire cage
- Timer

Before running the experiment, ensure that enough DI water is available to repeat the experiment five times, and ensure that the wire cage, beaker, and clamp are clean and dry.

The wire frame cage is a plastic coated wire cage (10 cm×8.9 cm×6.4 cm) with no sharp edges, or equivalent. The gauge of the wire should be about 1.25 mm and the wire should have openings the size of 0.5 inch (1.27 cm) squares. An example image of a cage 28 with test pouches 30 is shown in FIG. 1.

To set up for the test, carefully place the water-soluble pouch in the cage while not scratching the pouch on the cage and allowing free space for the pouch to move. Do not bind the pouch tightly with the wire cage, while still ensuring it is secure and will not come out of the cage. The orientation of the pouch in the cage should be such that the natural buoyancy of the pouch, if any, is allowed (i.e. the side of the pouch that will float to the top should be placed towards the top). If the pouch is symmetrical, the orientation of the pouch generally would not matter.

Next, fill the 2 L beaker with 1200 milliliters of 20° C. DI water.

Next, lower the wire frame cage with the contained pouch into the water. Ensure that the cage is 1 inch (2.54 cm) from the bottom of the beaker. Be sure to fully submerge the pouch on all sides. Ensure that the cage is stable and will not move and start a timer as soon as the pouch is lowered into the water. The position of the cage with respect to the water in the beaker can be adjusted and maintained by any suitable means, for example by using a clamp fixed above the beaker, and a rod attached to the top of the cage. The clamp can engage the rod to fix the position of the cage, and tension on the clamp can be lowered in order to lower the cage into the water. Other means of frictional engagement can be used in the alternative to a clamp, for example a collar with a set screw, as shown in FIG. 2 (set screw not shown). FIG. 2 shows a beaker 30 resting on a stand 40, the stand holding a rod 50 for lowering a cage 10 (not shown) into the beaker 30, the rod 50 being able to hold a fixed vertical position by use of a collar 60 having a set screw (not shown) that engages the rod 50, for example by friction or by engagement with a hole (not shown) in the rod 50.

Liquid content release is defined as the first visual evidence of the liquid leaving the submerged pouch. The liquid release time can generally be correlated with the extended release time of a liquid content from a pouch of the disclosure. In general, as the liquid release time increases, the extended release time also increases. For pouches containing compositions such as cleaning compositions and detergents that include a surfactant that can create a lather, without intending to be bound by theory, it is believed that the liquid release time correlates with the lathering/foaming time; for example, the longer the liquid release time, the longer the resulting lather/foam will be sustained.

EXAMPLES

Example 1—Preparation of Unit Dose Articles

Unit dose articles of the examples below were prepared by the following heat sealing process with the following parameters:

TABLE 1

| Forming | | Sealing | |
|---|---|---|---|
| Temperature (° C.) | 105 | Temperature (° C.) | 165 |
| Force (bar) | 0.4 | Force (bar) | 3.0 |
| Preheat Time (s) | 2.5 | Sealing Time (s) | 1.5 |
| Vacuum Time (s) | 2.5 | Vacuum Pressure: −400 mbar | |
| Air Blast Time (s) | 1.5 | | |

The films, nonwoven webs, or laminates to be thermoformed are overlaid on the cavity of interest. If the material to be thermoformed is a laminate, the nonwoven web is laid down in contact with the mold and the water soluble film is face up. For this study, the cavity was fixed at 50 mm×50 mm×12 mm Thermoforming is performed at conditions described in Table 1. Liquid laundry detergent (LLD) is added to the thermoformed cavity (nominally 15 mL). Suitable liquid laundry detergents (LLD) for testing the compatibility of the water-soluble films described herein with liquid laundry detergents are described in Tables 2 and 3 below. Without intending to be bound by theory, it is believed that low molecular weight polyols, such as propylene glycol, in liquid laundry detergents can migrate into the film or fiber and interact with the polymers therein to decrease the crystallinity of the polymers and increase the solubility of the unit dose article in water. In general, as the amount of low molecular weight polyols in a liquid laundry detergent increases the unit dose article containing the liquid laundry detergent becomes more readily soluble (i.e., the solubility temperature decreases and/or solubility time decreases). The cap material is then overlaid on the filled, thermoformed unit dose article. If the material that was thermoformed is a laminate, the water soluble film side is placed in contact with the encapsulated composition and nonwoven web side is on the exterior of the unit dose article, facing away from the encapsulated composition. The unit dose article is then sealed using heat and pressure as described in Table 1.

TABLE 2

| LLD One | Wt % |
|---|---|
| Monoethanolamine | 8-9% |
| Dodecylbenzenesulfonic Acid | 22-26% |
| Oleic Acid | 18-21% |
| Lauryl Alcohol Ethoxylate | 22-26% |
| Propylene Glycol | 8-11% |
| Diethylene Glycol | 8-11% |
| Water | 4-7% |

TABLE 3

| LLD Two | Wt % |
|---|---|
| Monoethanolamine | 8-9% |
| Dodecylbenzenesulfonic Acid | 22-26% |
| Oleic Acid | 18-21% |
| Lauryl Alcohol Ethoxylate | 22-26% |
| Propylene Glycol | 5-7% |
| Diethylene Glycol | 5-7% |
| Glycerin | 5-7% |
| Water | 4-8% |

Example 2

Materials and methods: The nonwoven webs of the pouches of this example were fixed at about 40-50 gsm and the water soluble films the pouches of this example were fixed at about 3 mil. The nonwoven webs were comprised of a 50/50 blend of 1.7 dtex/38 mm cut length fibers and 2.2 dtex/51 mm cut length fibers. The samples were all unit dose articles as made by the process of Example 1. Water soluble films having 2 mol % methyl acrylate (MA) PVOH further included about 43 phr plasticizer amount. Water soluble films having 1.7% monomethyl maleate (MMM) PVOH further included about 20 phr plasticizer amount. Water soluble films having a PVOH homopolymer with 23 cPs viscosity and 88% DH further included about 26 PHR plasticizer amount. Water soluble films having a PVOH homopolymer with 8 cPs viscosity and 88% DH further included about 15 phr. The pouches are described in Table 4, below. The pouches were tested for liquid release time and softness and the resulting values are provided in Table 4.

TABLE 4

| Sample | Water soluble film Composition | Nonwoven web Composition | Type and Degree of Lamination (%) | Liquid release time @ 23 (s) | Comparative Liquid Release times @ 23 (s)[1] | Softness rating (1-5) |
|---|---|---|---|---|---|---|
| 1 | 2 mol % MA PVOH | — | — | 61 | 1× | N/A |
| 2 | — | 23 cPs, 88% DH PVOH | — | 0 | — | 2 |
| 3 | 2 mol % MA PVOH | 23 cPs, 88% DH PVOH | Calendar lamination; 25% DL | 115 | 1.9× | 2 |
| 4 | 2 mol % MA PVOH | 23 cPs, 88% DH PVOH | Calendar Lamination; 100% DL | 167 | 2.7× | 3 |
| 5 | 2 mol % MA PVOH | 23 cPs, 96% DH PVOH | N/A | 0 | — | 2 |
| 6 | 2 mol % MA PVOH | 23 cPs, 96% DH PVOH | Calendar lamination; 25% DL | 203 | 3.3× | 2 |
| 7 | 2 mol % MA PVOH | 23 cPs, 96% DH PVOH | Calendar lamination; 100% DL | 263 | 4.3× | 3 |
| 8 | 1.7 mol % MMM PVOH | — | — | 45 | 1× | N/A |
| 9 | 1.7 mol % MMM PVOH | 23 cPs, 88% DH PVOH | Calendar lamination; 25% DL | 158 | 3.5× | 2 |
| 10 | 1.7 mol % MMM PVOH | 23 cPs, 88% DH PVOH | Calendar Lamination; 100% DL | 211 | 4.7× | 3 |
| 11 | 1.7 mol % MMM PVOH | 23 cPs, 96% DH PVOH | Calendar lamination; 25% DL | 136 | 3.0× | 2 |
| 12 | 1.7 mol % MMM PVOH | 23 cPs, 96% DH PVOH | Calendar lamination; 100% DL | 245 | 5.6× | 3 |
| 13 | 23 cPs, 88% DH PVOH | — | — | 32 | 1× | N/A |
| 14 | 23 cPs, 88% DH PVOH | 23 cPs, 88% DH PVOH | Calendar lamination; 25% DL | 197 | 6.1× | 2 |
| 15 | 23 cPs, 88% DH PVOH | 23 cPs, 88% DH PVOH | Calendar Lamination; 100% DL | 336 | 10.5× | 3 |
| 16 | — | 23 cPs, 96% DH PVOH | — | 0 | — | 2 |
| 17 | 23 cPs, 88% DH PVOH | 23 cPs, 96% DH PVOH | Calendar lamination; 25% DL | 178 | 5.6× | 2 |
| 18 | 23 cPs, 88% DH PVOH | 23 cPs, 96% DH PVOH | Calendar lamination; 100% DL | 379 | 11.8× | 3 |
| 19 | 23 cPs, 88% DH PVOH | 23 cPs, 96% DH PVOH | Melt adhesion lamination; 100% DL | 715 | 22.3× | 2 |
| 20 | 8 cPs, 88% DH PVOH | — | — | 30 | 1× | N/A |
| 21 | 8 cPs, 88% DH PVOH | 23 cPs, 88% DH PVOH | Calendar lamination; 25% DL | 58 | 1.9× | 2 |
| 22 | 8 cPs, 88% DH PVOH | 23 cPs, 88% DH PVOH | Calendar lamination; 100% DL | 108 | 3.6× | 3 |
| 23 | 8 cPs, 88% DH PVOH | 23 cPs, 96% DH PVOH | Calendar lamination; 25% DL | 125 | 4.2× | 2 |
| 24 | 8 cPs, 88% DH PVOH | 23 cPs, 96% DH PVOH | Calendar lamination; 100% DL | 214 | 7.1× | 3 |
| 25 | 8 cPs, 88% DH PVOH | 23 cPs, 96% DH PVOH | Melt adhesion lamination; 100% DL | 416 | 13.9× | 2 |
| 26 | — | 75%: 23 cPs, 96% DH PVOH fibers; 25%: PET Fibers | — | 0 | — | 4 |
| 27 | 8 cPs, 88% DH PVOH | 75%: 23 cPs, 96% DH PVOH fibers; 25%: PET Fibers | Calendar lamination; 25% DL | 89 | 3.0× | 4 |

TABLE 4-continued

| Sample | Water soluble film Composition | Nonwoven web Composition | Type and Degree of Lamination (%) | Liquid release time @ 23 (s) | Comparative Liquid Release times @ 23 (s)[1] | Softness rating (1-5) |
|---|---|---|---|---|---|---|
| 28 | 8 cPs, 88% DH PVOH | 75%: 23 cPs, 96% DH PVOH fibers; 25%: PET Fibers | Calendar lamination; 100% DL | 116 | 3.9× | 4 |
| 29 | — | 75%: 23 cPs, 96% DH PVOH fibers; 25%: PLA Fibers | — | 0 | — | 5 |
| 30 | 8 cPs, 88% DH PVOH | 75%: 23 cPs, 96% DH PVOH fibers; 25%: PLA Fibers | Calendar lamination; 25% DL | 43 | 1.4× | 5 |
| 31 | 8 cPs, 88% DH PVOH | 75%: 23 cPs, 96% DH PVOH fibers; 25%: PLA Fibers | Calendar lamination; 100% DL | 121 | 4.0× | 5 |

[1]Comparison of the liquid release times of the water soluble film alone to its counterpart unit dose article comprising the same water soluble film further laminated with a nonwoven.

MA: methyl acrylate;

DH: degree of hydrolysis;

DL: degree of lamination;

MMM: monomethyl maleate;

PLA: polylactic acid;

PET: polyester.

Resins identified by viscosity and DH are all polyvinyl alcohol homopolymers.

The unit dose articles in Table 4 have been tested for their dissolution, softness and liquid release times. The unit dose articles comprising a laminate were compared to unit dose articles with only water soluble films or only nonwoven webs to determine the effect of Liquid release time, dissolution, and softness, of lamination. The results are shown in Table 4.

It was found that in general, calendar laminated unit dose articles with a DL of 25% advantageously showed increased release times compared to their water soluble film only unit dose article counterparts. For example, comparing Samples 1, 3 and 6, wherein sample 1 was a unit dose article including only the water soluble film, sample 3 was a unit dose article including a 25% calendar laminated laminate, wherein the laminate included the same water soluble film as in sample 1, and sample 6 was a unit dose article including a 25% calendar laminated laminate, wherein the laminate included the same water soluble film as in sample 1 and 3, but with a different nonwoven laminated to it compared to sample 3 demonstrates that the addition of a nonwoven to the film to form a laminate increases the liquid release time and, further, that the type of fiber used to form the nonwoven of the laminate also had an effect on the liquid release time. In particular, it was found that samples 3 and 6 advantageously had liquid release times of about 1.9 times and 2.7 times, respectively, longer than the pouch comprising only the water soluble film. In addition, sample 3 and sample 6 differ in the nonwoven fibers that were used in each independent laminate. In particular, sample 6 included fibers having a higher degree of hydrolysis than the fibers of sample 3. The liquid release time of sample 6 was longer than sample 3 (3.3 times longer than the comparative film pouch and 2.7 times longer than the comparative film pouch, respectively). This difference demonstrates that the selection of fiber of the nonwoven web can advantageously provide tunable liquid release times.

Further, it was found that in general, calendar laminated unit dose articles with a DL of 100% demonstrated increased release times compared to both the 25% DL calendar laminated unit dose article and water soluble film only unit dose article counterparts. For example, comparing Samples 8-10, wherein sample 8 was a unit dose article including only the water soluble film, sample 9 was a unit dose article including a 25% calendar laminated nonwoven web, and sample 10 was a unit dose article including a 100% calendar laminated nonwoven web, wherein the nonwoven web was the same as in sample 9, but calendared at 100%, demonstrated an increase in the liquid release time with increasing degree of lamination. It was found that sample 10 had an increased liquid release time that was 4.7 times longer than the film only pouch, compared to sample 9, which had an increased liquid release time of 3.7 times longer than the film only pouch. This difference demonstrates that the selection of the degree of lamination can advantageously be used to provide tunable liquid release times.

It was further found that the softness of the unit dose article including laminates can be tuned based on the nonwoven fiber that are used and/or the degree of lamination. For example, samples 17 and 18 are both unit dose articles including laminates with identical in water soluble films and nonwoven webs, however they differ in their degree of lamination. Sample 17 had a degree of lamination of 25% that resulted in a softness rating of 2, whereas sample 18 had a degree of lamination of 100% that resulted in a softness rating of 3. Thus demonstrating that as the degree of lamination increases, the softness value increases (where a higher softness value denotes a less-soft article). This difference demonstrates that the selection of the degree of lamination can advantageously be used to provide tunable softness. Further, it was found that the softness can be tuned based on the selection of fiber. For example, unit dose article samples that were laminates having a degree of lamination of 25% including only 23 cPs and 96% DH nonwoven fibers as the sole fibers had softness ratings of 2 (e.g., samples 6, 11, and 17). However, when fibers having shorter lengths and wider diameters were included, the softness values of the resulting articles increased. For example, sample 27 and 30 included 75% of a the same fiber type used in samples 6, 11, and 17, but also included 25% of a polyester fiber with 6 dpf×51 mm or 25% of a polylactic acid fiber with 6.6 dtex×60 mm, respectively. This resulted in samples 27 and 30 having an increased softness rating of 4 and 5, respectively. Articles with such softness ratings can advantageously be used in personal care articles where the rougher surface can provide a mechanical exfoliating effect. This difference demonstrates that the selection of the fiber, and in particular, the L/D ratio of the fiber, can advantageously to provide tunable softness to the articles.

The unit dose articles in Table 4 that included a water soluble fiber and a non-water soluble fiber, samples 26-31, showed similar trends to the unit dose articles having a single fiber type. The liquid release times can advantageously be tuned based on the degree of lamination. In general, the higher the degree of lamination, the higher the liquid release times were for the laminated samples. For example, samples 28 and 31 were calendar laminated with a 100% degree of lamination, and have liquid release times of 116 and 121, respectively. Samples 27 and 30 were calendar laminated with a 25% degree of lamination, and have liquid release times of 89 and 43, respectively. It is expected that articles wherein the nonwoven web includes a water soluble fiber and non-water soluble fiber will also follow the above trends with respect to (a) increased release times as the degree of hydrolysis of the water soluble fiber is increases and (b) increased softness values with increased degree of lamination.

What is claimed:

1. A unit dose article comprising a compartment, the unit dose article comprising:

- a water soluble film in the form of a first pouch defining a first interior pouch volume, the water soluble film comprising a water soluble resin comprising a polyvinyl alcohol homopolymer, a polyvinyl alcohol copolymer, or a mixture of a polyvinyl alcohol homopolymer and a polyvinyl alcohol copolymer;
- a nonwoven web in the form of a second pouch defining a second interior pouch volume encompassing the water soluble film in the form of a pouch, the nonwoven web comprising a plurality of fibers comprising a first fiber type comprising a polyvinyl alcohol homopolymer fiber forming material having a degree of hydrolysis of about 75% to about 91%, and a second fiber type comprising one or both of a non-water soluble polyester and a polylactic acid fiber forming material, wherein the water soluble film and the nonwoven web are in the form of a laminate; and
- a personal care composition disposed within the first interior pouch volume, the personal care composition comprising a surfactant.

2. The unit dose article of claim 1, wherein at least a portion of the nonwoven web is not water soluble.

3. The unit dose article of claim 2, wherein the non-water soluble fiber forming material comprises one or more materials in a group of: cotton, hemp, jute, flax, ramie, sisal, bagasse, banana, lacebark, silk, sinew, catgut, wool, sea silk, mohair, angora, cashmere, collagen, actin, nylon, dacron, rayon, bamboo, modal, cellulose diacetate, cellulose triacetate, polyvinyl alcohol homopolymer, and polyvinyl alcohol copolymer.

4. The unit dose article of claim 1, wherein at least a portion of the nonwoven web is soluble in water at a temperature in a range of about 0° C. to about 20° C. according to MonoSol Test Method 205 (MSTM 205).

5. The unit dose article of claim 1, wherein at least a portion of the nonwoven web is not water soluble at a water temperature of 20° C. or less according to MSTM 205.

6. The unit dose article of claim 1, wherein the nonwoven web has a linear mass density in a range of about 1 dtex to about 5 dtex.

7. The unit dose article of claim 1, wherein the nonwoven web is biodegradable.

8. The unit dose article of claim 1, wherein the nonwoven web further comprises one or more of the group of: a chemical exfoliant, a mechanical exfoliant, a perfume microcapsule, an aversive agent, a surfactant, a colorant, an enzyme, a skin conditioner, a de-oiling agent, and a cosmetic agent dispersed among the fibers, dispersed on a face of the nonwoven web, or a combination thereof.

9. The unit dose article of claim 8, wherein the mechanical exfoliant comprises one or more exfoliants in the group of: apricot shells, sugar, oatmeal, salt, silica, diatomaceous earth, clay, aluminum hydrates, polyvinyl alcohol microbeads, and pumice.

10. The unit dose article of claim 8, wherein the chemical exfoliant comprises one or more exfoliants in the group of: an alpha hydroxyl acid, a beta hydroxyl acid, an enzyme, salicylic acid, glycolic acid, citric acid, and malic acid.

11. The unit dose article of claim 1, wherein the personal care composition disposed within the first interior pouch volume comprises one or more of the group of: a chemical exfoliant, a mechanical exfoliant, a perfume microcapsule, a aversive agent, a surfactant, a colorant, an enzyme, a skin conditioner, a de-oiling agent, a cosmetic agent, an ingestible ingredient, and a fertilizer.

12. The unit dose article of claim 1, wherein the first composition comprises a liquid.

13. The unit dose article of claim 1, wherein the first composition comprises a personal care composition comprising one or more compositions in the group of: a shampoo, a conditioner, a body wash, a face wash, a skin lotion, a skin treatment, a body oil, fragrance, a hair treatment, a bath salt, an essential oil, a bath bomb, and an enzyme.

14. The unit dose article of claim 1, wherein the first compartment and the second compartment are in the form of a laminate between the nonwoven web and water soluble film.

15. The unit dose article of claim 1, wherein the first compartment and the second compartment are provided in a side by side configuration.

16. The unit dose article of claim 1, wherein the first compartment and the second compartment are superposed.

17. The unit dose article of claim 1, wherein one of the first compartment and the second compartment comprises the first composition and the first composition comprises a surfactant, and the other compartment of the first compartment and the second compartment comprises a second composition comprising an enzyme.

18. The unit dose article of claim 1, wherein the unit dose article does not begin to release the first composition for about 1 minute.

19. A unit dose article comprising a compartment, the unit dose article comprising:

- a water soluble film in the form of a first pouch defining a first interior pouch volume, the water soluble film comprising a water soluble resin comprising a polyvinyl alcohol homopolymer, a polyvinyl alcohol copolymer, or a mixture of a polyvinyl alcohol homopolymer and a polyvinyl alcohol copolymer;
- a nonwoven web in the form of a second pouch defining a second interior pouch volume encompassing the water soluble film in the form of a pouch, the nonwoven web comprising a plurality of fibers comprising a first fiber type comprising a polyvinyl alcohol homopolymer having a degree of hydrolysis of about 92% to about 99.9% and a second fiber type comprising one or both of a non-water soluble polyester and a polylactic acid fiber forming material, wherein the water soluble film and the nonwoven web are in the form of a laminate; and a personal care composition disposed within the first interior pouch volume, the personal care composition comprising a surfactant.

* * * * *